US009682952B2

(12) United States Patent
Man et al.

(10) Patent No.: US 9,682,952 B2
(45) Date of Patent: Jun. 20, 2017

(54) ISOTOPOLOGUES OF 3-(5-AMINO-2-METHYL-4-OXOQUINAZOLIN-3(4H)-YL) PIPERIDINE-2-6-DIONE AND METHODS OF PREPARATION THEREOF

(71) Applicant: Celgene Corporation, Summit, NJ (US)

(72) Inventors: Hon-Wah Man, Princeton, NJ (US); William W. Leong, Westfield, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/425,479

(22) PCT Filed: Sep. 3, 2013

(86) PCT No.: PCT/US2013/057786
§ 371 (c)(1),
(2) Date: Mar. 3, 2015

(87) PCT Pub. No.: WO2014/039421
PCT Pub. Date: Mar. 13, 2014

(65) Prior Publication Data
US 2015/0203469 A1    Jul. 23, 2015

Related U.S. Application Data

(60) Provisional application No. 61/696,727, filed on Sep. 4, 2012.

(51) Int. Cl.
*C07D 401/04*    (2006.01)
(52) U.S. Cl.
CPC .................. *C07D 401/04* (2013.01)
(58) Field of Classification Search
CPC .................................................. C07D 401/04
USPC ..................................... 514/266.22; 544/287
See application file for complete search history.

(56) References Cited

U.S. PATENT DOCUMENTS

| | | | |
|---|---|---|---|
| 7,635,700 | B2 | 12/2009 | Muller et al. |
| 8,802,685 | B2 | 8/2014 | Muller et al. |
| 8,901,110 | B2 | 12/2014 | Kim et al. |
| 8,906,932 | B2 | 12/2014 | Muller et al. |
| 9,067,912 | B2 | 6/2015 | Ruchelman et al. |
| 9,095,596 | B2 | 8/2015 | Grimaldi et al. |
| 9,119,854 | B2 | 9/2015 | Chopra et al. |
| 9,358,232 | B2 | 6/2016 | Hege et al. |
| 9,365,640 | B2 | 6/2016 | Lopez-Girona et al. |
| 9,415,049 | B2 | 8/2016 | Tester et al. |
| 9,474,757 | B2 | 10/2016 | Hege et al. |
| 9,540,340 | B2 | 1/2017 | DeWitt |
| 2007/0135454 | A1 | 6/2007 | Bayliss et al. |
| 2009/0149484 | A1 | 6/2009 | Aquila et al. |
| 2009/0163525 | A1 | 6/2009 | Aquila et al. |
| 2009/0170849 | A1 | 7/2009 | Aquila et al. |
| 2009/0233947 | A1 | 9/2009 | Bayliss et al. |
| 2009/0298856 | A1 | 12/2009 | Brown |
| 2011/0152242 | A1 | 6/2011 | Bayliss et al. |
| 2013/0274291 | A1 | 10/2013 | DeWitt |
| 2014/0162282 | A1 | 6/2014 | Schafer et al. |
| 2014/0228382 | A1* | 8/2014 | DeWitt ............... C07D 401/04 514/266.22 |
| 2014/0288101 | A1 | 9/2014 | DeWitt |
| 2014/0301980 | A1 | 10/2014 | Day |
| 2014/0314752 | A1 | 10/2014 | Lopez-Girona et al. |
| 2015/0152511 | A1 | 6/2015 | Thakurta et al. |
| 2015/0196562 | A1 | 7/2015 | Bhat et al. |
| 2015/0203469 | A1 | 7/2015 | Man et al. |
| 2015/0224104 | A1 | 8/2015 | Gandhi et al. |
| 2015/0258082 | A1 | 9/2015 | Parlati et al. |
| 2015/0291562 | A1 | 10/2015 | Crew et al. |
| 2015/0374678 | A1 | 12/2015 | Chamberlain et al. |
| 2016/0002202 | A1 | 1/2016 | DeWitt |
| 2016/0045475 | A1 | 2/2016 | Day |
| 2016/0313300 | A1 | 10/2016 | Trotter et al. |
| 2016/0324878 | A1 | 11/2016 | He |

FOREIGN PATENT DOCUMENTS

| | | |
|---|---|---|
| WO | WO 03/007955 A2 | 1/2003 |
| WO | 2007/041630 A1 | 4/2007 |
| WO | WO 2012/027065 A2 | 3/2012 |
| WO | WO 2012/066330 A1 | 5/2012 |
| WO | WO 2015/107196 A1 | 7/2015 |
| WO | WO 2016/007854 A1 | 1/2016 |
| WO | WO 2016/014890 A1 | 1/2016 |
| WO | WO 2016/022969 A1 | 2/2016 |
| WO | WO 2016/060702 A1 | 4/2016 |
| WO | WO 2016/105518 A1 | 6/2016 |
| WO | WO 2016/151144 A1 | 9/2016 |

(Continued)

OTHER PUBLICATIONS

Pinedo et al. (2000).*
McMahon et al (2000).*
Vippagunta et al. (2001).*
Dyck et al., "Effects of Deuterium Substitution on the Catabolism of β-Phenylethylamine: An In Vivo Study", Journal of Neurochemistry, 1986, 46(2):399-404.
Gant, "Using deuterium in drug discovery: leaving the label in the drug," J. Med. Chem., 57:3595-3611 (2014).
Mullard, "Deuterated drugs draw heavier backing," Nature Rev., 15:219-221 (2016).

*Primary Examiner* — Paul V Ward
(74) *Attorney, Agent, or Firm* — Jones Day

(57) ABSTRACT

Provided herein are deuterated isotopologues of 3-(5-amino-2-methyl-4-oxoquinazolin-3(4H)-yl)piperidine-2,6-dione, or enantiomers or mixtures of enantiomers thereof; or a pharmaceutically acceptable salt, solvate, cocrystal or polymorph thereof, and processes for making the same. Pharmaceutical compositions comprising the isotopes-enriched compounds, and methods of using such compounds are also provided.

10 Claims, No Drawings

(56) References Cited

FOREIGN PATENT DOCUMENTS

| WO | WO 2016/153948 A1 | 9/2016 |
| WO | WO 2016/164336 A1 | 10/2016 |

\* cited by examiner ically
ISOTOPOLOGUES OF 3-(5-AMINO-2-METHYL-4-OXOQUINAZOLIN-3(4H)-YL) PIPERIDINE-2-6-DIONE AND METHODS OF PREPARATION THEREOF The present application is a 371 of International Application No. PCT/US2013/057786, filed Sep. 3, 2013, which claims priority to U.S. Provisional Patent Application No. 61/696,727, filed Sep. 4, 2012, the entirety of each of which is incorporated herein by reference.

I. FIELD

Provided herein are isotopologues of 3-(5-amino-2-methyl-4-oxoquinazolin-3(4H)-yl)piperidine-2,6-dione, compositions comprising the isotopologues, methods of making the isotopologues, and methods of their use for treatment or prevention of diseases and conditions including, but not limited to, inflammatory diseases, autoimmune diseases, and cancers.

II. BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J., and Kale, D., Immunology, 17.1-17.12 (3rd ed., Mosby, St. Louis, Mo., 1993).

There is an enormous variety of cancers which are described in detail in the medical literature. Examples include cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor induced angiogenesis have been elucidated. The most direct of these mechanisms is the secretion by the tumor cells of cytokines with angiogenic properties. Examples of these cytokines include acidic and basic fibroblastic growth factor (a,b FGF), angiogenin, vascular endothelial growth factor (VEGF), and TNF α. Alternatively, tumor cells can release angiogenic peptides through the production of proteases and the subsequent breakdown of the extracellular matrix where some cytokines are stored (e.g., b FGF). Angiogenesis can also be induced indirectly through the recruitment of inflammatory cells (particularly macrophages) and their subsequent release of angiogenic cytokines (e.g., TNF α, b-FGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; arthritis; and proliferative vitreoretinopathy.

Accordingly, compounds that can control angiogenesis or inhibit the production of certain cytokines, including TNFα, may be useful in the treatment and prevention of various diseases and conditions.

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., Goodman and Gilman's: The Pharmacological Basis of Therapeutics, Tenth Ed. (McGraw Hill, New York).

Despite availability of a variety of chemotherapeutic agents, chemotherapy has many drawbacks. Stockdale, Medicine, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Other diseases or conditions associated with, or characterized by, undesired angiogenesis are also difficult to treat.

However, some compounds such as protamine, heparin and steroids have been proposed to be useful in the treatment of certain specific diseases. (Taylor et al., *Nature* 297:307 (1982); Folkman et al., *Science* 221:719 (1983); and U.S. Pat. Nos. 5,001,116 and 4,994,443).

Still, there is a significant need for safe and effective methods of treating, preventing and managing cancer and other diseases and conditions, including for diseases that are refractory to standard treatments, such as surgery, radiation therapy, chemotherapy and hormonal therapy, while reducing or avoiding the toxicities and/or side effects associated with the conventional therapies.

Certain 4-oxoquinazoline compounds, including 3-(5-amino-2-methyl-4-oxoquinazolin-3(4H)-yl)piperidine-2,6-dione, have been reported to be capable of controlling angiogenesis or inhibiting the production of certain cytokines, including TNF-α, and useful in the treatment and prevention of various diseases and conditions. See U.S. Pat. No. 7,635,700, the disclosure of which is incorporated herein by reference in its entirety.

The molecule 3-(5-amino-2-methyl-4-oxoquinazolin-3(4H)-yl)piperidine-2,6-dione, which has the chemical structure:

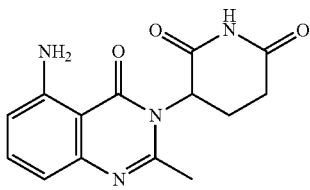 [SMILES: Cc1nc2cccc(N)c2c(=O)n1C1CCC(=O)NC1=O]

has been described in U.S. Pat. No. 7,635,700. A need still exists for efficient and scalable processes for the preparation of isotopologues of 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, cocrystal or polymorph thereof. The compound 3-(5-amino-2-methyl-4-oxoquinazolin-3(4H)-yl)piperidine-2,6-dione, its various isotopologues and compositions comprising the same have utility for, inter alia, treatment of certain cancers (e.g., multiple myeloma, myelodysplastic syndrome, chronic lymphocytic leukemia, and non-Hodgkin's lymphoma) and other various diseases and disorders.

III. SUMMARY

Provided herein are isotopologues of 3-(5-amino-2-methyl-4-oxoquinazolin-3(4H)-yl)piperidine-2,6-dione and methods for the preparation the isotopologues, or enantiomers or mixtures of enantiomers thereof; or pharmaceutically acceptable salts, solvates, hydrates, cocrystals or polymorphs thereof.

IV. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

The descriptions of the terminology provided below apply to the terms as used herein and unless otherwise specified.

The term "compound" includes salt, solvates (e.g., hydrates), cocrystals and polymorphs thereof.

The term "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. As used herein, an "isotopologue" is an isotopically enriched compound.

The term "isotopic enrichment" refers to the percentage of incorporation of an amount of a specific isotope at a given atom in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

The term "isotopic enrichment factor" refers to the ratio between the isotopic composition and the natural isotopic composition of a specified isotope.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium atom.

The isotopic enrichment and isotopic enrichment factor of the compounds provided herein can be determined using conventional analytical methods known to one of ordinary skill in the art, including mass spectrometry and nuclear magnetic resonance spectroscopy.

The term "alkyl" refers to a linear or branched saturated monovalent hydrocarbon radical, wherein the alkyl is optionally substituted with one or more substituents Q as described herein elsewhere. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one to five, in another embodiment, one, carbon-carbon double bond(s), wherein the alkenyl is optionally substituted with one or more substituents Q as described herein elsewhere. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s), wherein the alkynyl is optionally substituted with one or more substituents Q as described herein elsewhere. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, wherein the cycloalkyl is optionally substituted with one or more substituents Q as described herein elsewhere. In one embodiment, cycloalkyl groups may be saturated or unsaturated but non-aromatic, and/or spiro, and/or non-spiro, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic group and/or monovalent polycyclic aromatic group that contain at least one aromatic carbon ring, wherein the aryl is optionally substituted with one or more substituents Q as described herein elsewhere. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. The term "aryl" also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl).

The term "aralkyl" or "arylalkyl" refers to a monovalent alkyl group substituted with one or more aryl groups, wherein the aralkyl or arylalkyl is optionally substituted with one or more substituents Q as described herein elsewhere. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl.

The term "heteroaryl" refers to a monovalent monocyclic aromatic group and/or monovalent polycyclic aromatic group that contain at least one aromatic ring, wherein at least one aromatic ring contains one or more heteroatoms independently selected from O, S, N, and P in the ring. Heteroaryl groups are bonded to the rest of a molecule through the aromatic ring. Each ring of a heteroaryl group can contain one or two O atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein elsewhere.

The term "heterocyclyl" or "heterocyclic" refers to a monovalent monocyclic non-aromatic ring system and/or monovalent polycyclic ring system that contain at least one non-aromatic ring, wherein one or more of the non-aromatic ring atoms are heteroatoms independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein elsewhere.

The term "alkene" refers to a linear or branched hydrocarbon, which contains one or more, in one embodiment, one to five, in another embodiment, one, carbon-carbon double bond(s), wherein the alkene is optionally substituted with one or more substituents Q as described herein elsewhere. The term "alkene" embraces a compound having a "cis" or "trans" configuration or a mixture thereof, or alternatively, a "Z" or "E" configuration or a mixture thereof, as appreciated by those of ordinary skill in the art. For example, $C_{2-6}$ alkene refers to a linear unsaturated hydrocarbon of 2 to 6 carbon atoms or a branched unsaturated hydrocarbon of 3 to 6 carbon atoms. In certain embodiments, the alkene is a linear hydrocarbon of 2 to 20 ($C_{2-20}$), 2 to 15 ($C_{2-15}$), 2 to 10 ($C_{2-10}$), or 2 to 6 ($C_{2-6}$) carbon atoms, or a branched hydrocarbon of 3 to 20 ($C_{3-20}$), 3 to 15 ($C_{3-15}$), 3 to 10 ($C_{3-10}$), or 3 to 6 ($C_{3-6}$) carbon atoms.

The term "cycloalkene" refers to a cyclic hydrocarbon, which contains one or more, in one embodiment, one to five, in another embodiment, one, carbon-carbon double bond(s), wherein the cycloalkene is optionally substituted with one or more substituents Q as described herein elsewhere. In one embodiment, the cycloalkene may be non-aromatic, and/or spiro, and/or non-spiro, and/or bridged, and/or non-bridged, and/or fused bicyclic. In certain embodiments, the cycloalkene has from 3 to 20 ($C_{3-20}$), from 3 to 15 ($C_{3-15}$), from 3 to 10 ($C_{3-10}$), or from 3 to 7 ($C_{3-7}$) carbon atoms.

The term "arene" refers to a monocyclic aromatic compound and/or polycyclic aromatic compound that contain at least one aromatic carbon ring, wherein the arene is optionally substituted with one or more substituents Q as described herein elsewhere. In certain embodiments, the arene has from 6 to 20 ($C_{6-20}$), from 6 to 15 ($C_{6-15}$), or from 6 to 10 ($C_{6-10}$) ring atoms. The term "arene" also refers to bicyclic or tricyclic carbon rings, where one of the rings is aromatic and the other(s) may be saturated, partially unsaturated, or aromatic.

The term "heteroarene" refers to a monocyclic aromatic and/or polycyclic aromatic compound that contain at least one aromatic ring, wherein at least one aromatic ring contains one or more heteroatoms independently selected from O, S, N, and P in the ring. Each ring of a heteroarene can contain one or two O atoms, one or two S atoms, one to four N atoms, and/or one or two P atoms, provided that the total number of heteroatoms in each ring is four or less and each ring contains at least one carbon atom. In certain embodiments, the heteroarene has from 5 to 20, from 5 to 15, or from 5 to 10 ring atoms. In certain embodiments, the heteroarene is optionally substituted with one or more substituents Q as described herein elsewhere.

The term "heterocycle" refers to a monocyclic non-aromatic ring system and/or non-aromatic polycyclic ring system, wherein one or more of the non-aromatic ring atoms are heteroatoms, each of which is independently selected from O, S, N, and P; and the remaining ring atoms are carbon atoms. In certain embodiments, the heterocycle has from 3 to 20, from 3 to 15, from 3 to 10, from 3 to 8, from 4 to 7, or from 5 to 6 ring atoms. In certain embodiments, the heterocycle is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated. In certain embodiments, the heterocycle is optionally substituted with one or more substituents Q as described herein elsewhere.

The term "alcohol" refers to alkyl-OH, alkenyl-OH, alkynyl-OH, cycloalkyl-OH, aryl-OH, aralkyl-OH, heteroaryl-OH or, or heterocyclyl-OH, wherein the alkyl, alkenyl, alkynyl, cycloalkyl, aryl, aralkyl, heteroaryl, and heterocyclyl are each as defined herein. The term "carboxylic acid" refers to alkyl-COOH, alkenyl-COOH, alkynyl-COOH, cycloalkyl-COOH, aryl-COOH, aralkyl-COOH, heteroaryl-COOH, or heterocyclyl-COOH, wherein the alkyl, alkenyl, alkynyl, cycloalkyl, aryl, aralkyl, heteroaryl, and heterocyclyl are each as defined herein.

The term "carboxylic acid ester" or "ester" refers to alkyl-COOR', alkenyl-COOR', alkynyl-COOR', cycloalkyl-COOR', aryl-COOR', aralkyl-COOR', heteroaryl-COOR', or heterocyclyl-COOR', and each R' is independently wherein alkyl, alkenyl, alkynyl, cycloalkyl, aryl, aralkyl, heteroaryl, and heterocyclyl; and wherein each alkyl, alkenyl, alkynyl, cycloalkyl, aryl, aralkyl, heteroaryl, and heterocyclyl is as defined herein.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more substituents Q, each of which is independently selected from, e.g., (a) oxo (=O), halo, cyano (—CN), and nitro (—NO$_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —P(O)$R^aR^d$, —P(O)(O$R^a$)$R^d$, —P(O)(O$R^a$)(O$R^d$), —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heteroaryl or heterocyclyl, each of which optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) R$^f$ and R$^g$ together with the N atom to which they are attached form heteroaryl or heterocyclyl.

The term "pharmaceutically acceptable salt(s)," as used herein includes, but is not limited to, salts of isotopologues of 3-(5-amino-2-methyl-4-oxoquinazolin-3(4H)-yl)piperidine-2,6-dione. Basic moieties such as 3-(5-amino-2-methyl-4-oxoquinazolin-3(4H)-yl)piperidine-2,6-dione are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (i.e., 1,1'-methylene-bis-(2-hydroxy-3-naphthoate) acids, or isotopically enriched analogues thereof. Suitable inorganic acids include, but are not limited to, hydrochloric, hydrobromic, hydroiodic, sulfuric, phosphoric, or nitric acids, or isotopically enriched analogues thereof.

All of the compounds, functional groups and pharmaceutically acceptable salts provided herein may have one or more isotopically enriched hydrogen atom at one or more positions. Examples include, but are not limited to, isotopically enriched alcohols, carboxylic acids, carboxylic acid esters, or alkyl, alkenyl, alkynyl, cycloalkyl, aryl, aralkyl, heteroaryl, or heterocyclyl groups, wherein the alkyl, alkenyl, alkynyl, cycloalkyl, aryl, aralkyl, heteroaryl, and heterocyclyl are each as defined herein. For example, the term "alcohol" may include, but is not limited to alkyl-OD, alkenyl-OD, alkynyl-OD, cycloalkyl-OD, aryl-OD, aralkyl-OD, heteroaryl-OD, or heterocyclyl-OD, wherein the alkyl, alkenyl, alkynyl, cycloalkyl, aryl, aralkyl, heteroaryl, and heterocyclyl are each as defined herein.

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "polymorph" refers to solid crystalline forms of a compound or complex thereof. Different polymorphs of the same compound can exhibit different physical, chemical and spectroscopic properties.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "substantially free" when referring to a composition that is "substantially free" of a compound refers means that the composition contains no greater than about 20% by weight, no greater than about 10% by weight, no greater than about 5% by weight, no greater than about 3% by weight, no greater than about 1% by weight, no greater than about 0.5% by weight, no greater than about 0.2% by weight, no greater than about 0.1% by weight, no greater than about 0.01% by weight, no greater than about 0.001% by weight, or no greater than about 0.0001% by weight of the compound.

The term "substantially pure" when referring to a compound or composition means that the compound or composition has a purity of no less than about 80% by weight, no less than about 90% by weight, no less than about 95% by weight, no less than about 96% by weight, no less than about 97% by weight, no less than about 98% by weight, no less than about 99% by weight, no less than about 99.5% by weight, no less than about 99.9% by weight, no less than about 99.95% by weight, no less than about 99.99% by weight, no less than about 99.995% by weight, no less than about 99.999% by weight, no less than about 99.9995% by weight, or no less than about 99.9999% by weight.

The terms "process" and "method" are used interchangeably to refer to a method disclosed herein for a compound preparation. Modifications to the processes and methods disclosed herein (e.g., starting materials, reagents, protecting groups, solvents, temperatures, reaction times, and/or purification) that are well known to those of ordinary skill in the art are also encompassed by the disclosure.

The terms "adding," "reacting," "contacting" and "mixing" are used interchangeably to refer to contacting one reactant, reagent, solvent, catalyst, or a reactive group with another reactant, reagent, solvent, catalyst, or reactive group. Unless otherwise specified, reactants, reagents, solvents, catalysts, and reactive groups can be added individually, simultaneously, or separately, and/or can be added in any order. They can be added in the presence or absence of heat, and can optionally be added under an inert atmosphere (e.g., $N_2$ or Ar). In certain embodiments, the term "reacting" can also refer to in situ formation or intra-molecular reaction where the reactive groups are in the same molecule.

The term "substantially complete" when referring to a reaction means that the reaction contains no greater than about 50%, no greater than about 40%, no greater than about 30%, no greater than about 20%, no greater than about 10%, no greater than about 5%, no greater than about 4%, no greater than about 3%, no greater than about 2%, no greater than about 1%, no greater than about 0.5%, no greater than about 0.1%, or no greater than about 0.05% of a starting material left.

If the stereochemistry of a structure or a portion thereof is not indicated, e.g., with bold or dashed lines, the structure or portion thereof is to be interpreted as encompassing all stereoisomers of the structure.

The phrase "an enantiomer or a mixture of enantiomers thereof; or a pharmaceutically acceptable salt, solvate, hydrate, cocrystal or polymorph thereof" has the same meaning as the phrase "an enantiomer or a mixture of enantiomers of the compound referenced therein; a pharmaceutically acceptable salt, solvate, hydrate, or polymorph of the compound referenced therein; or a pharmaceutically acceptable salt, solvate, hydrate, cocrystal or polymorph of an enantiomer or a mixture of enantiomers of the compound referenced therein."

B. Compounds

Provided herein are isotopologues of 3-(5-amino-2-methyl-4-oxoquinazolin-3(4H)-yl)piperidine-2,6-dione, synthetic intermediates thereof, and metabolites thereof.

Isotopic enrichment (e.g., deuteration) of pharmaceuticals to improve pharmacokinetics ("PK"), pharmacodynamics ("PD"), and toxicity profiles, has been demonstrated previously with some classes of drugs. (See, e.g., Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999)).

Without being limited by a particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes may often result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

In some embodiments, provided herein are isotopologues of 3-(5-amino-2-methyl-4-oxoquinazolin-3(4H)-yl)piperidine-2,6-dione, in which one or more atomic positions of the 3-(5-amino-2-methyl-4-oxoquinazolin-3 (4H)-yl)piperidine-2,6-dione molecule is/are isotopically enriched with deuterium. Certain embodiments herein provide compounds of the following chemical structure:

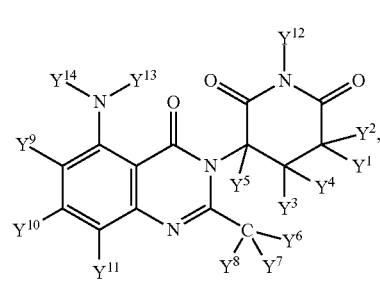

in which one or more Y atoms (i.e., $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$) is/are hydrogen(s) isotopically enriched with deuterium, and any remaining Y atom(s) is/are non-enriched hydrogen atom(s). In particular embodiments, one, two, three, four, five, six, seven, eight, nine, ten, eleven, twelve, thirteen or all of the indicated Y atoms is/are isotopically enriched with deuterium, and any remaining Y atom(s) is/are non-enriched hydrogen(s).

In certain embodiments, one or more Y atoms on the glutarimide portion of Compound I are deuterium-enriched. In certain embodiments, one or more Y atoms on the oxoquinazoline portion of Compound I are deuterium-enriched. In certain embodiments, one or more Y atoms on both the glutarimide portion and the oxoquinazoline portion of Compound I are deuterium-enriched, i.e., any combination of deuteration shown above for the glutarimide portion and the oxoquinazoline portion is encompassed. For example, particular compounds provided herein include the following listed compounds in Table 1, in which the label "D" indicates a deuterium-enriched atomic position, i.e., a sample comprising the given compound has a deuterium enrichment at the indicated position(s) above the natural abundance of deuterium:

TABLE 1

Deuterium enriched compounds of formula (I):

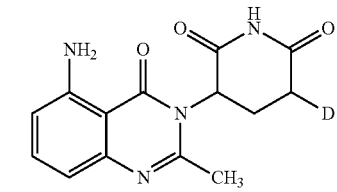 [SMILES: [2H]C1CC(n2c(C)nc3cccc(N)c3c2=O)C(=O)NC1=O]

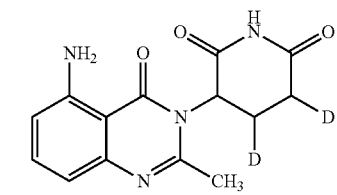 [SMILES: [2H]C1C(=O)NC(=O)C(n2c(C)nc3cccc(N)c3c2=O)C1[2H]]

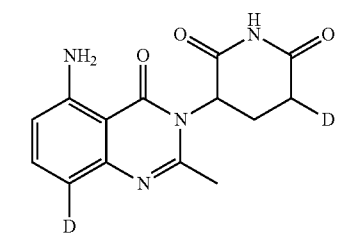 [SMILES: [2H]c1ccc(N)c2c(=O)n(C3CC([2H])C(=O)NC3=O)c(C)nc12]

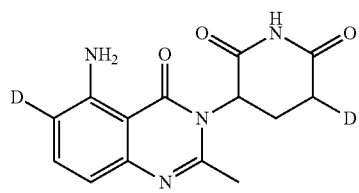 [SMILES: [2H]c1ccc2nc(C)n(C3CC([2H])C(=O)NC3=O)c(=O)c2c1N]

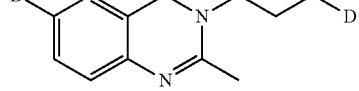
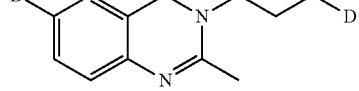
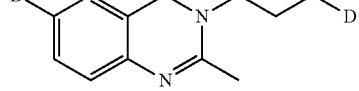
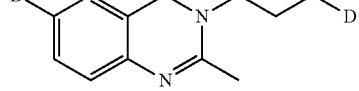

TABLE 1-continued

Deuterium enriched compounds of formula (I):

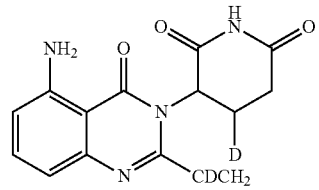

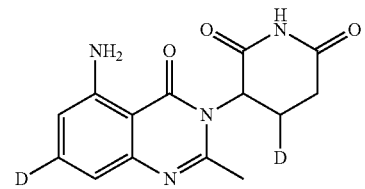 [SMILES: [2H]c1cc(N)c2c(=O)n(C3C(=O)NC(=O)CC3[2H])c(C)nc2c1]

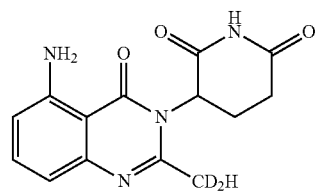

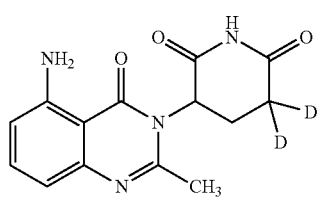 [SMILES: [2H]C1([2H])CC(n2c(C)nc3cccc(N)c3c2=O)C(=O)NC1=O]

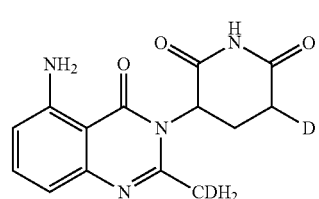

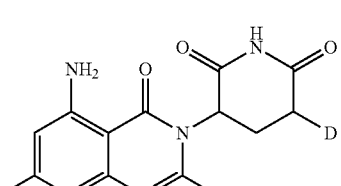

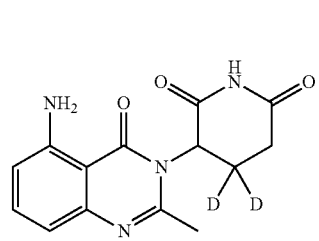 [SMILES: [2H]C1([2H])CC(=O)NC(=O)C1n1c(C)nc2cccc(N)c2c1=O]

TABLE 1-continued
Deuterium enriched compounds of formula (I):
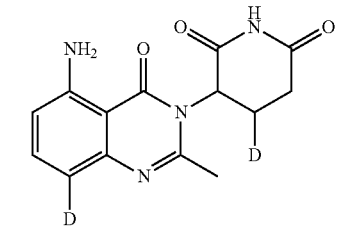 [SMILES: [2H]c1ccc(N)c2c(=O)n(C3C(=O)NC(=O)CC3[2H])c(C)nc12]
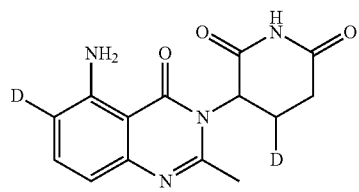 [SMILES: [2H]c1ccc2nc(C)n(C3C(=O)NC(=O)CC3[2H])c(=O)c2c1N]
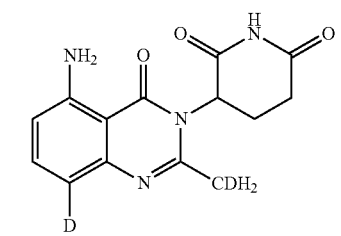
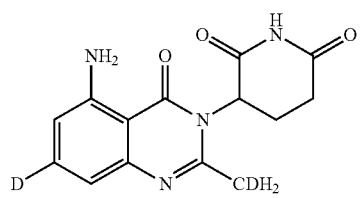
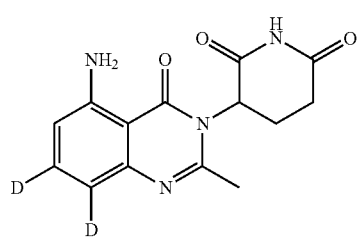 [SMILES: [2H]c1cc(N)c2c(=O)n(C3CCC(=O)NC3=O)c(C)nc2c1[2H]]
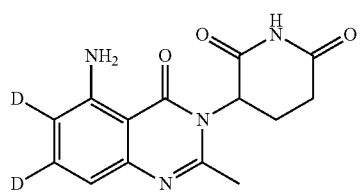 [SMILES: [2H]c1cc2nc(C)n(C3CCC(=O)NC3=O)c(=O)c2c(N)c1[2H]]
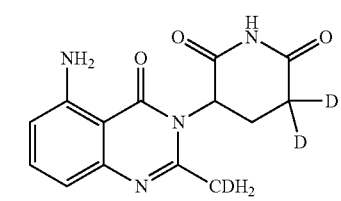
TABLE 1-continued
Deuterium enriched compounds of formula (I):
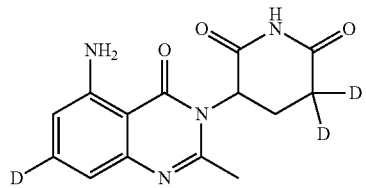 [SMILES: [2H]c1cc(N)c2c(=O)n(C3CC([2H])([2H])C(=O)NC3=O)c(C)nc2c1]
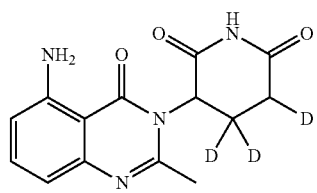 [SMILES: [2H]C1C(=O)NC(=O)C(n2c(C)nc3cccc(N)c3c2=O)C1([2H])[2H]]
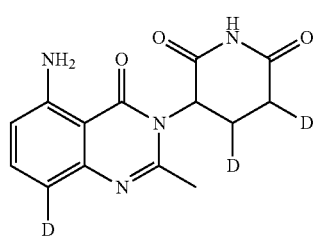 [SMILES: [2H]c1ccc(N)c2c(=O)n(C3C(=O)NC(=O)C([2H])C3[2H])c(C)nc12]
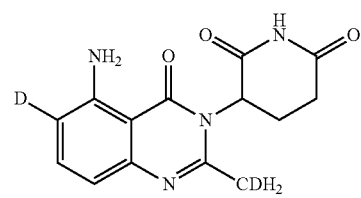
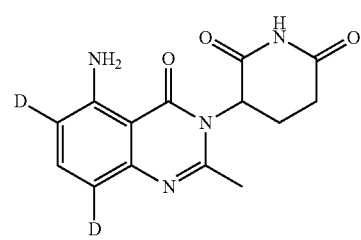
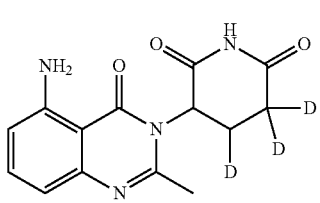 [SMILES: [2H]C1C(n2c(C)nc3cccc(N)c3c2=O)C(=O)NC(=O)C1([2H])[2H]]
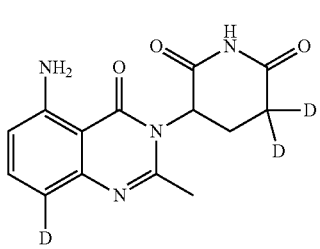 [SMILES: [2H]c1ccc(N)c2c(=O)n(C3CC([2H])([2H])C(=O)NC3=O)c(C)nc12]

TABLE 1-continued
Deuterium enriched compounds of formula (I):
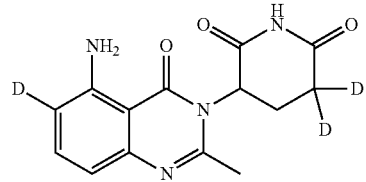 [SMILES: [2H]c1ccc2nc(C)n(C3CC([2H])([2H])C(=O)NC3=O)c(=O)c2c1N]
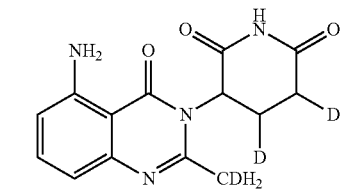
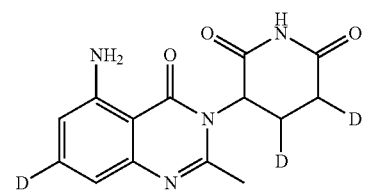 [SMILES: [2H]c1cc(N)c2c(=O)n(C3C(=O)NC(=O)C([2H])C3[2H])c(C)nc2c1]
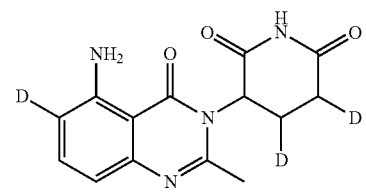 [SMILES: [2H]c1ccc2nc(C)n(C3C(=O)NC(=O)C([2H])C3[2H])c(=O)c2c1N]
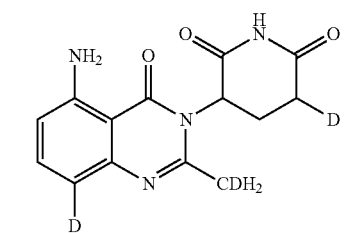
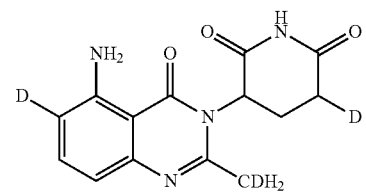
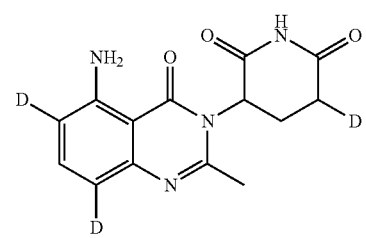 [SMILES: [2H]c1cc([2H])c2nc(C)n(C3CC([2H])C(=O)NC3=O)c(=O)c2c1N]
TABLE 1-continued
Deuterium enriched compounds of formula (I):
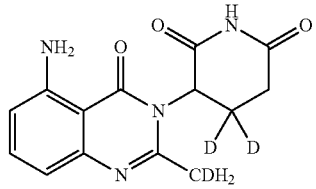
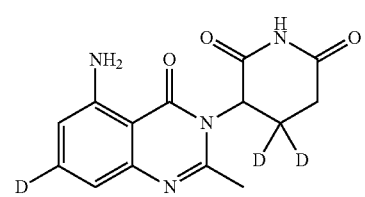 [SMILES: [2H]c1cc(N)c2c(=O)n(C3C(=O)NC(=O)CC3([2H])[2H])c(C)nc2c1]
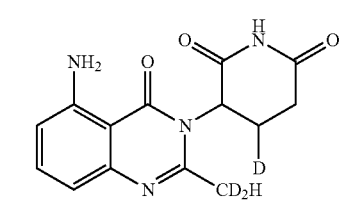
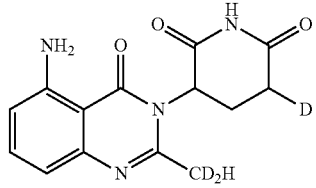
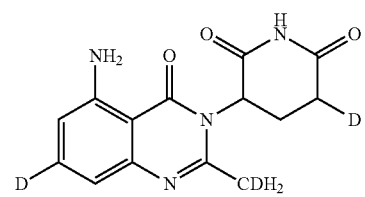
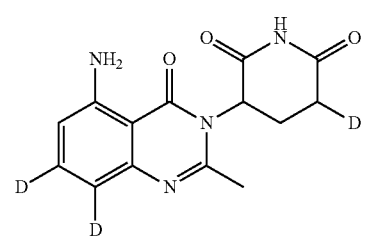 [SMILES: [2H]c1cc(N)c2c(=O)n(C3CC([2H])C(=O)NC3=O)c(C)nc2c1[2H]]
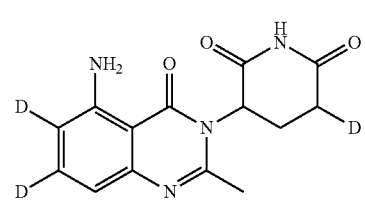 [SMILES: [2H]c1cc2nc(C)n(C3CC([2H])C(=O)NC3=O)c(=O)c2c(N)c1[2H]]

TABLE 1-continued
Deuterium enriched compounds of formula (I):
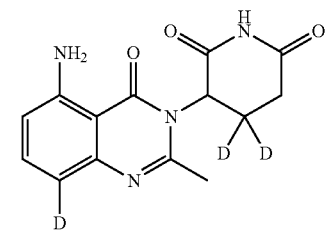 [SMILES: [2H]c1ccc(N)c2c(=O)n(C3C(=O)NC(=O)CC3([2H])[2H])c(C)nc12]
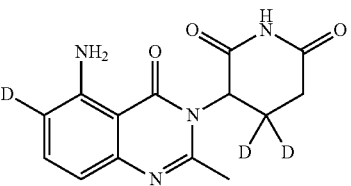 [SMILES: [2H]c1ccc2nc(C)n(C3C(=O)NC(=O)CC3([2H])[2H])c(=O)c2c1N]
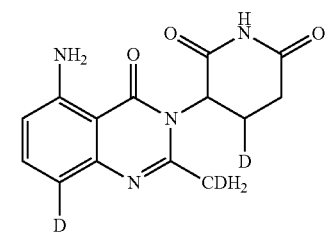
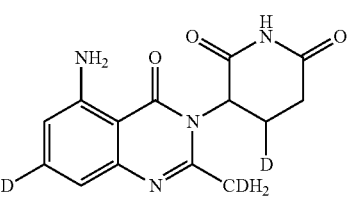
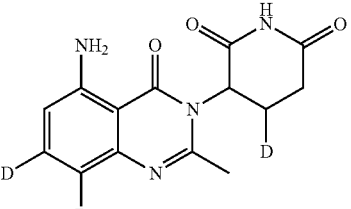
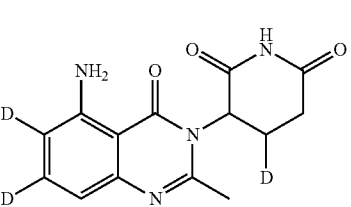 [SMILES: [2H]c1cc2nc(C)n(C3C(=O)NC(=O)CC3[2H])c(=O)c2c(N)c1[2H]]
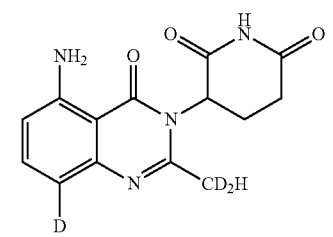
TABLE 1-continued
Deuterium enriched compounds of formula (I):
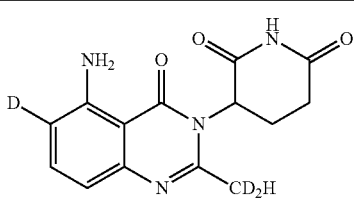
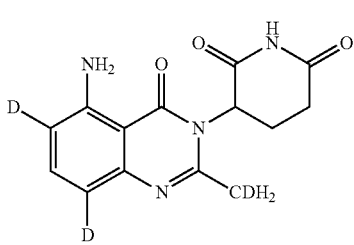
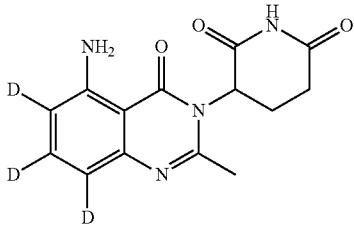 [SMILES: [2H]c1c([2H])c(N)c2c(=O)n(C3CCC(=O)NC3=O)c(C)nc2c1[2H]]
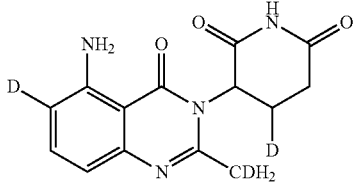
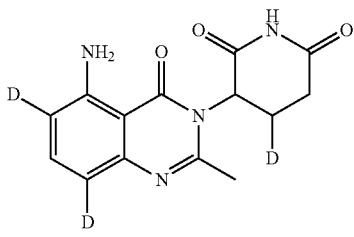 [SMILES: [2H]c1cc([2H])c2nc(C)n(C3C(=O)NC(=O)CC3[2H])c(=O)c2c1N]
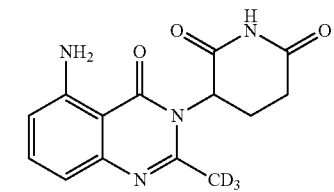 [SMILES: [2H]C([2H])([2H])c1nc2cccc(N)c2c(=O)n1C1CCC(=O)NC1=O]
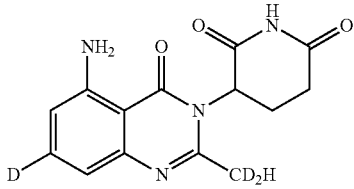

TABLE 1-continued
Deuterium enriched compounds of formula (I):
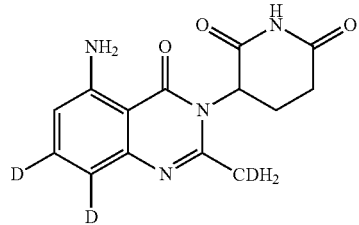
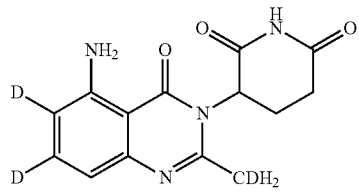
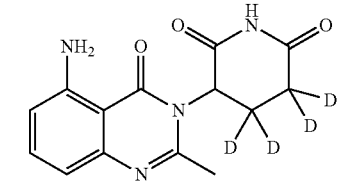 [SMILES: [2H]C1([2H])C(=O)NC(=O)C(n2c(C)nc3cccc(N)c3c2=O)C1([2H])[2H]]
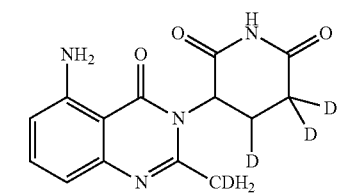
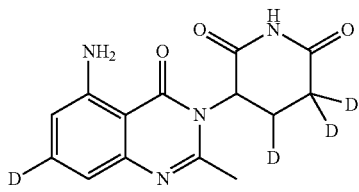 [SMILES: [2H]c1cc(N)c2c(=O)n(C3C(=O)NC(=O)C([2H])([2H])C3[2H])c(C)nc2c1]
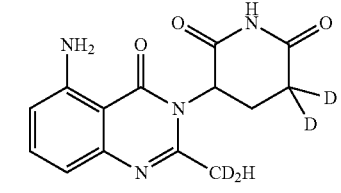
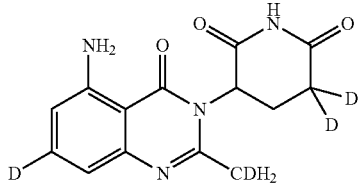
TABLE 1-continued
Deuterium enriched compounds of formula (I):
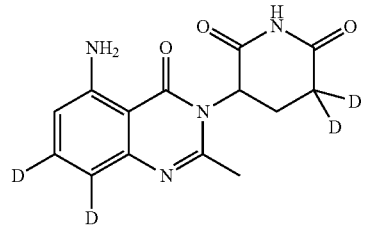 [SMILES: [2H]c1cc(N)c2c(=O)n(C3CC([2H])([2H])C(=O)NC3=O)c(C)nc2c1[2H]]
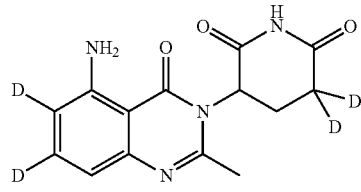 [SMILES: [2H]c1cc2nc(C)n(C3CC([2H])([2H])C(=O)NC3=O)c(=O)c2c(N)c1[2H]]
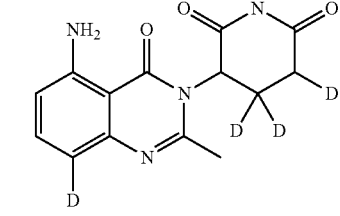
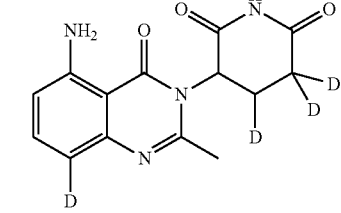
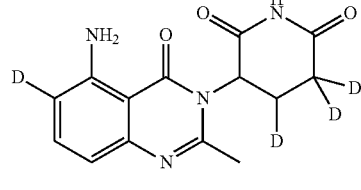
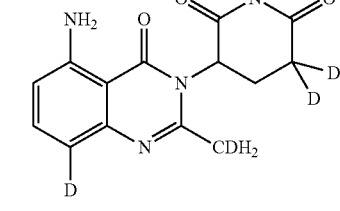
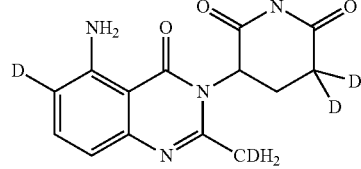

TABLE 1-continued
Deuterium enriched compounds of formula (I):
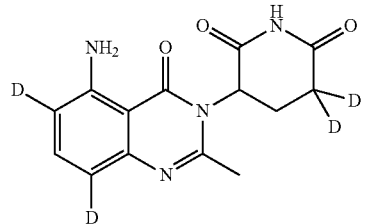 [SMILES: [2H]c1cc([2H])c2nc(C)n(C3CC([2H])([2H])C(=O)NC3=O)c(=O)c2c1N]
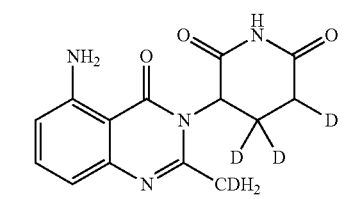
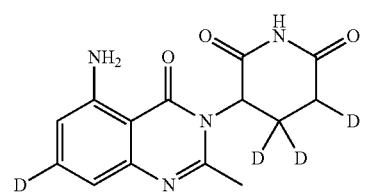 [SMILES: [2H]c1cc(N)c2c(=O)n(C3C(=O)NC(=O)C([2H])C3([2H])[2H])c(C)nc2c1]
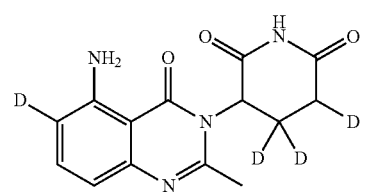 [SMILES: [2H]c1ccc2nc(C)n(C3C(=O)NC(=O)C([2H])C3([2H])[2H])c(=O)c2c1N]
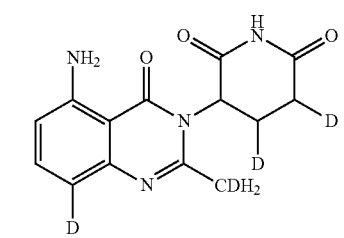
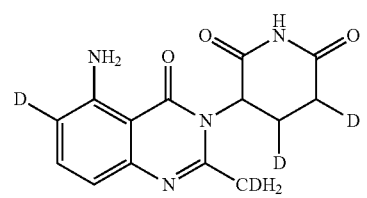
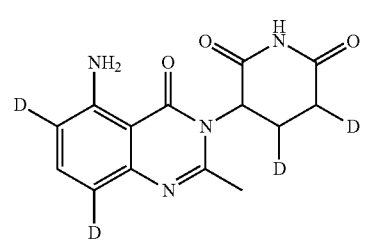 [SMILES: [2H]c1cc([2H])c2nc(C)n(C3C(=O)NC(=O)C([2H])C3[2H])c(=O)c2c1N]
TABLE 1-continued
Deuterium enriched compounds of formula (I):
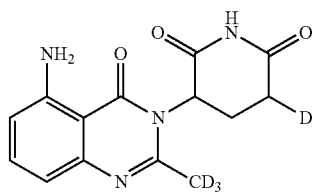
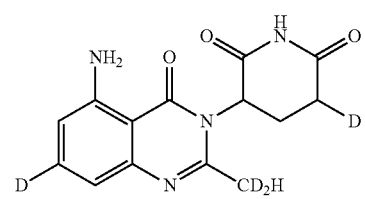
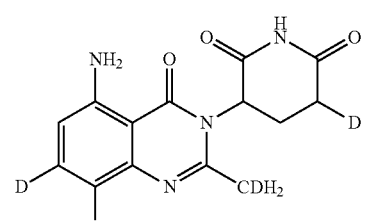
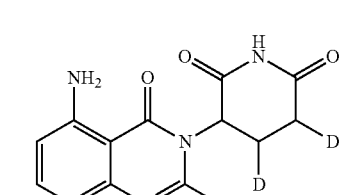
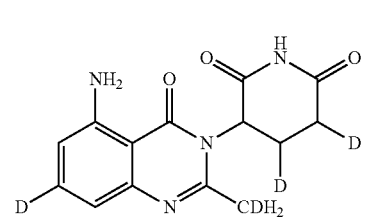
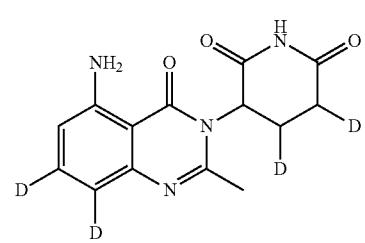 [SMILES: [2H]c1cc(N)c2c(=O)n(C3C(=O)NC(=O)C([2H])C3[2H])c(C)nc2c1[2H]]
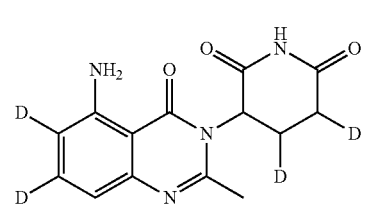 [SMILES: [2H]c1cc2nc(C)n(C3C(=O)NC(=O)C([2H])C3[2H])c(=O)c2c(N)c1[2H]]

TABLE 1-continued
Deuterium enriched compounds of formula (I):
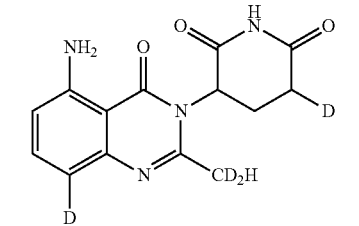
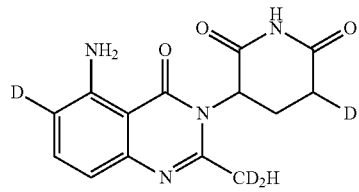
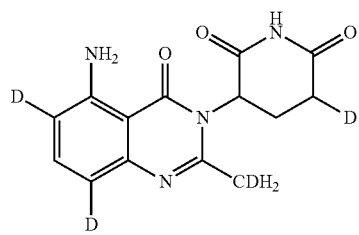
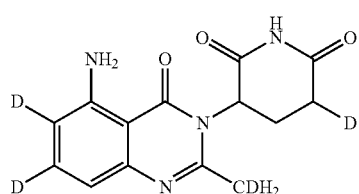
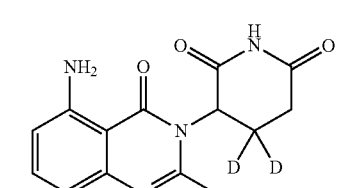
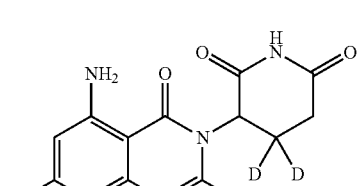
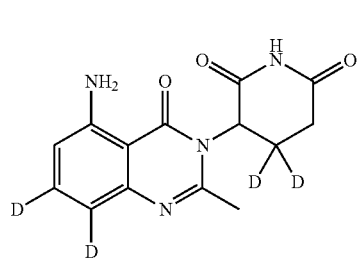 [SMILES: [2H]c1cc(N)c2c(=O)n(C3C(=O)NC(=O)CC3([2H])[2H])c(C)nc2c1[2H]]
TABLE 1-continued
Deuterium enriched compounds of formula (I):
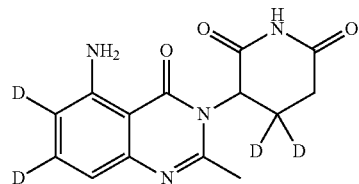 [SMILES: [2H]c1cc2nc(C)n(C3C(=O)NC(=O)CC3([2H])[2H])c(=O)c2c(N)c1[2H]]
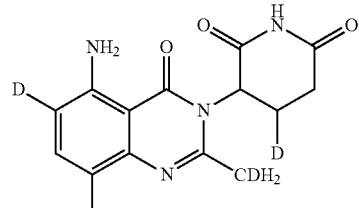
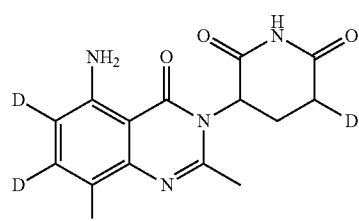
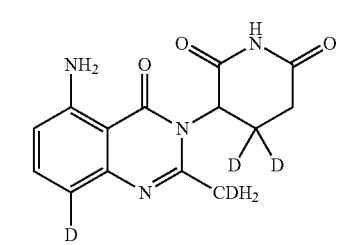
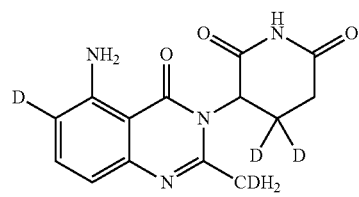
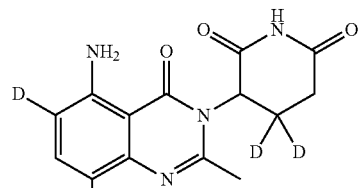
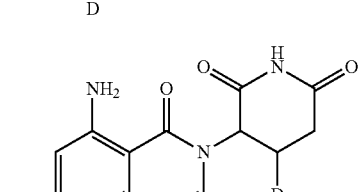

TABLE 1-continued
Deuterium enriched compounds of formula (I):
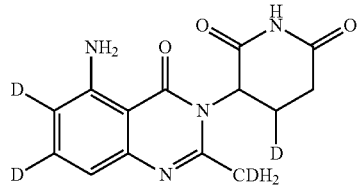
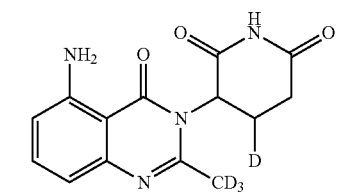
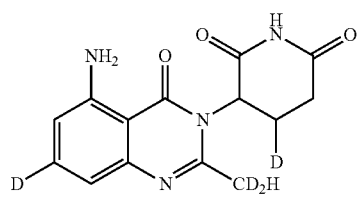
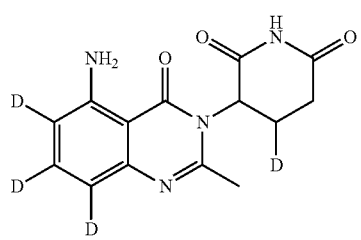 [SMILES: [2H]c1c([2H])c(N)c2c(=O)n(C3C(=O)NC(=O)CC3[2H])c(C)nc2c1[2H]]
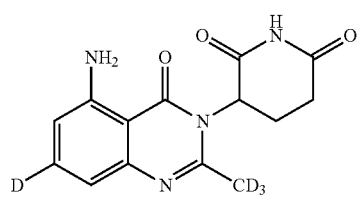 [SMILES: [2H]c1cc(N)c2c(=O)n(C3CCC(=O)NC3=O)c(C([2H])([2H])[2H])nc2c1]
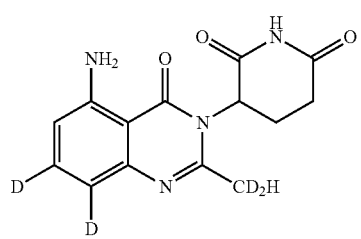
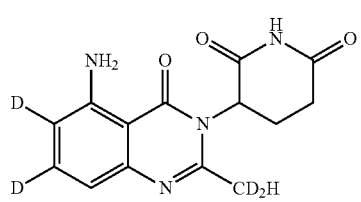
TABLE 1-continued
Deuterium enriched compounds of formula (I):
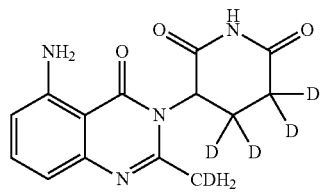
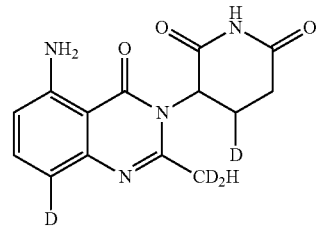
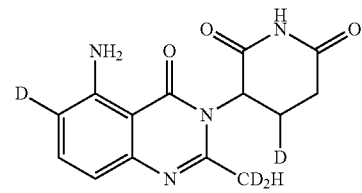
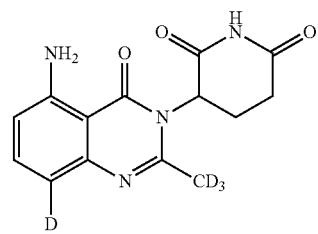 [SMILES: [2H]c1ccc(N)c2c(=O)n(C3CCC(=O)NC3=O)c(C([2H])([2H])[2H])nc12]
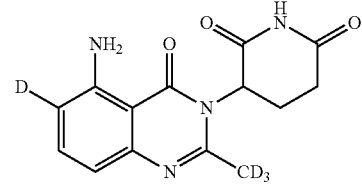 [SMILES: [2H]c1ccc2nc(C([2H])([2H])[2H])n(C3CCC(=O)NC3=O)c(=O)c2c1N]
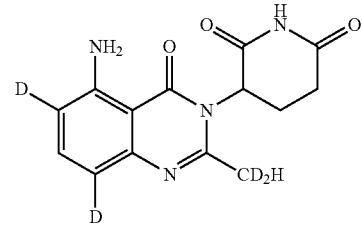
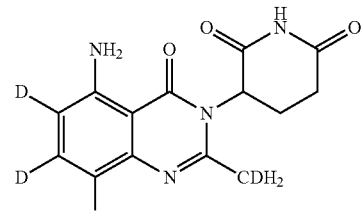

TABLE 1-continued
Deuterium enriched compounds of formula (I):
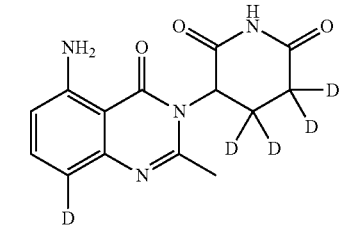 [SMILES: [2H]c1ccc(N)c2c(=O)n(C3C(=O)NC(=O)C([2H])([2H])C3([2H])[2H])c(C)nc12]
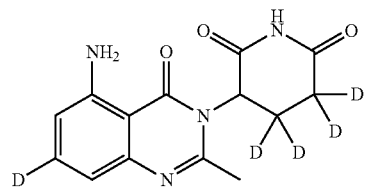 [SMILES: [2H]c1cc(N)c2c(=O)n(C3C(=O)NC(=O)C([2H])([2H])C3([2H])[2H])c(C)nc2c1]
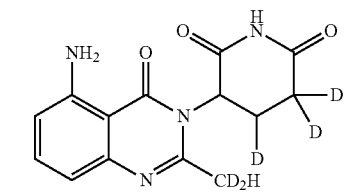
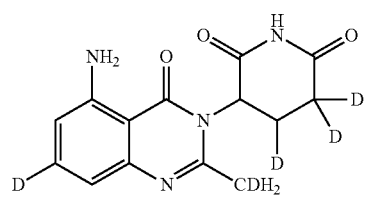
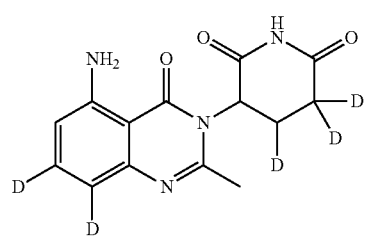 [SMILES: [2H]c1cc(N)c2c(=O)n(C3C(=O)NC(=O)C([2H])([2H])C3[2H])c(C)nc2c1[2H]]
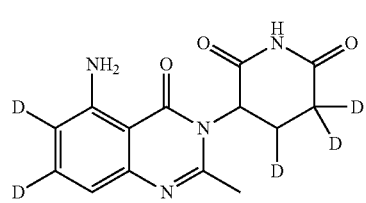 [SMILES: [2H]c1cc2nc(C)n(C3C(=O)NC(=O)C([2H])([2H])C3[2H])c(=O)c2c(N)c1[2H]]
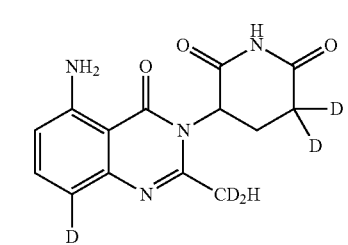
TABLE 1-continued
Deuterium enriched compounds of formula (I):
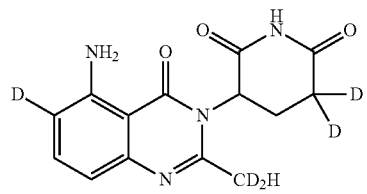
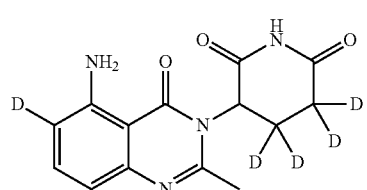
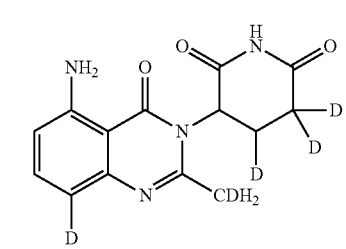
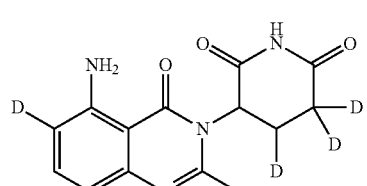
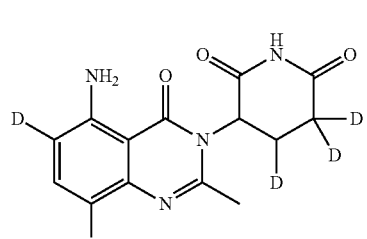
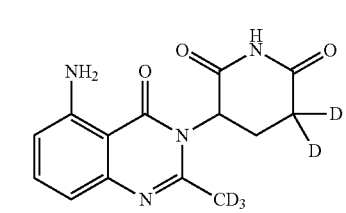 [SMILES: [2H]C1([2H])CC(n2c(C([2H])([2H])[2H])nc3cccc(N)c3c2=O)C(=O)NC1=O]
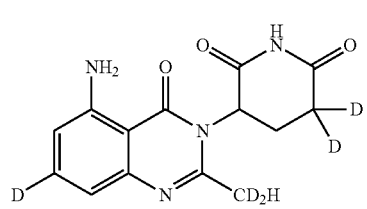

TABLE 1-continued
Deuterium enriched compounds of formula (I):
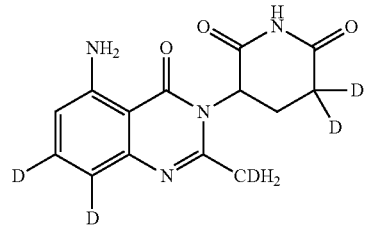
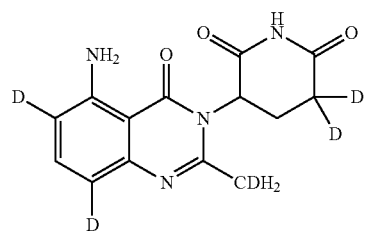
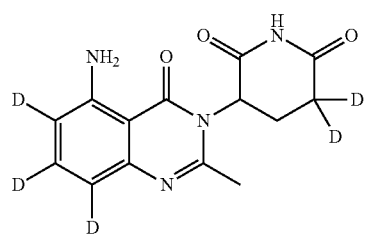 [SMILES: [2H]c1c([2H])c(N)c2c(=O)n(C3CC([2H])([2H])C(=O)NC3=O)c(C)nc2c1[2H]]
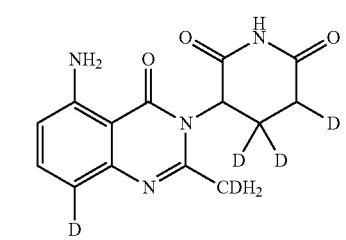
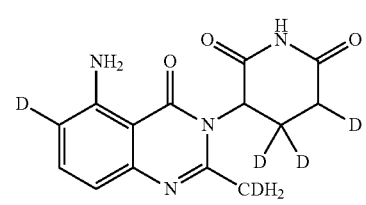
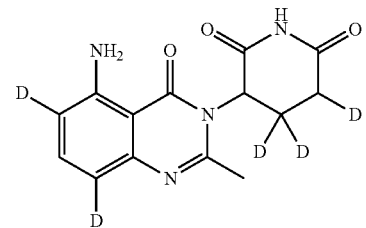 [SMILES: [2H]c1cc([2H])c2nc(C)n(C3C(=O)NC(=O)C([2H])C3([2H])[2H])c(=O)c2c1N]
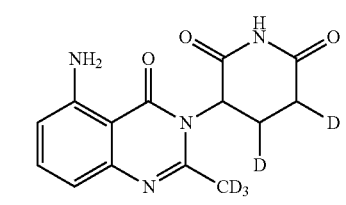
TABLE 1-continued
Deuterium enriched compounds of formula (I):
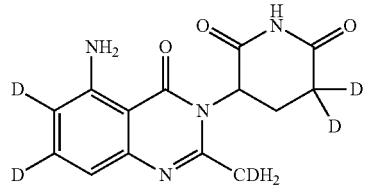
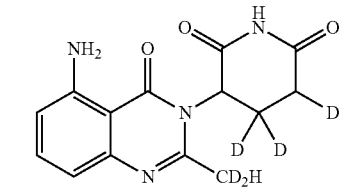
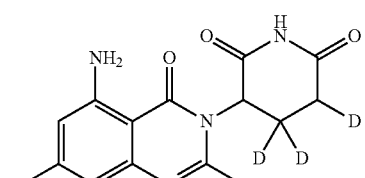
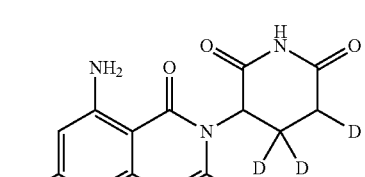
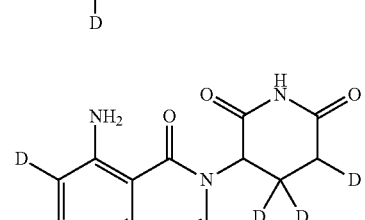
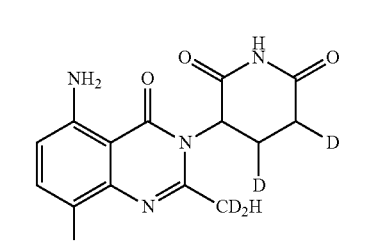
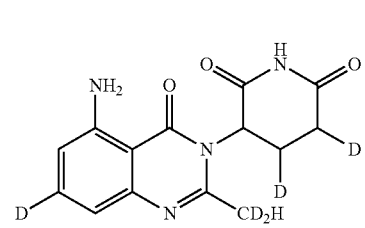

TABLE 1-continued
Deuterium enriched compounds of formula (I):
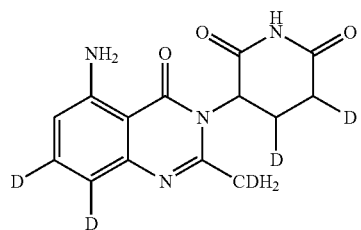
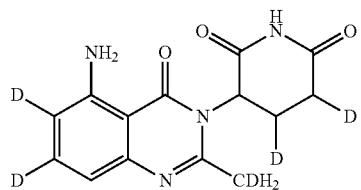
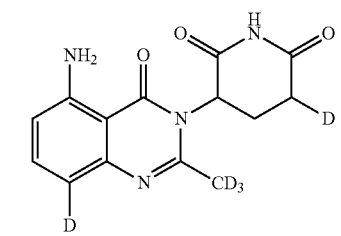 [SMILES: [2H]c1ccc(N)c2c(=O)n(C3CC([2H])C(=O)NC3=O)c(C([2H])([2H])[2H])nc12]
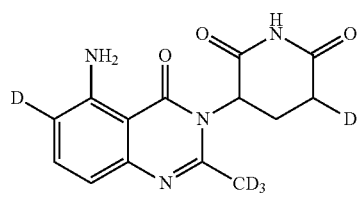 [SMILES: [2H]c1ccc2nc(C([2H])([2H])[2H])n(C3CC([2H])C(=O)NC3=O)c(=O)c2c1N]
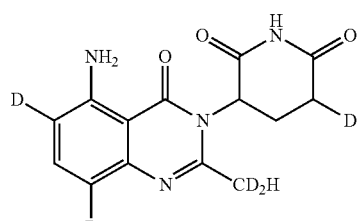
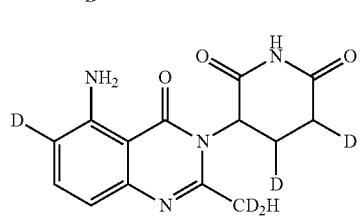
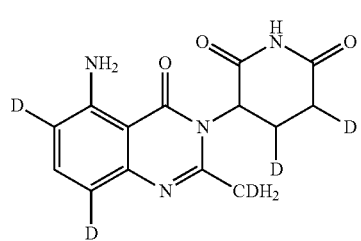
TABLE 1-continued
Deuterium enriched compounds of formula (I):
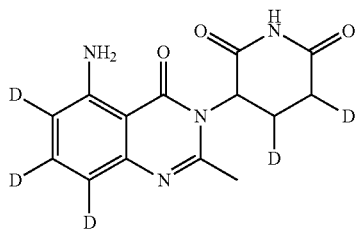 [SMILES: [2H]c1c([2H])c(N)c2c(=O)n(C3C(=O)NC(=O)C([2H])C3[2H])c(C)nc2c1[2H]]
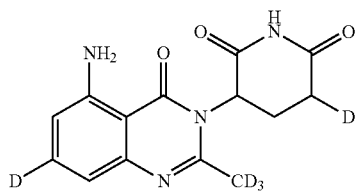
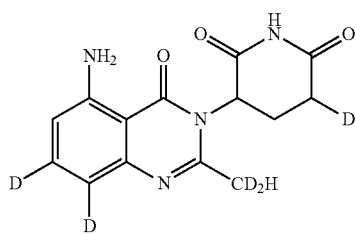
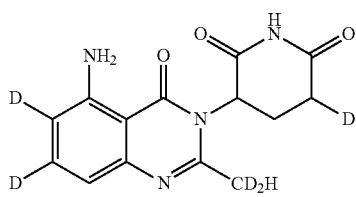
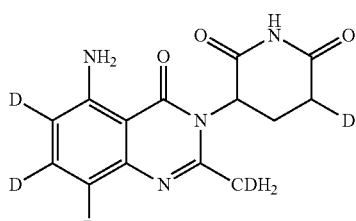
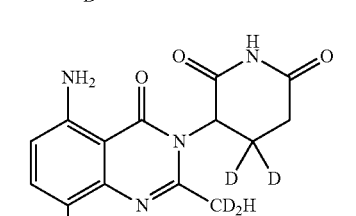
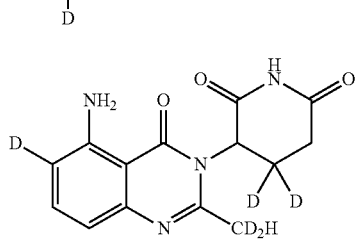

TABLE 1-continued
Deuterium enriched compounds of formula (I):
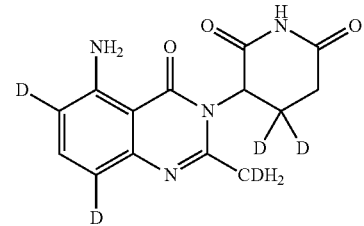
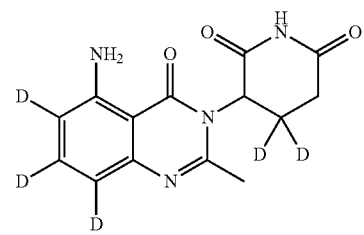 [SMILES: [2H]c1c([2H])c(N)c2c(=O)n(C3C(=O)NC(=O)CC3([2H])[2H])c(C)nc2c1[2H]]
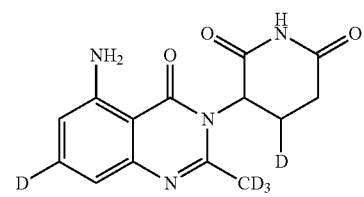
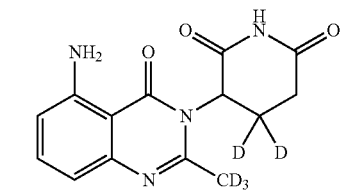 [SMILES: [2H]C([2H])([2H])c1nc2cccc(N)c2c(=O)n1C1C(=O)NC(=O)CC1([2H])[2H]]
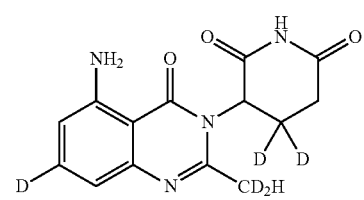
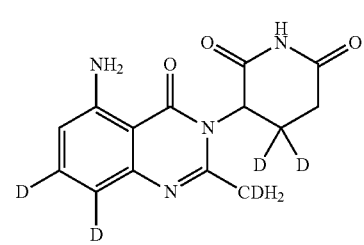
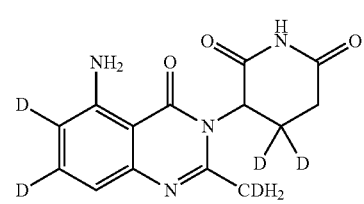
TABLE 1-continued
Deuterium enriched compounds of formula (I):
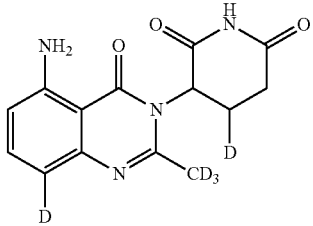 [SMILES: [2H]c1ccc(N)c2c(=O)n(C3C(=O)NC(=O)CC3[2H])c(C([2H])([2H])[2H])nc12]
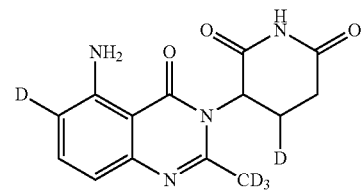
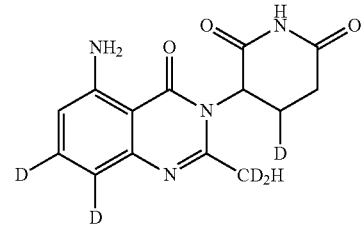
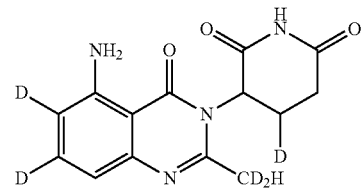
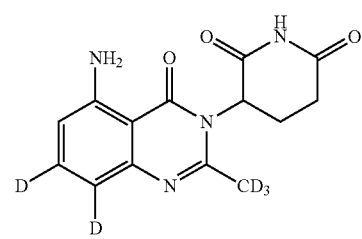
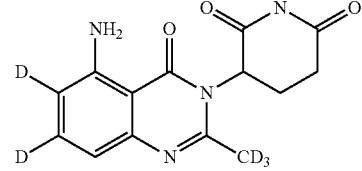
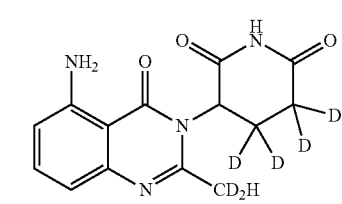

TABLE 1-continued
Deuterium enriched compounds of formula (I):
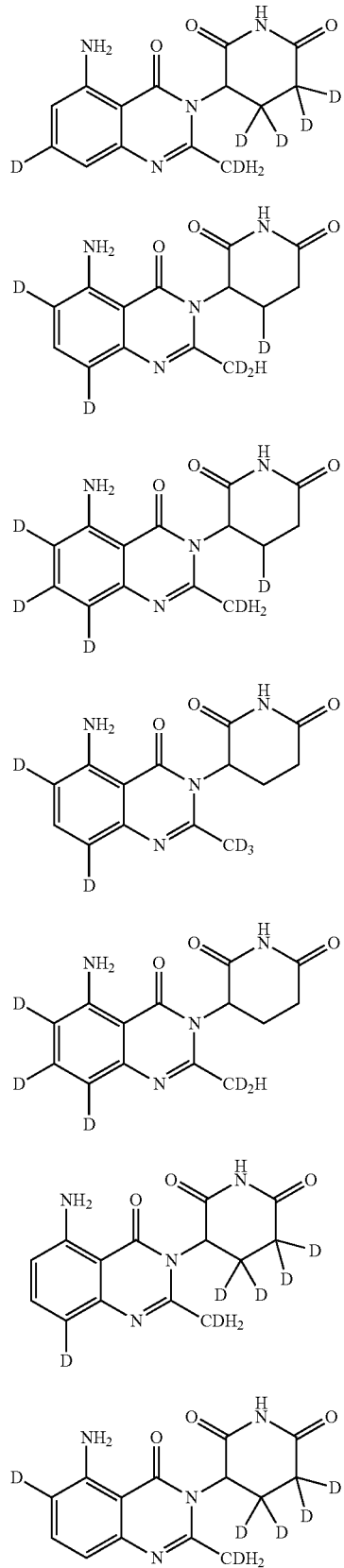
TABLE 1-continued
Deuterium enriched compounds of formula (I):
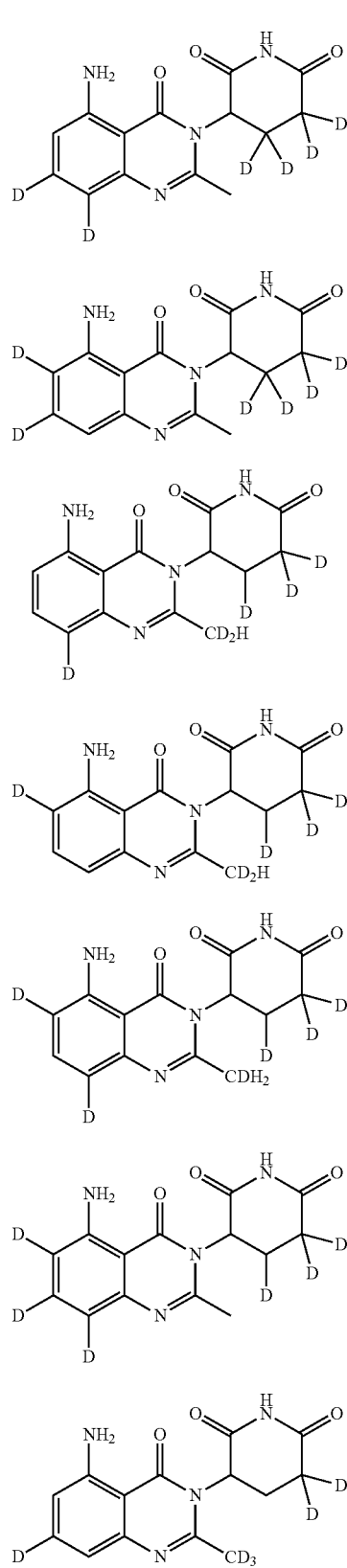

TABLE 1-continued
Deuterium enriched compounds of formula (I):
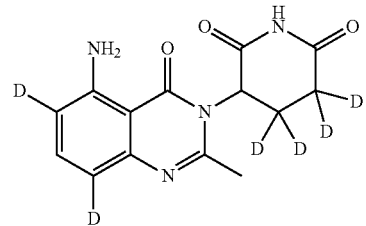 [SMILES: [2H]c1cc([2H])c2nc(C)n(C3C(=O)NC(=O)C([2H])([2H])C3([2H])[2H])c(=O)c2c1N]
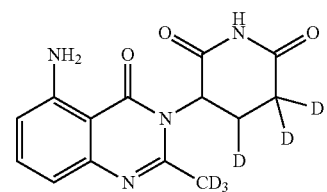 [SMILES: [2H]C1C(n2c(C([2H])([2H])[2H])nc3cccc(N)c3c2=O)C(=O)NC(=O)C1([2H])[2H]]
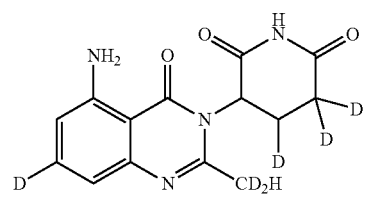
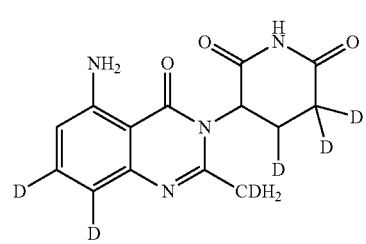
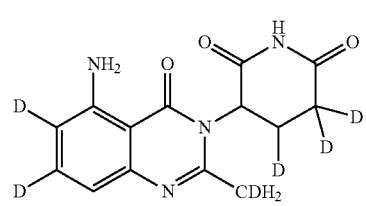
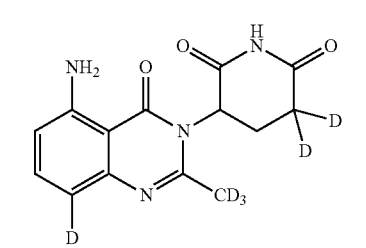 [SMILES: [2H]c1ccc(N)c2c(=O)n(C3CC([2H])([2H])C(=O)NC3=O)c(C([2H])([2H])[2H])nc12]
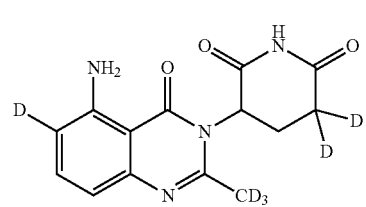 [SMILES: [2H]c1ccc2nc(C([2H])([2H])[2H])n(C3CC([2H])([2H])C(=O)NC3=O)c(=O)c2c1N]
TABLE 1-continued
Deuterium enriched compounds of formula (I):
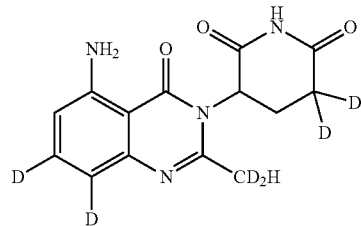
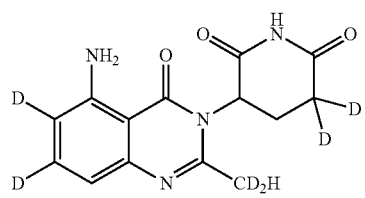
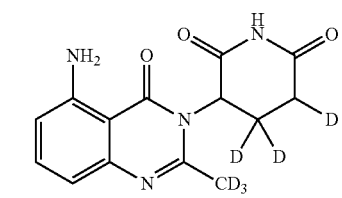 [SMILES: [2H]C1C(=O)NC(=O)C(n2c(C([2H])([2H])[2H])nc3cccc(N)c3c2=O)C1([2H])[2H]]
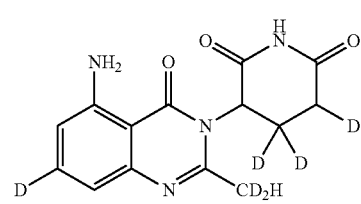
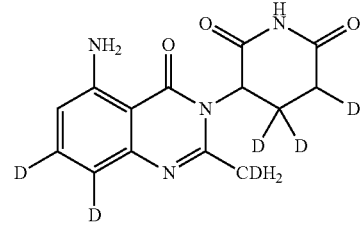
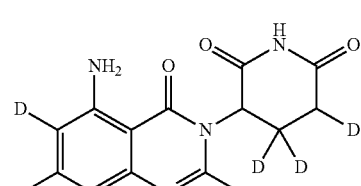
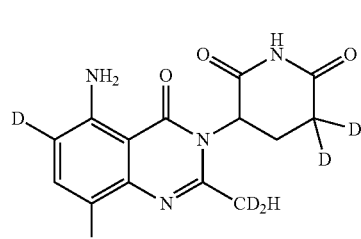

TABLE 1-continued
Deuterium enriched compounds of formula (I):
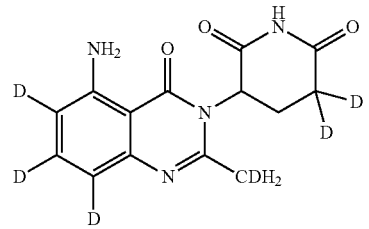
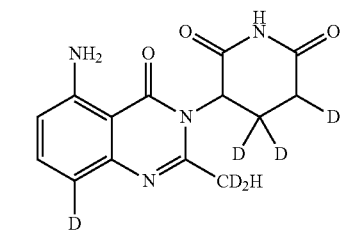
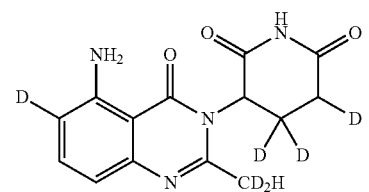
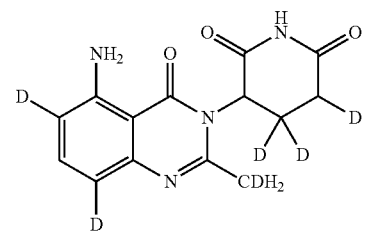
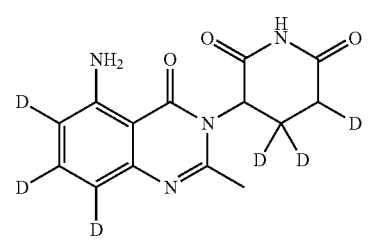 [SMILES: [2H]c1c([2H])c(N)c2c(=O)n(C3C(=O)NC(=O)C([2H])C3([2H])[2H])c(C)nc2c1[2H]]
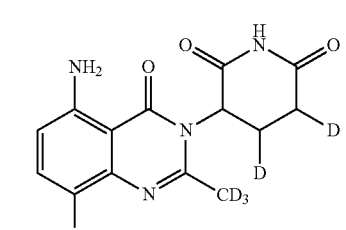
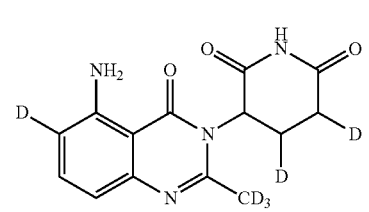 [SMILES: [2H]c1ccc2nc(C([2H])([2H])[2H])n(C3C(=O)NC(=O)C([2H])C3[2H])c(=O)c2c1N]
TABLE 1-continued
Deuterium enriched compounds of formula (I):
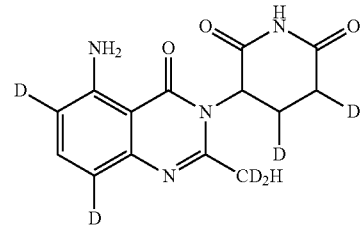
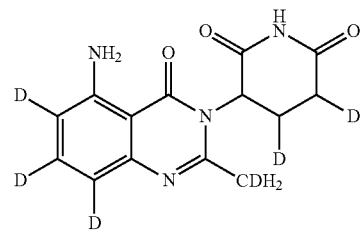
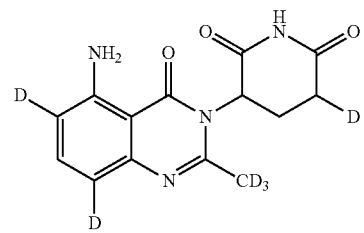 [SMILES: [2H]c1cc([2H])c2nc(C([2H])([2H])[2H])n(C3CC([2H])C(=O)NC3=O)c(=O)c2c1N]
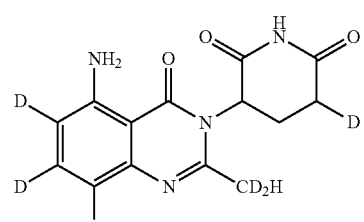
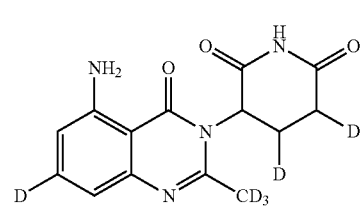
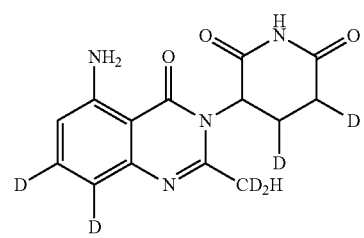
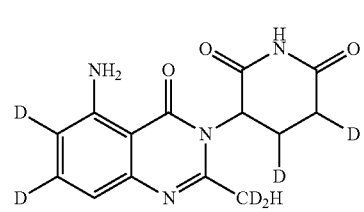

TABLE 1-continued
Deuterium enriched compounds of formula (I):
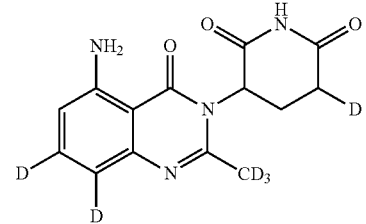 [SMILES: [2H]c1cc(N)c2c(=O)n(C3CC([2H])C(=O)NC3=O)c(C([2H])([2H])[2H])nc2c1[2H]]
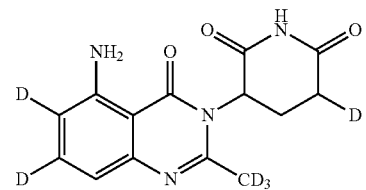 [SMILES: [2H]c1cc2nc(C([2H])([2H])[2H])n(C3CC([2H])C(=O)NC3=O)c(=O)c2c(N)c1[2H]]
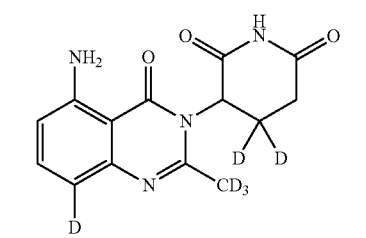 [SMILES: [2H]c1ccc(N)c2c(=O)n(C3C(=O)NC(=O)CC3([2H])[2H])c(C([2H])([2H])[2H])nc12]
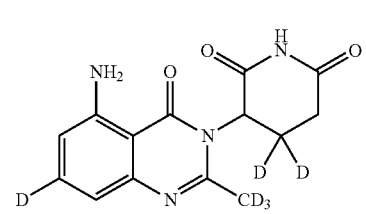
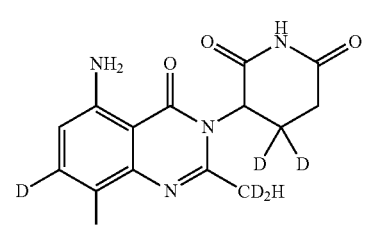
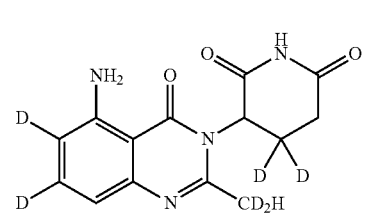
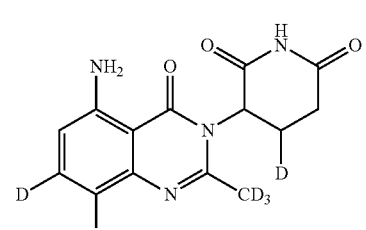
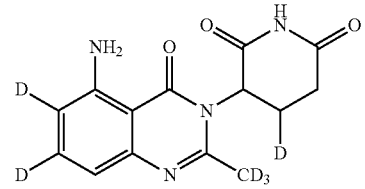
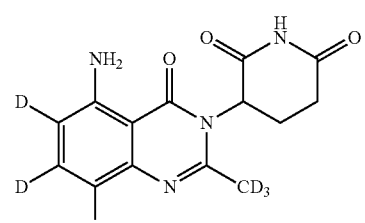
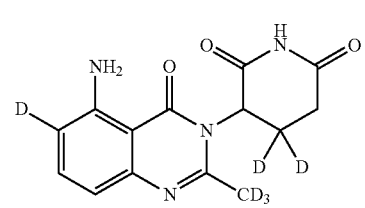 [SMILES: [2H]c1ccc2nc(C([2H])([2H])[2H])n(C3C(=O)NC(=O)CC3([2H])[2H])c(=O)c2c1N]
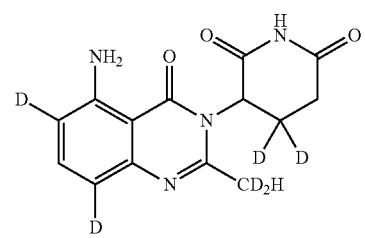
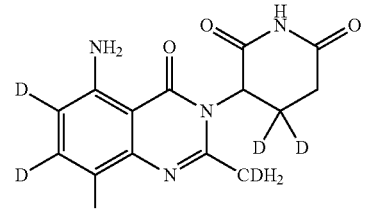
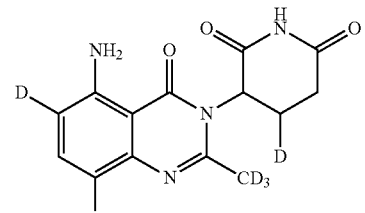
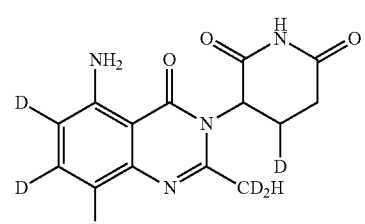

TABLE 1-continued
Deuterium enriched compounds of formula (I):
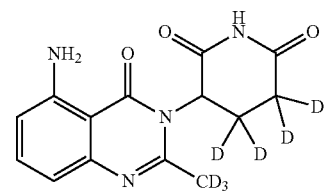 [SMILES: [2H]C([2H])([2H])c1nc2cccc(N)c2c(=O)n1C1C(=O)NC(=O)C([2H])([2H])C1([2H])[2H]]
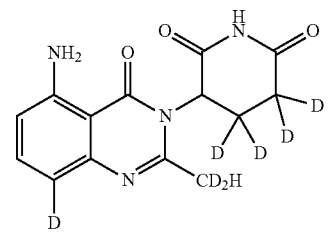
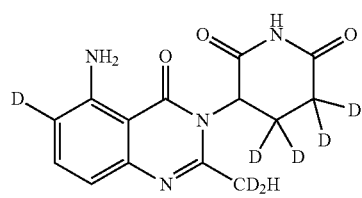
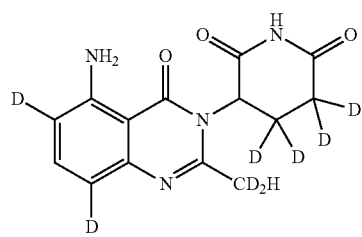
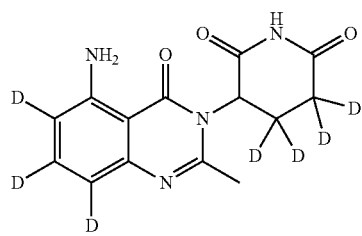 [SMILES: [2H]c1c([2H])c(N)c2c(=O)n(C3C(=O)NC(=O)C([2H])([2H])C3([2H])[2H])c(C)nc2c1[2H]]
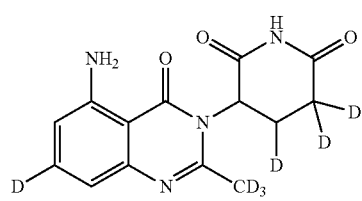 [SMILES: [2H]c1cc(N)c2c(=O)n(C3C(=O)NC(=O)C([2H])([2H])C3[2H])c(C([2H])([2H])[2H])nc2c1]
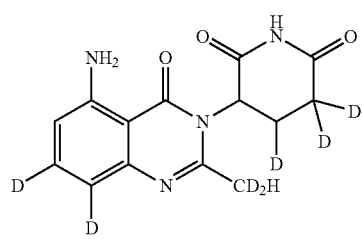
TABLE 1-continued
Deuterium enriched compounds of formula (I):
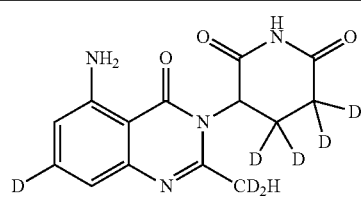
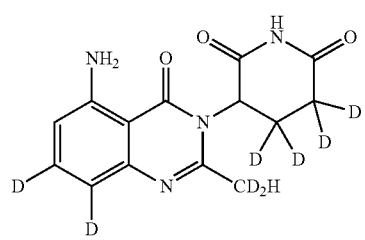
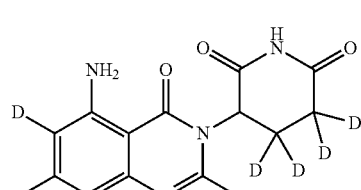
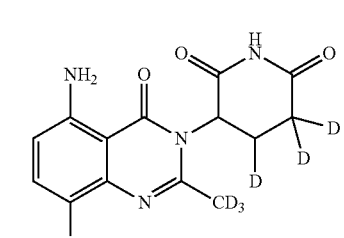
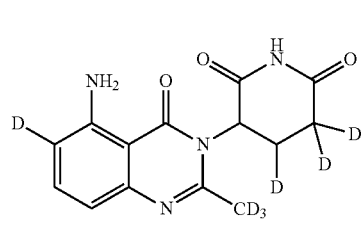
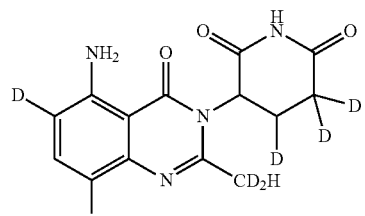
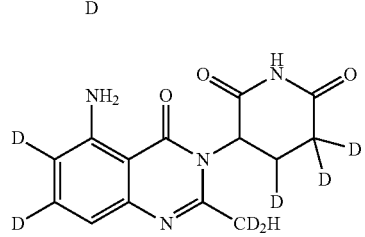

TABLE 1-continued
Deuterium enriched compounds of formula (I):
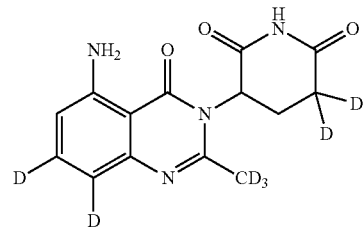 [SMILES: [2H]c1cc(N)c2c(=O)n(C3CC([2H])([2H])C(=O)NC3=O)c(C([2H])([2H])[2H])nc2c1[2H]]
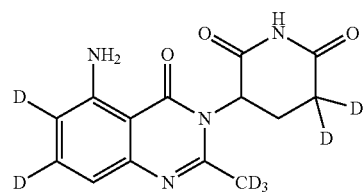
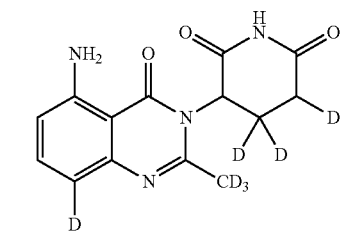 [SMILES: [2H]c1ccc(N)c2c(=O)n(C3C(=O)NC(=O)C([2H])C3([2H])[2H])c(C([2H])([2H])[2H])nc12]
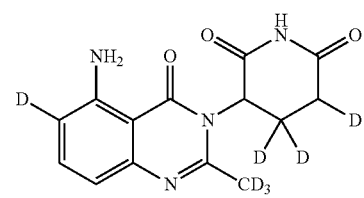 [SMILES: [2H]c1ccc2nc(C([2H])([2H])[2H])n(C3C(=O)NC(=O)C([2H])C3([2H])[2H])c(=O)c2c1N]
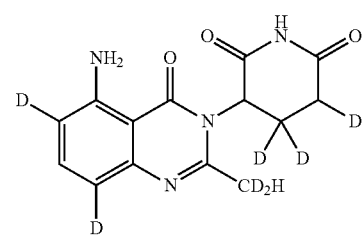
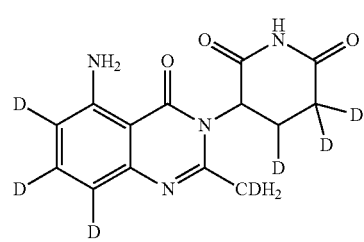
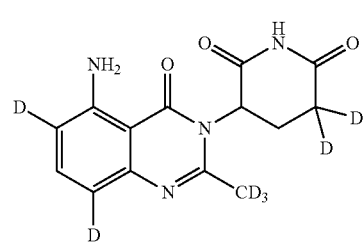 [SMILES: [2H]c1cc([2H])c2nc(C([2H])([2H])[2H])n(C3CC([2H])([2H])C(=O)NC3=O)c(=O)c2c1N]
TABLE 1-continued
Deuterium enriched compounds of formula (I):
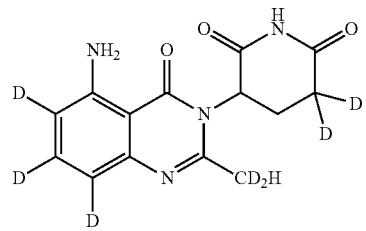
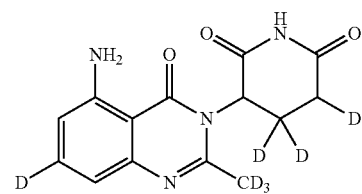 [SMILES: [2H]c1cc(N)c2c(=O)n(C3C(=O)NC(=O)C([2H])C3([2H])[2H])c(C([2H])([2H])[2H])nc2c1]
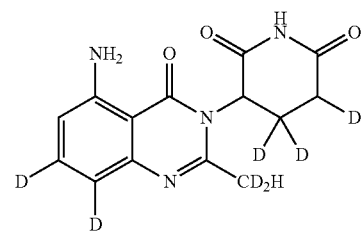
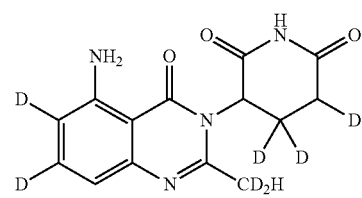
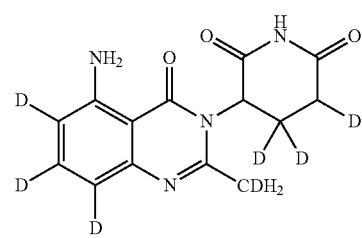
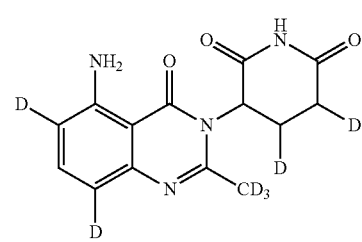 [SMILES: [2H]c1cc([2H])c2nc(C([2H])([2H])[2H])n(C3C(=O)NC(=O)C([2H])C3[2H])c(=O)c2c1N]
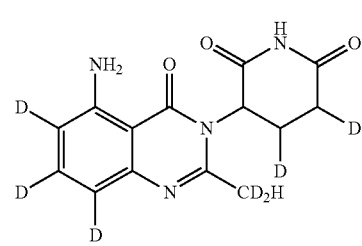

TABLE 1-continued

Deuterium enriched compounds of formula (I):

TABLE 1-continued
Deuterium enriched compounds of formula (I):
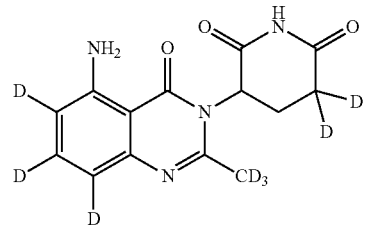 [SMILES: [2H]c1c([2H])c(N)c2c(=O)n(C3CC([2H])([2H])C(=O)NC3=O)c(C([2H])([2H])[2H])nc2c1[2H]]
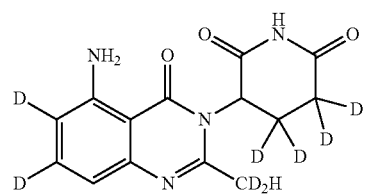
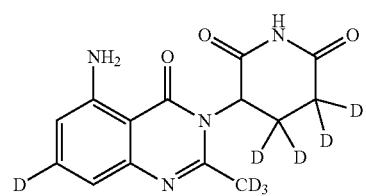
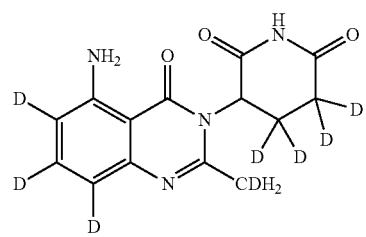
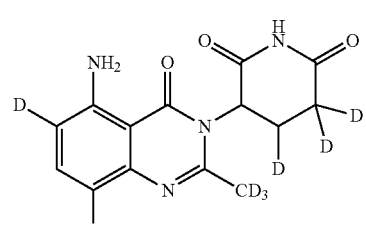
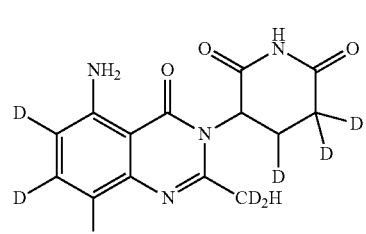
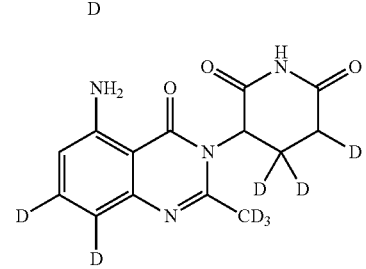
TABLE 1-continued
Deuterium enriched compounds of formula (I):
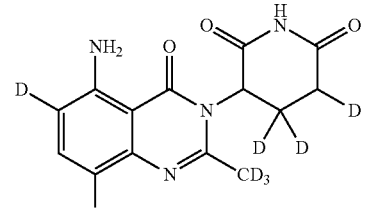
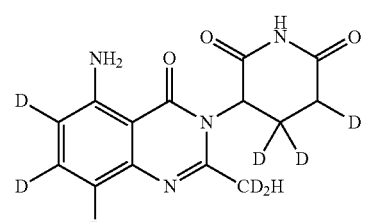
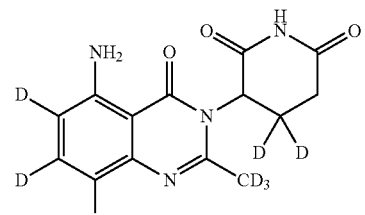
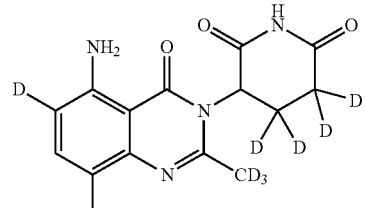
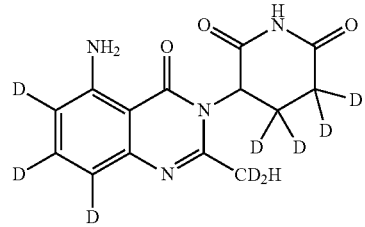
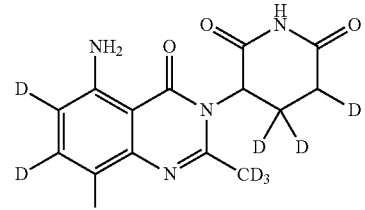

TABLE 1-continued
Deuterium enriched compounds of formula (I):
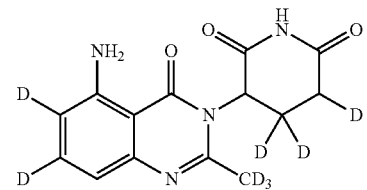
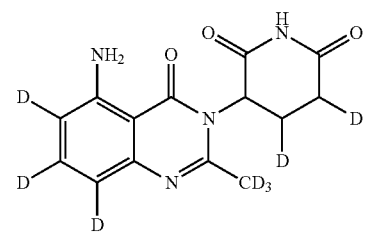 [SMILES: [2H]c1c([2H])c(N)c2c(=O)n(C3C(=O)NC(=O)C([2H])C3[2H])c(C([2H])([2H])[2H])nc2c1[2H]]
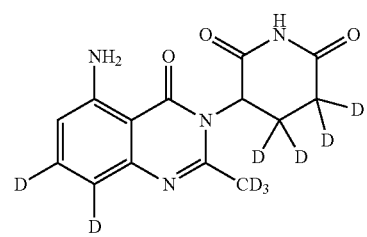 [SMILES: [2H]c1cc(N)c2c(=O)n(C3C(=O)NC(=O)C([2H])([2H])C3([2H])[2H])c(C([2H])([2H])[2H])nc2c1[2H]]
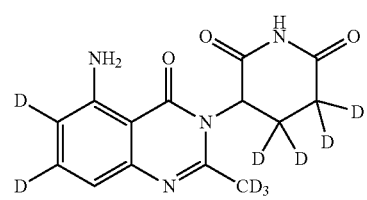
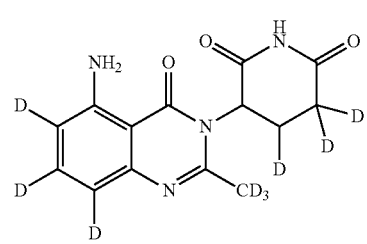 [SMILES: [2H]c1c([2H])c(N)c2c(=O)n(C3C(=O)NC(=O)C([2H])([2H])C3[2H])c(C([2H])([2H])[2H])nc2c1[2H]]
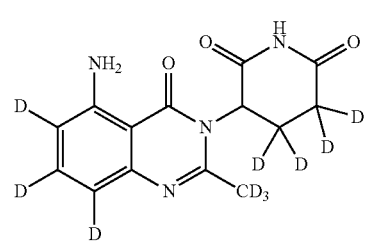 [SMILES: [2H]c1c([2H])c(N)c2c(=O)n(C3C(=O)NC(=O)C([2H])([2H])C3([2H])[2H])c(C([2H])([2H])[2H])nc2c1[2H]]
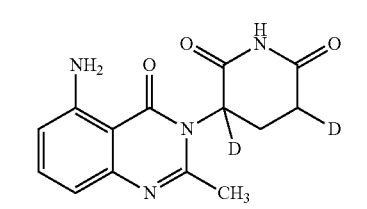 [SMILES: [2H]C1CC([2H])(n2c(C)nc3cccc(N)c3c2=O)C(=O)NC1=O]
TABLE 1-continued
Deuterium enriched compounds of formula (I):
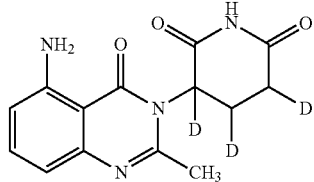
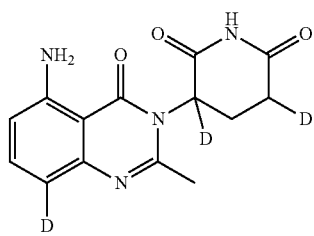 [SMILES: [2H]c1ccc(N)c2c(=O)n(C3([2H])CC([2H])C(=O)NC3=O)c(C)nc12]
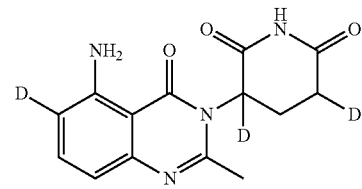 [SMILES: [2H]c1ccc2nc(C)n(C3([2H])CC([2H])C(=O)NC3=O)c(=O)c2c1N]
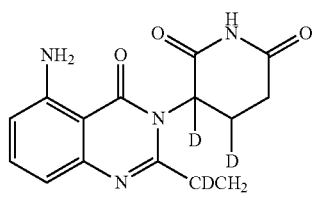
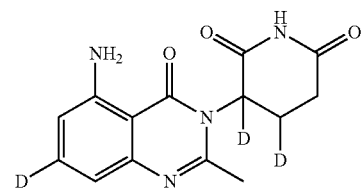 [SMILES: [2H]c1cc(N)c2c(=O)n(C3([2H])C(=O)NC(=O)CC3[2H])c(C)nc2c1]
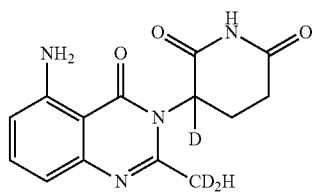
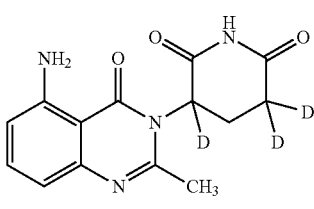 [SMILES: [2H]C1([2H])CC([2H])(n2c(C)nc3cccc(N)c3c2=O)C(=O)NC1=O]

TABLE 1-continued

Deuterium enriched compounds of formula (I):

TABLE 1-continued
Deuterium enriched compounds of formula (I):
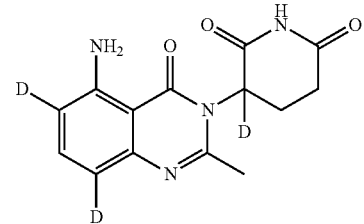 [SMILES: [2H]c1cc([2H])c2nc(C)n(C3([2H])CCC(=O)NC3=O)c(=O)c2c1N]
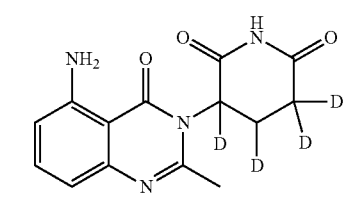 [SMILES: [2H]C1C([2H])([2H])C(=O)NC(=O)C1([2H])n1c(C)nc2cccc(N)c2c1=O]
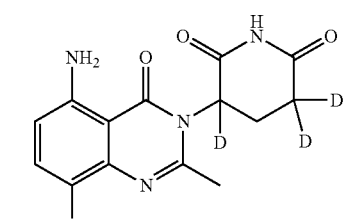
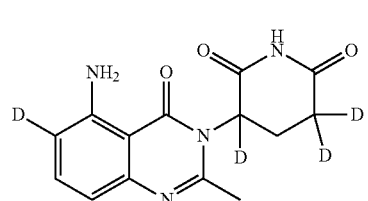
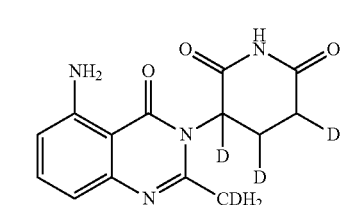
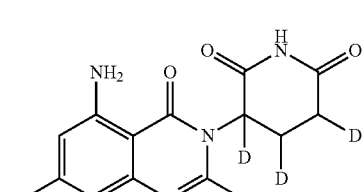
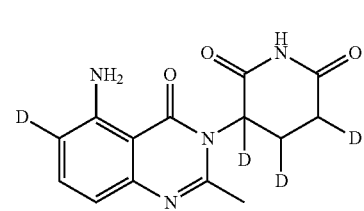 [SMILES: [2H]c1ccc2nc(C)n(C3([2H])C(=O)NC(=O)C([2H])C3[2H])c(=O)c2c1N]
TABLE 1-continued
Deuterium enriched compounds of formula (I):
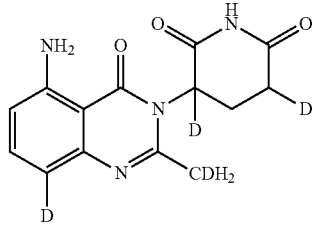
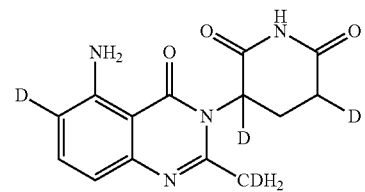
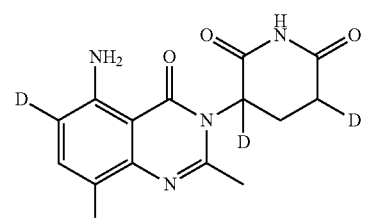
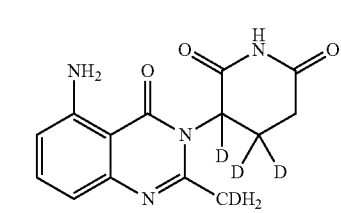
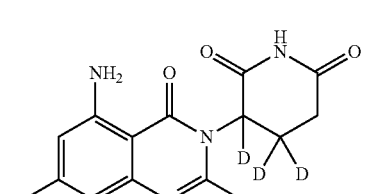
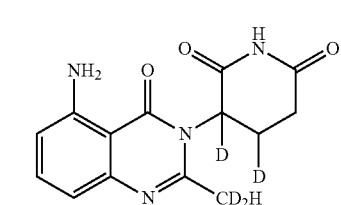
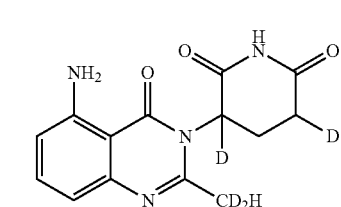

TABLE 1-continued
Deuterium enriched compounds of formula (I):
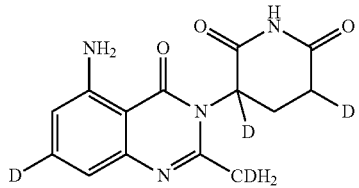
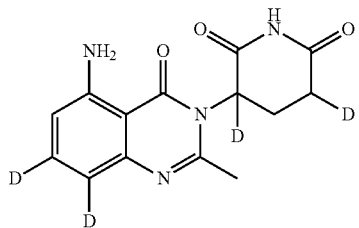 [SMILES: [2H]c1cc(N)c2c(=O)n(C3([2H])CC([2H])C(=O)NC3=O)c(C)nc2c1[2H]]
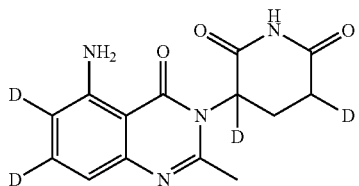 [SMILES: [2H]c1cc2nc(C)n(C3([2H])CC([2H])C(=O)NC3=O)c(=O)c2c(N)c1[2H]]
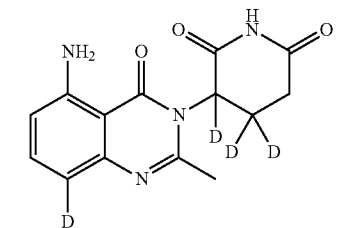 [SMILES: [2H]c1ccc(N)c2c(=O)n(C3([2H])C(=O)NC(=O)CC3([2H])[2H])c(C)nc12]
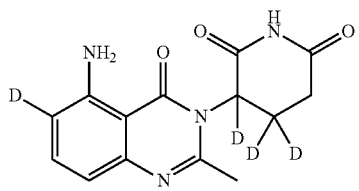 [SMILES: [2H]c1ccc2nc(C)n(C3([2H])C(=O)NC(=O)CC3([2H])[2H])c(=O)c2c1N]
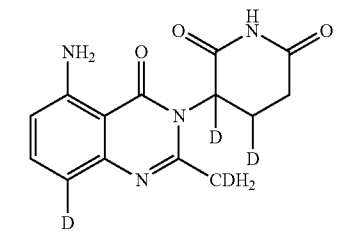
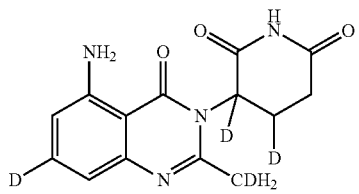
TABLE 1-continued
Deuterium enriched compounds of formula (I):
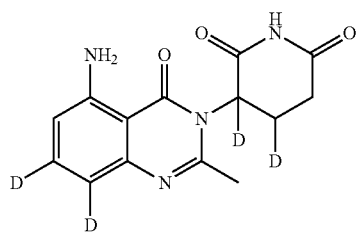 [SMILES: [2H]c1cc(N)c2c(=O)n(C3([2H])C(=O)NC(=O)CC3[2H])c(C)nc2c1[2H]]
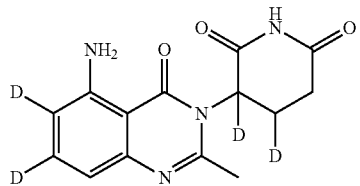 [SMILES: [2H]c1cc2nc(C)n(C3([2H])C(=O)NC(=O)CC3[2H])c(=O)c2c(N)c1[2H]]
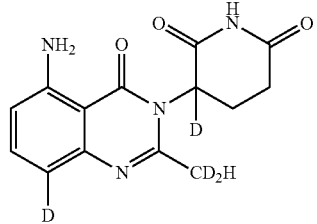
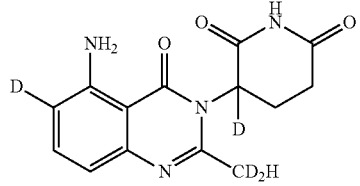
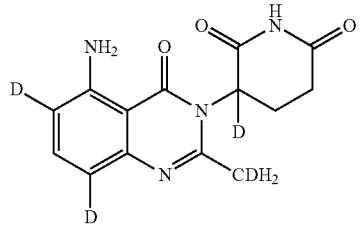
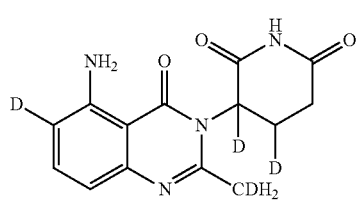
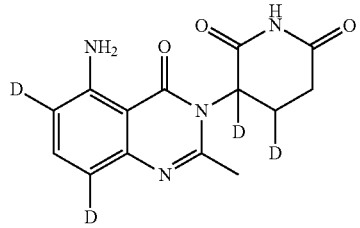

TABLE 1-continued
Deuterium enriched compounds of formula (I):
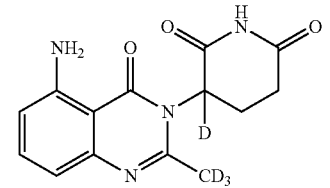
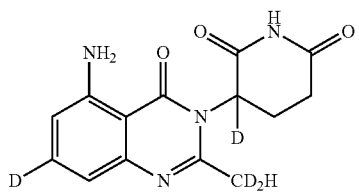
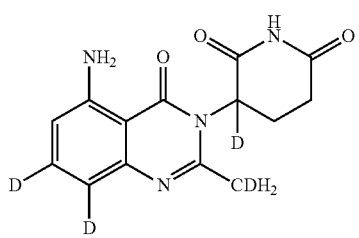
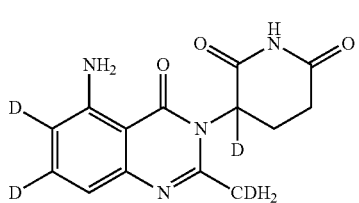
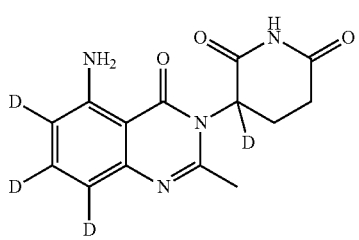 [SMILES: [2H]c1c([2H])c(N)c2c(=O)n(C3([2H])CCC(=O)NC3=O)c(C)nc2c1[2H]]
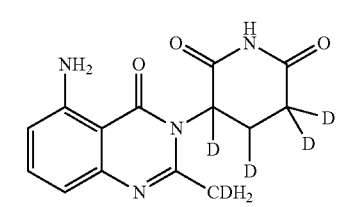
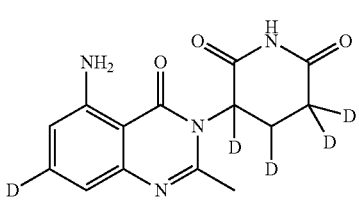 [SMILES: [2H]c1cc(N)c2c(=O)n(C3([2H])C(=O)NC(=O)C([2H])([2H])C3[2H])c(C)nc2c1]
TABLE 1-continued
Deuterium enriched compounds of formula (I):
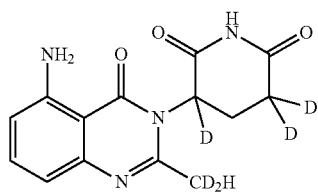
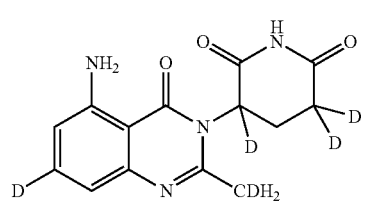
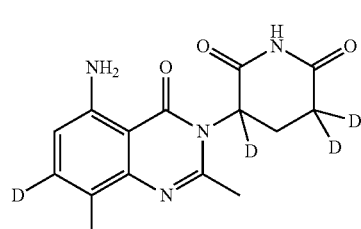
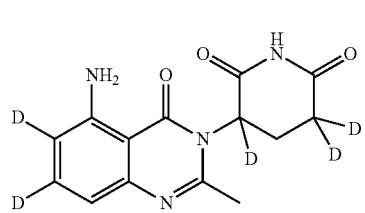 [SMILES: [2H]c1cc2nc(C)n(C3([2H])CC([2H])([2H])C(=O)NC3=O)c(=O)c2c(N)c1[2H]]
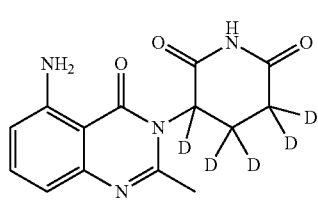 [SMILES: [2H]C1([2H])C(=O)NC(=O)C([2H])(n2c(C)nc3cccc(N)c3c2=O)C1([2H])[2H]]
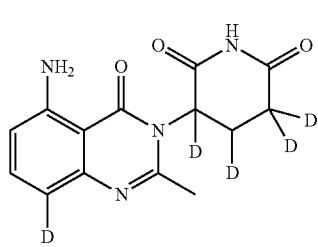 [SMILES: [2H]c1ccc(N)c2c(=O)n(C3([2H])C(=O)NC(=O)C([2H])([2H])C3[2H])c(C)nc12]
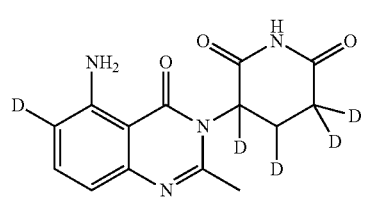 [SMILES: [2H]c1ccc2nc(C)n(C3([2H])C(=O)NC(=O)C([2H])([2H])C3[2H])c(=O)c2c1N]

TABLE 1-continued
Deuterium enriched compounds of formula (I):
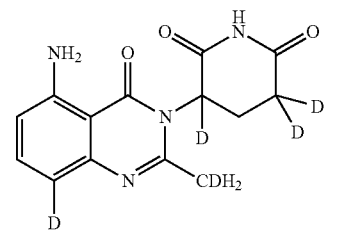
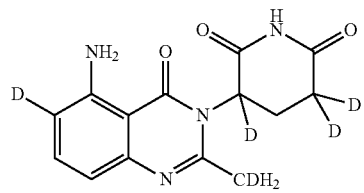
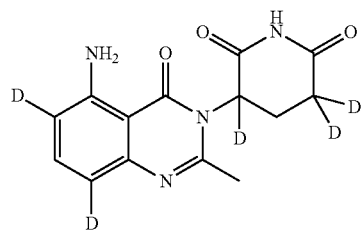 [SMILES: [2H]c1cc([2H])c2nc(C)n(C3([2H])CC([2H])([2H])C(=O)NC3=O)c(=O)c2c1N]
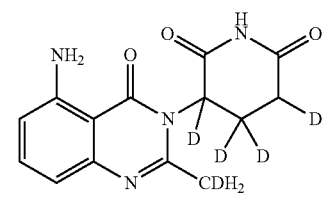
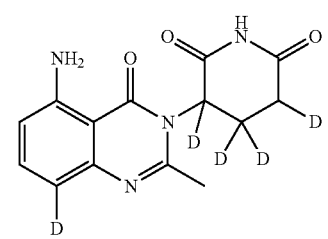 [SMILES: [2H]c1ccc(N)c2c(=O)n(C3([2H])C(=O)NC(=O)C([2H])C3([2H])[2H])c(C)nc12]
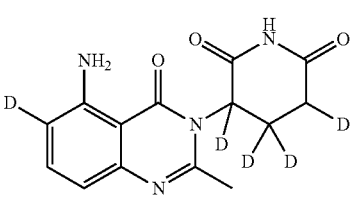 [SMILES: [2H]c1ccc2nc(C)n(C3([2H])C(=O)NC(=O)C([2H])C3([2H])[2H])c(=O)c2c1N]
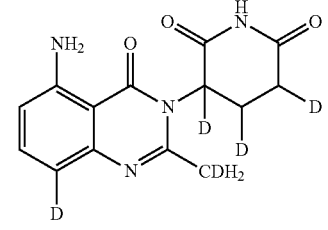
TABLE 1-continued
Deuterium enriched compounds of formula (I):
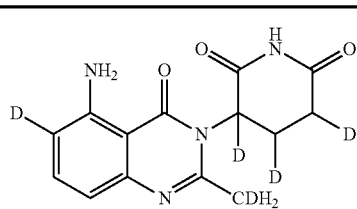
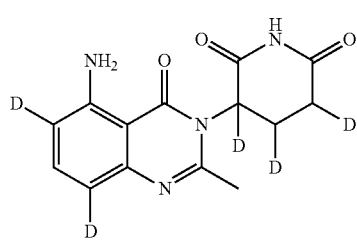 [SMILES: [2H]c1cc([2H])c2nc(C)n(C3([2H])C(=O)NC(=O)C([2H])C3[2H])c(=O)c2c1N]
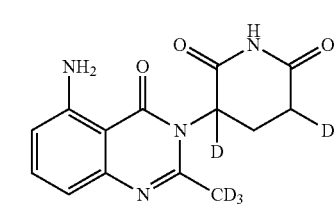 [SMILES: [2H]C1CC([2H])(n2c(C([2H])([2H])[2H])nc3cccc(N)c3c2=O)C(=O)NC1=O]
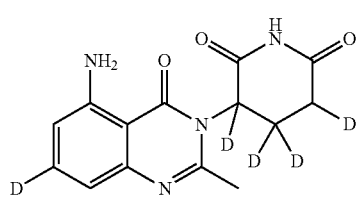 [SMILES: [2H]c1cc(N)c2c(=O)n(C3([2H])C(=O)NC(=O)C([2H])C3([2H])[2H])c(C)nc2c1]
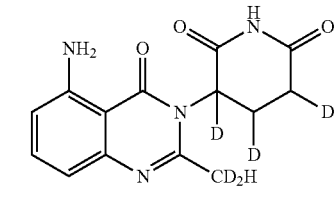
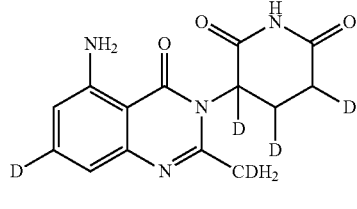
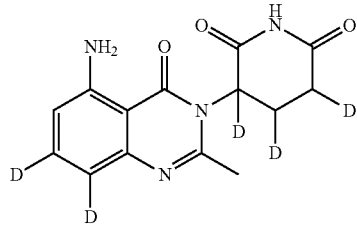 [SMILES: [2H]c1cc(N)c2c(=O)n(C3([2H])C(=O)NC(=O)C([2H])C3[2H])c(C)nc2c1[2H]]

TABLE 1-continued
Deuterium enriched compounds of formula (I):
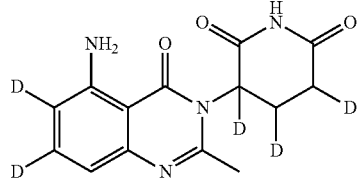 [SMILES: [2H]c1cc2nc(C)n(C3([2H])C(=O)NC(=O)C([2H])C3[2H])c(=O)c2c(N)c1[2H]]
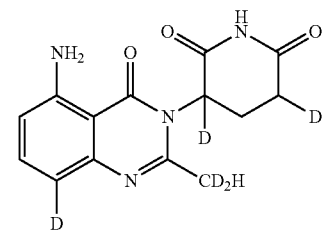
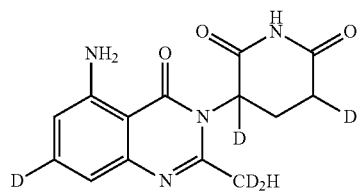
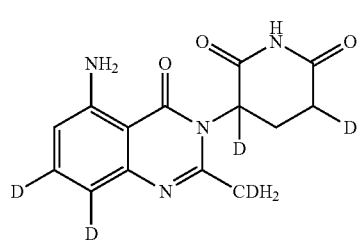
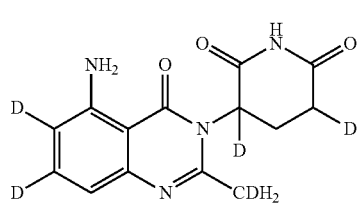
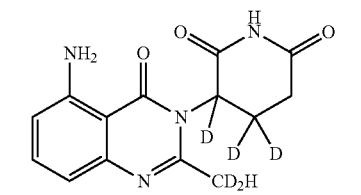
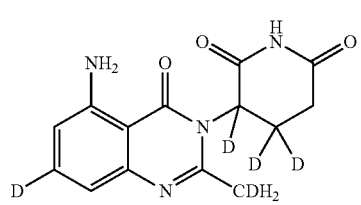
TABLE 1-continued
Deuterium enriched compounds of formula (I):
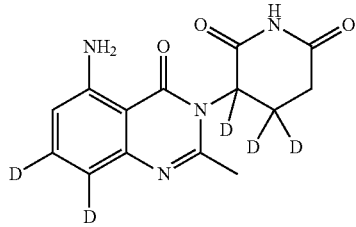 [SMILES: [2H]c1cc(N)c2c(=O)n(C3([2H])C(=O)NC(=O)CC3([2H])[2H])c(C)nc2c1[2H]]
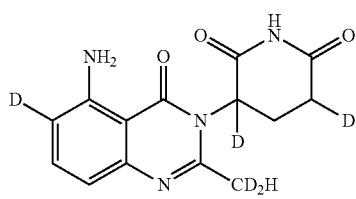
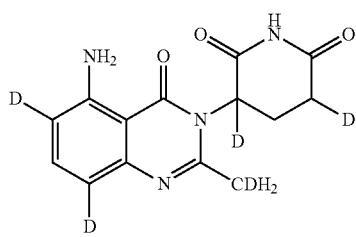
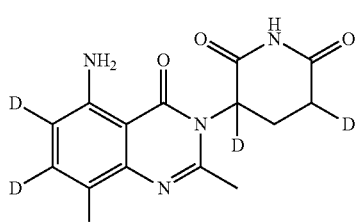
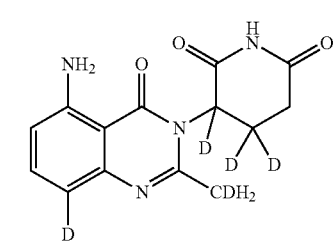
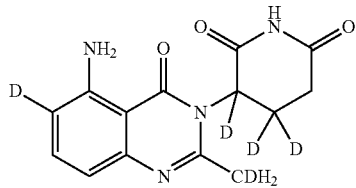
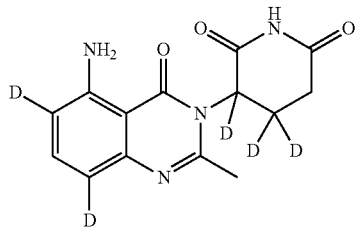

TABLE 1-continued
Deuterium enriched compounds of formula (I):
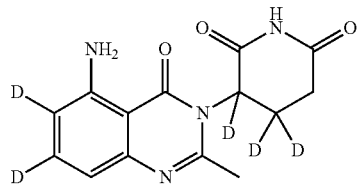 [SMILES: [2H]c1cc2nc(C)n(C3([2H])C(=O)NC(=O)CC3([2H])[2H])c(=O)c2c(N)c1[2H]]
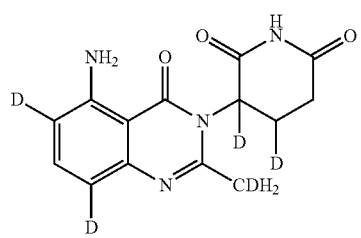
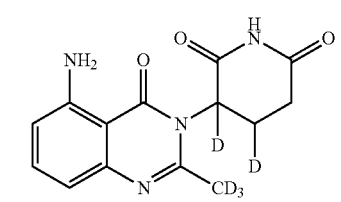
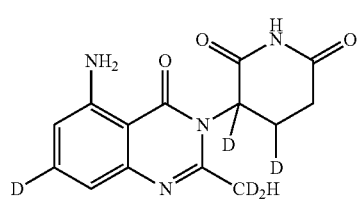
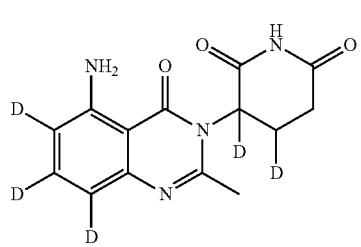 [SMILES: [2H]c1c([2H])c(N)c2c(=O)n(C3([2H])C(=O)NC(=O)CC3[2H])c(C)nc2c1[2H]]
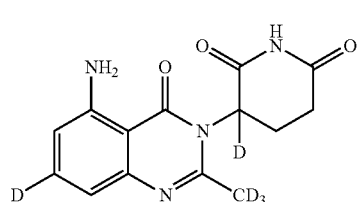
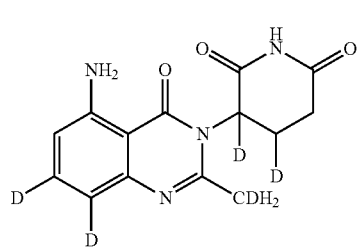
TABLE 1-continued
Deuterium enriched compounds of formula (I):
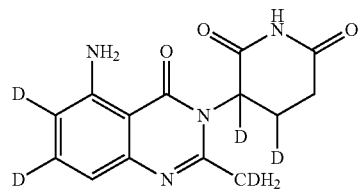
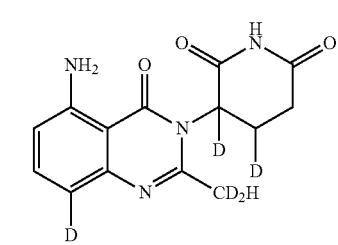
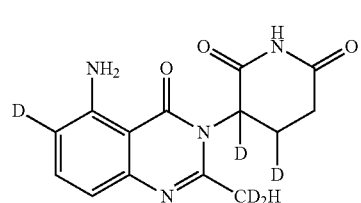
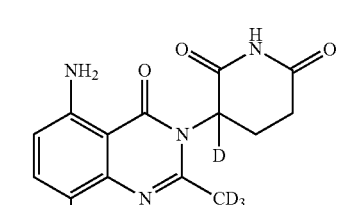
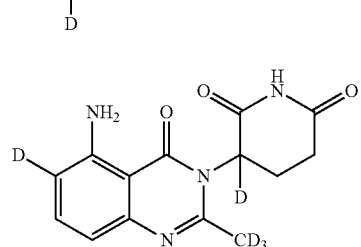
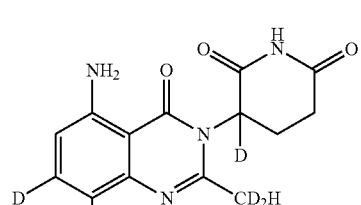
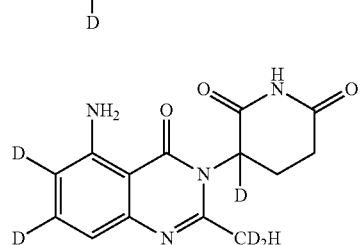

TABLE 1-continued
Deuterium enriched compounds of formula (I):
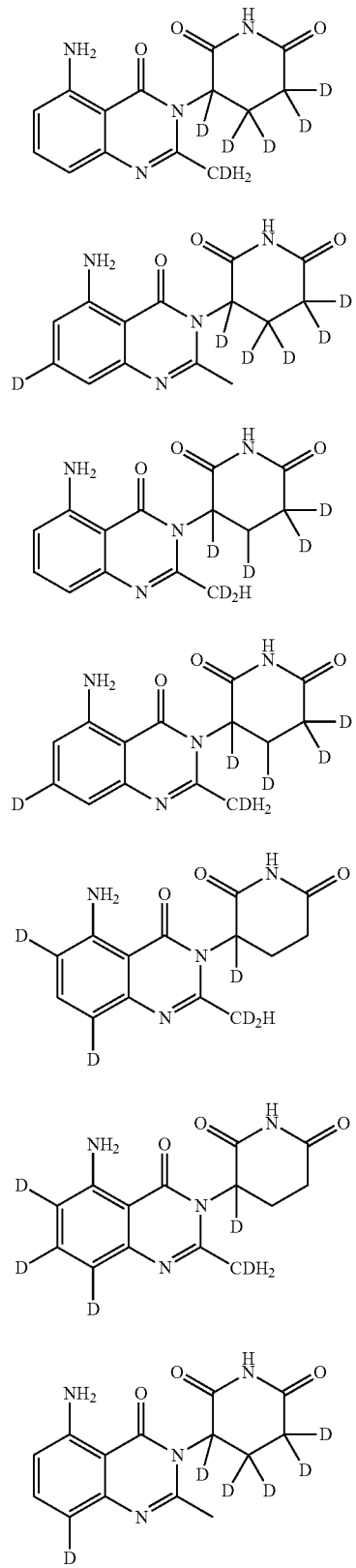
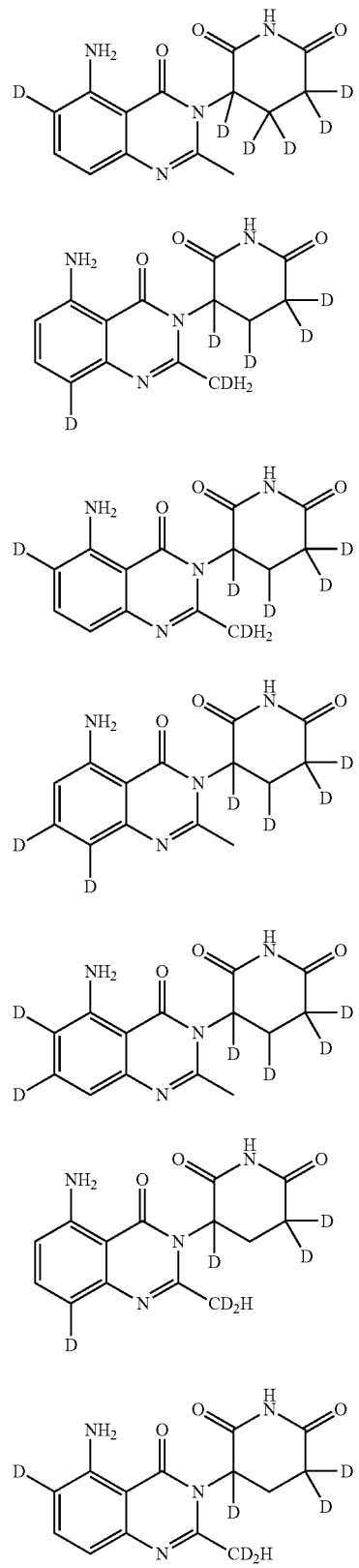

TABLE 1-continued

Deuterium enriched compounds of formula (I):

TABLE 1-continued
Deuterium enriched compounds of formula (I):
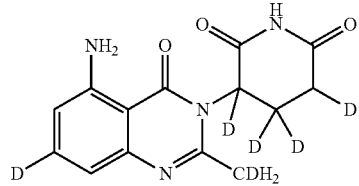
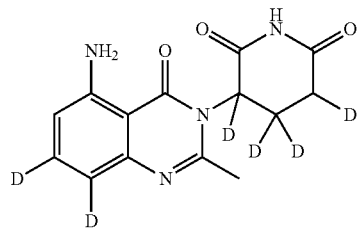 [SMILES: [2H]c1cc(N)c2c(=O)n(C3([2H])C(=O)NC(=O)C([2H])C3([2H])[2H])c(C)nc2c1[2H]]
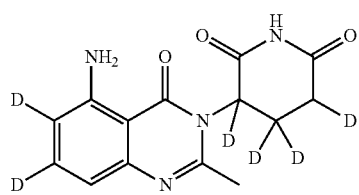 [SMILES: [2H]c1cc2nc(C)n(C3([2H])C(=O)NC(=O)C([2H])C3([2H])[2H])c(=O)c2c(N)c1[2H]]
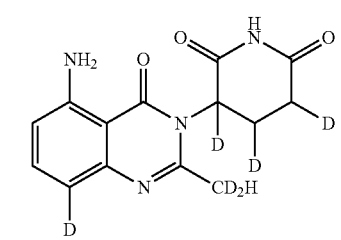
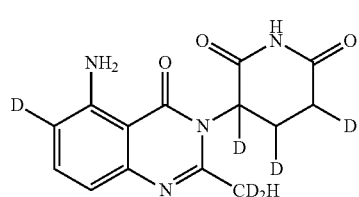
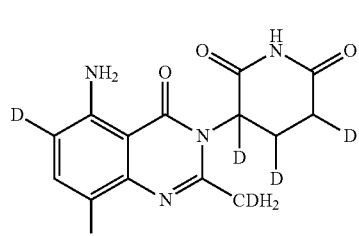
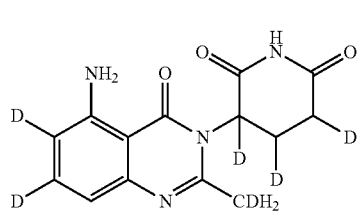
TABLE 1-continued
Deuterium enriched compounds of formula (I):
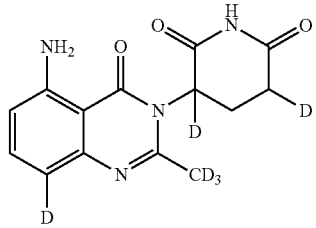 [SMILES: [2H]c1ccc(N)c2c(=O)n(C3([2H])CC([2H])C(=O)NC3=O)c(C([2H])([2H])[2H])nc12]
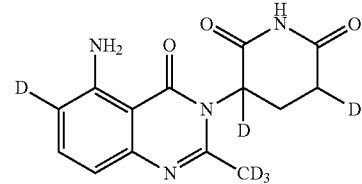 [SMILES: [2H]c1ccc2nc(C([2H])([2H])[2H])n(C3([2H])CC([2H])C(=O)NC3=O)c(=O)c2c1N]
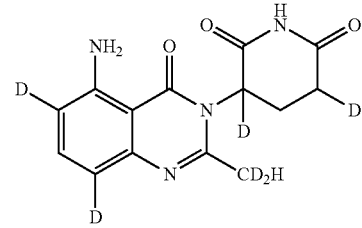
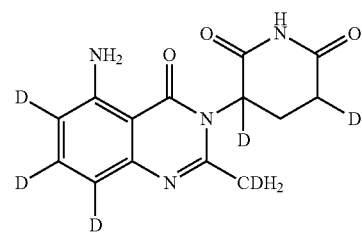
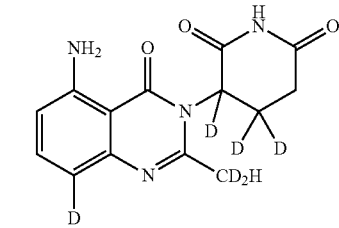
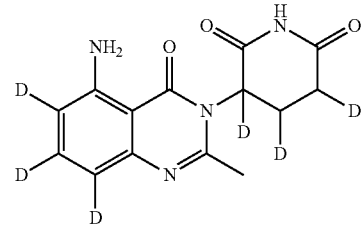 [SMILES: [2H]c1c([2H])c(N)c2c(=O)n(C3([2H])C(=O)NC(=O)C([2H])C3[2H])c(C)nc2c1[2H]]
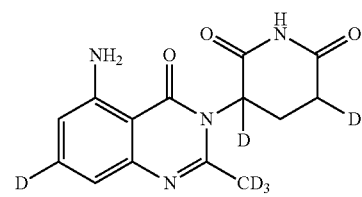 [SMILES: [2H]c1cc(N)c2c(=O)n(C3([2H])CC([2H])C(=O)NC3=O)c(C([2H])([2H])[2H])nc2c1]

TABLE 1-continued
Deuterium enriched compounds of formula (I):
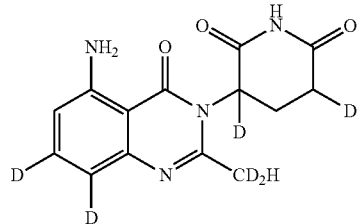
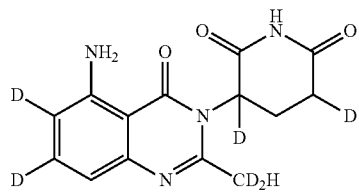
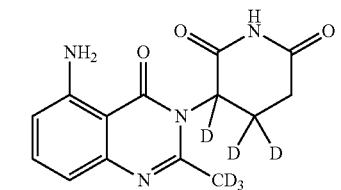 [SMILES: [2H]C([2H])([2H])c1nc2cccc(N)c2c(=O)n1C1([2H])C(=O)NC(=O)CC1([2H])[2H]]
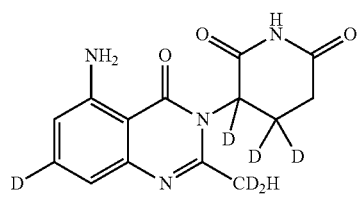
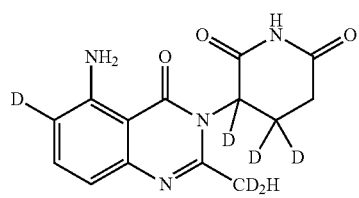
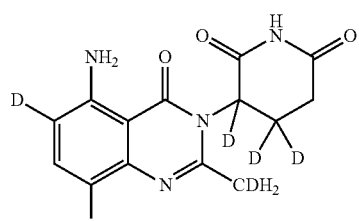
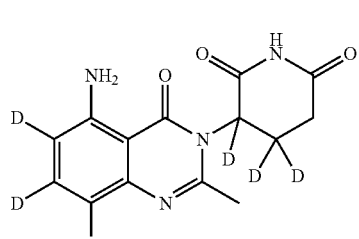
TABLE 1-continued
Deuterium enriched compounds of formula (I):
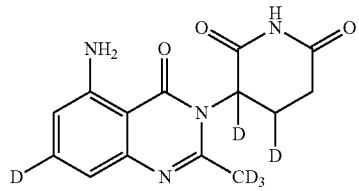
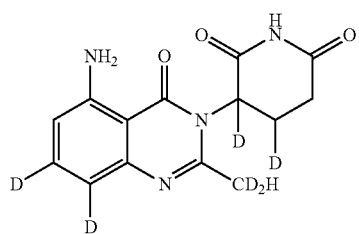
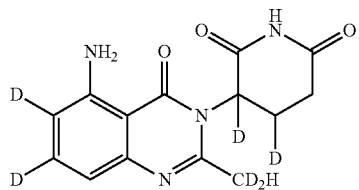
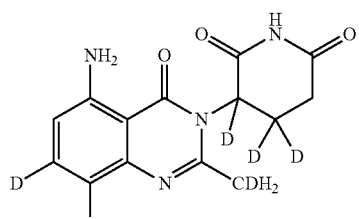
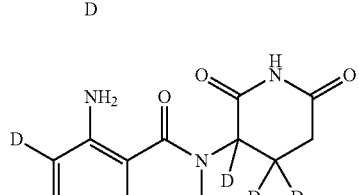
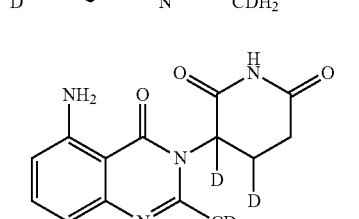
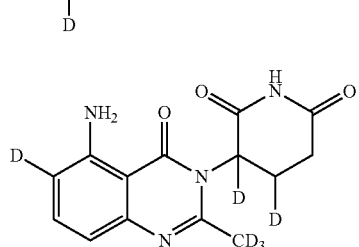

TABLE 1-continued
Deuterium enriched compounds of formula (I):
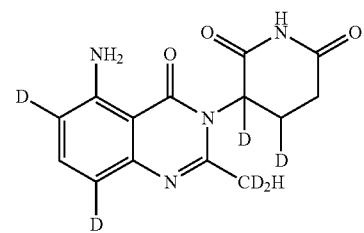
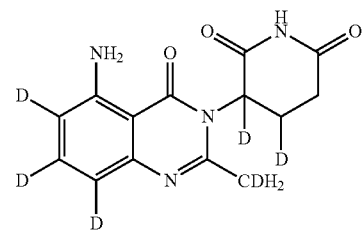
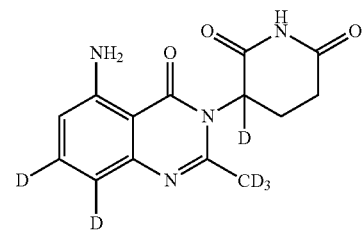
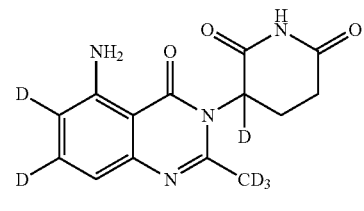
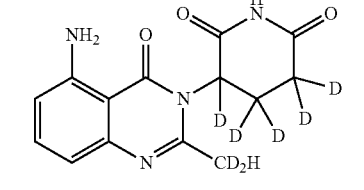
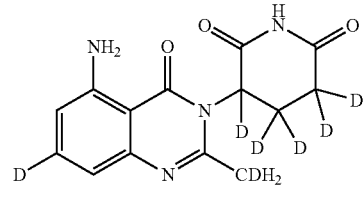
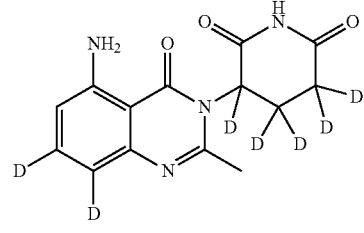 [SMILES: [2H]c1cc(N)c2c(=O)n(C3([2H])C(=O)NC(=O)C([2H])([2H])C3([2H])[2H])c(C)nc2c1[2H]]
TABLE 1-continued
Deuterium enriched compounds of formula (I):
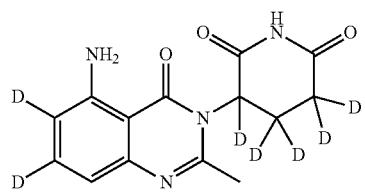 [SMILES: [2H]c1cc2nc(C)n(C3([2H])C(=O)NC(=O)C([2H])([2H])C3([2H])[2H])c(=O)c2c(N)c1[2H]]
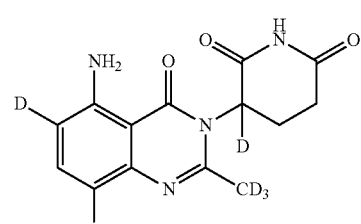
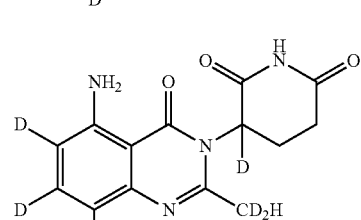
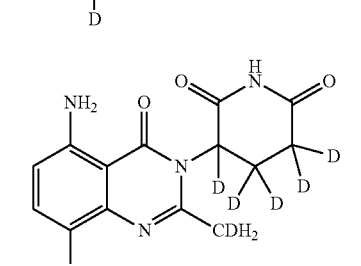
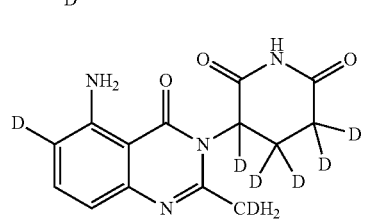
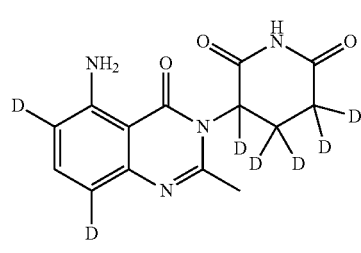 [SMILES: [2H]c1cc([2H])c2nc(C)n(C3([2H])C(=O)NC(=O)C([2H])([2H])C3([2H])[2H])c(=O)c2c1N]
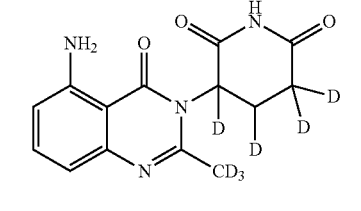 [SMILES: [2H]C1C([2H])([2H])C(=O)NC(=O)C1([2H])n1c(C([2H])([2H])[2H])nc2cccc(N)c2c1=O]

TABLE 1-continued
Deuterium enriched compounds of formula (I):
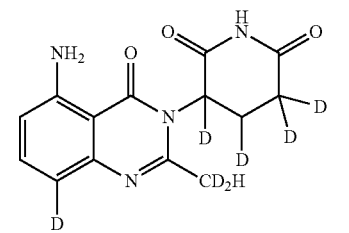
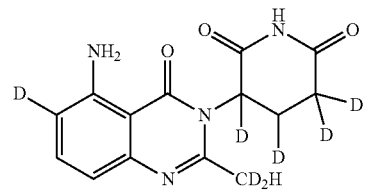
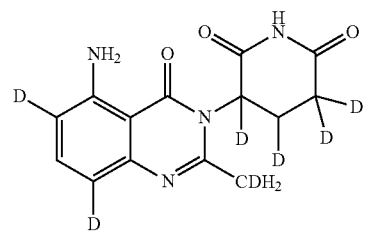
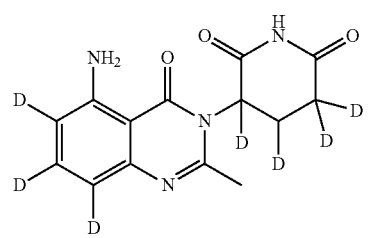 [SMILES: [2H]c1c([2H])c(N)c2c(=O)n(C3([2H])C(=O)NC(=O)C([2H])([2H])C3[2H])c(C)nc2c1[2H]]
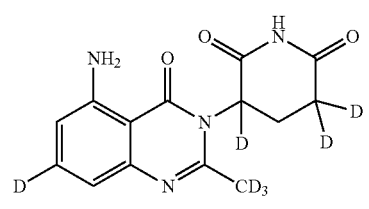 [SMILES: [2H]c1cc(N)c2c(=O)n(C3([2H])CC([2H])([2H])C(=O)NC3=O)c(C([2H])([2H])[2H])nc2c1]
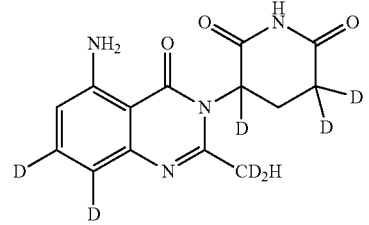
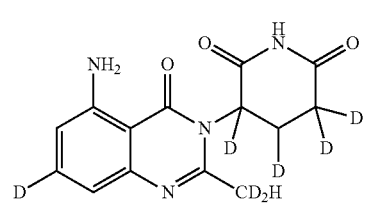
TABLE 1-continued
Deuterium enriched compounds of formula (I):
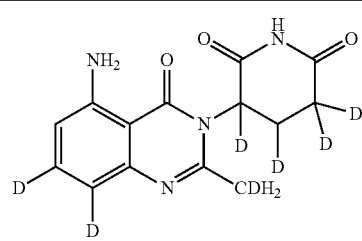
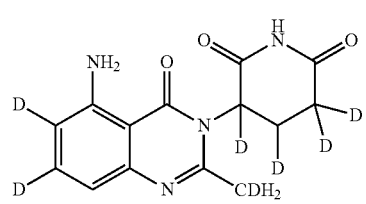
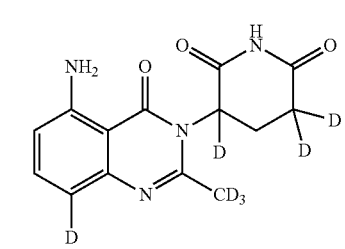 [SMILES: [2H]c1ccc(N)c2c(=O)n(C3([2H])CC([2H])([2H])C(=O)NC3=O)c(C([2H])([2H])[2H])nc12]
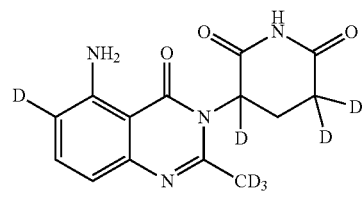 [SMILES: [2H]c1ccc2nc(C([2H])([2H])[2H])n(C3([2H])CC([2H])([2H])C(=O)NC3=O)c(=O)c2c1N]
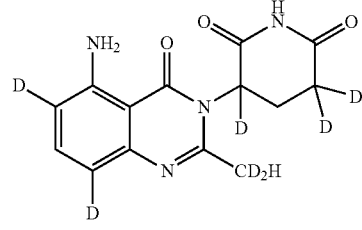
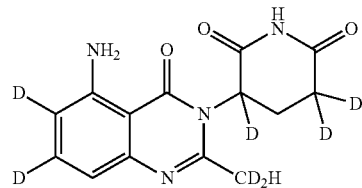
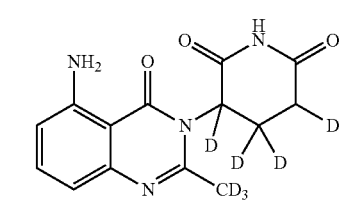 [SMILES: [2H]C1C(=O)NC(=O)C([2H])(n2c(C([2H])([2H])[2H])nc3cccc(N)c3c2=O)C1([2H])[2H]]

TABLE 1-continued

Deuterium enriched compounds of formula (I):

TABLE 1-continued

Deuterium enriched compounds of formula (I):

TABLE 1-continued
Deuterium enriched compounds of formula (I):
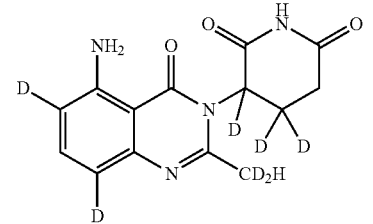
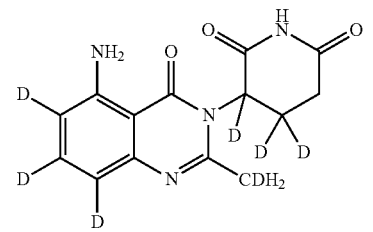
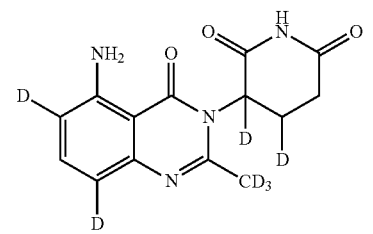 [SMILES: [2H]c1cc([2H])c2nc(C([2H])([2H])[2H])n(C3([2H])C(=O)NC(=O)CC3[2H])c(=O)c2c1N]
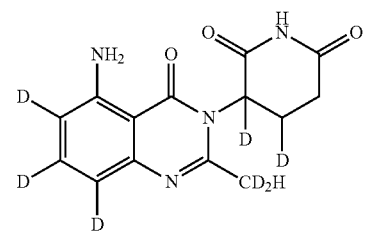
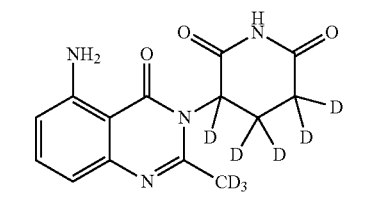 [SMILES: [2H]C([2H])([2H])c1nc2cccc(N)c2c(=O)n1C1([2H])C(=O)NC(=O)C([2H])([2H])C1([2H])[2H]]
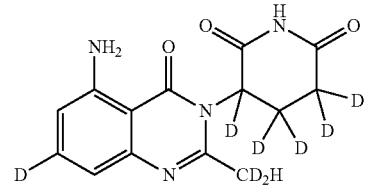
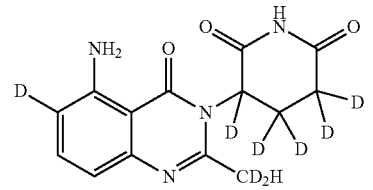
TABLE 1-continued
Deuterium enriched compounds of formula (I):
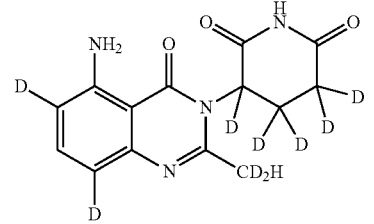
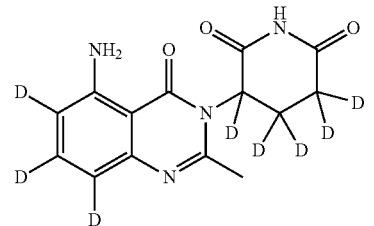 [SMILES: [2H]c1c([2H])c(N)c2c(=O)n(C3([2H])C(=O)NC(=O)C([2H])([2H])C3([2H])[2H])c(C)nc2c1[2H]]
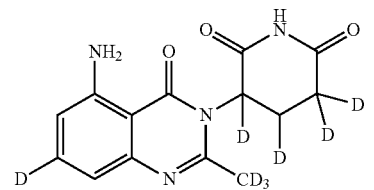 [SMILES: [2H]c1cc(N)c2c(=O)n(C3([2H])C(=O)NC(=O)C([2H])([2H])C3[2H])c(C([2H])([2H])[2H])nc2c1]
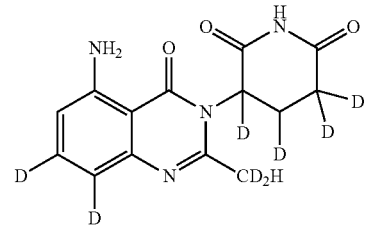
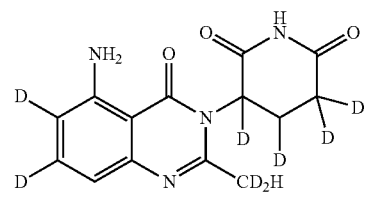
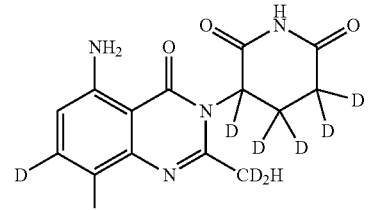
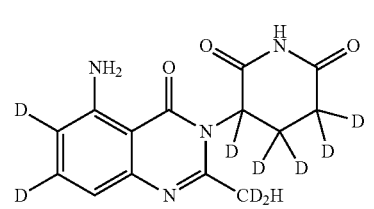

TABLE 1-continued
Deuterium enriched compounds of formula (I):
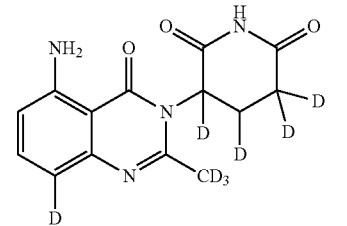 [SMILES: [2H]c1ccc(N)c2c(=O)n(C3([2H])C(=O)NC(=O)C([2H])([2H])C3[2H])c(C([2H])([2H])[2H])nc12]
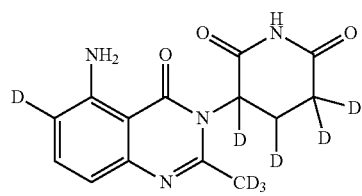 [SMILES: [2H]c1ccc2nc(C([2H])([2H])[2H])n(C3([2H])C(=O)NC(=O)C([2H])([2H])C3[2H])c(=O)c2c1N]
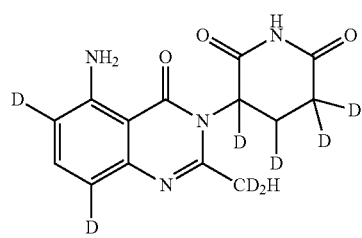
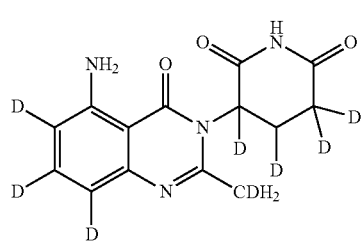
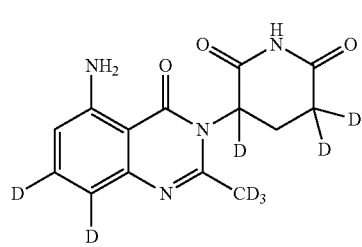 [SMILES: [2H]c1cc(N)c2c(=O)n(C3([2H])CC([2H])([2H])C(=O)NC3=O)c(C([2H])([2H])[2H])nc2c1[2H]]
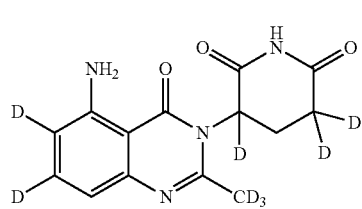 [SMILES: [2H]c1cc2nc(C([2H])([2H])[2H])n(C3([2H])CC([2H])([2H])C(=O)NC3=O)c(=O)c2c(N)c1[2H]]
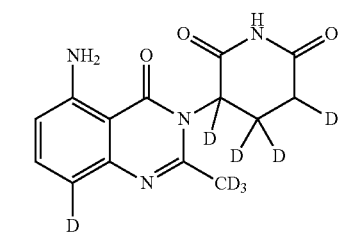 [SMILES: [2H]c1ccc(N)c2c(=O)n(C3([2H])C(=O)NC(=O)C([2H])C3([2H])[2H])c(C([2H])([2H])[2H])nc12]
TABLE 1-continued
Deuterium enriched compounds of formula (I):
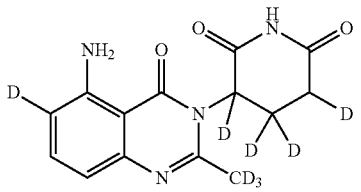
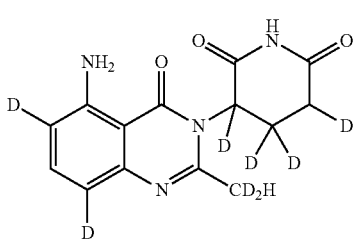
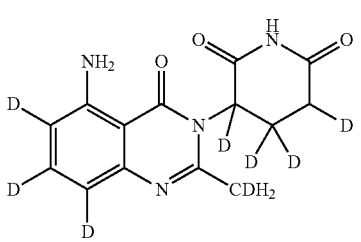
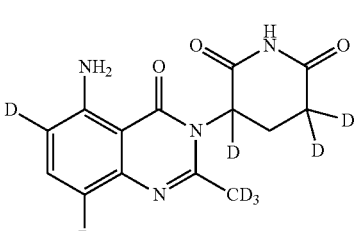
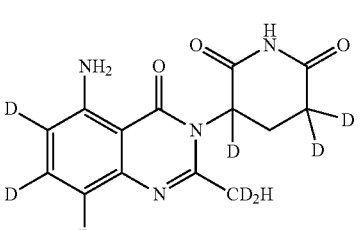
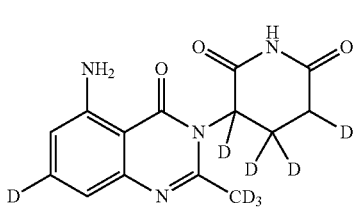
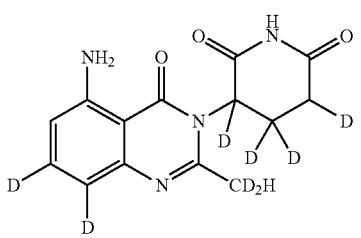 [SMILES: [2H]c1cc(N)c2c(=O)n(C3([2H])C(=O)NC(=O)C([2H])C3([2H])[2H])c(C([2H])([2H])[2H])nc2c1[2H]]

TABLE 1-continued
Deuterium enriched compounds of formula (I):
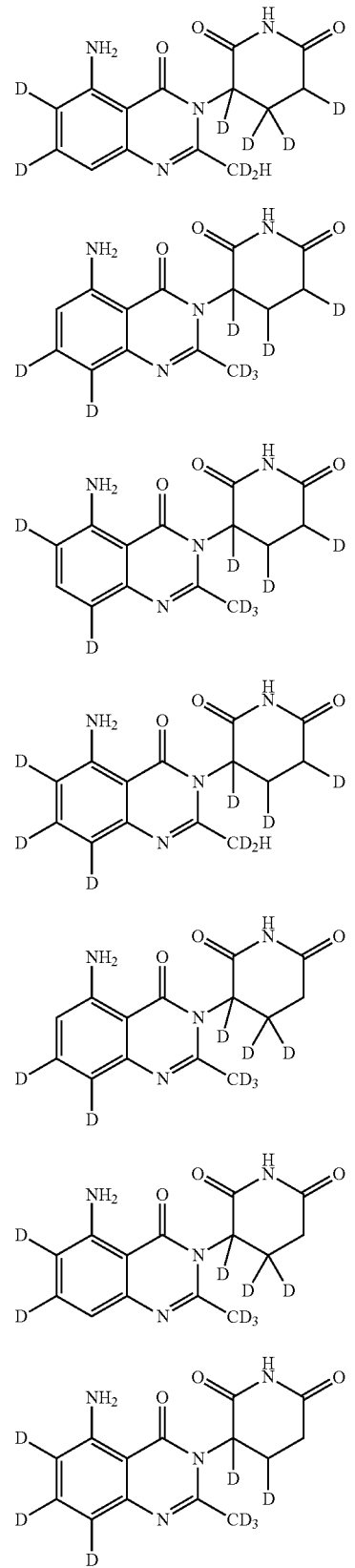
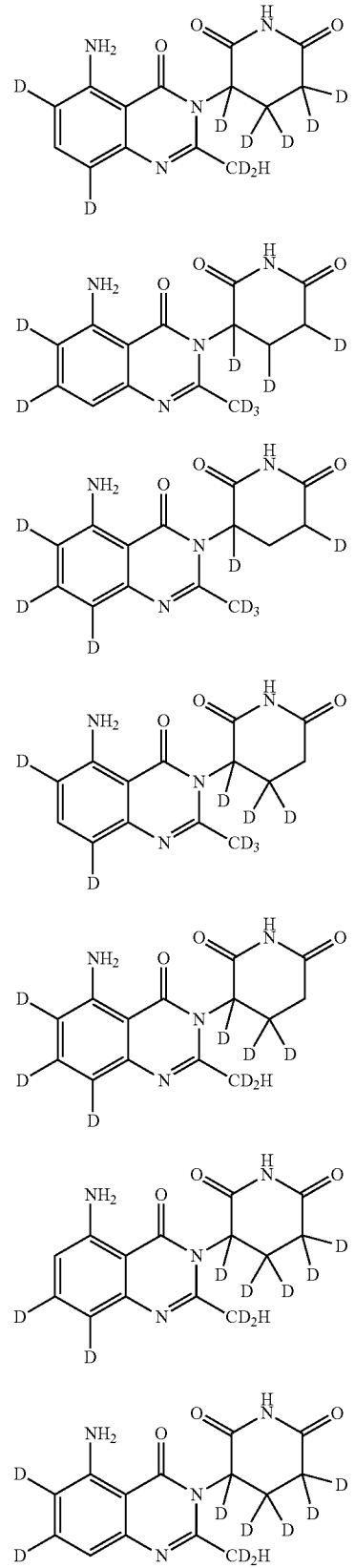

TABLE 1-continued
Deuterium enriched compounds of formula (I):
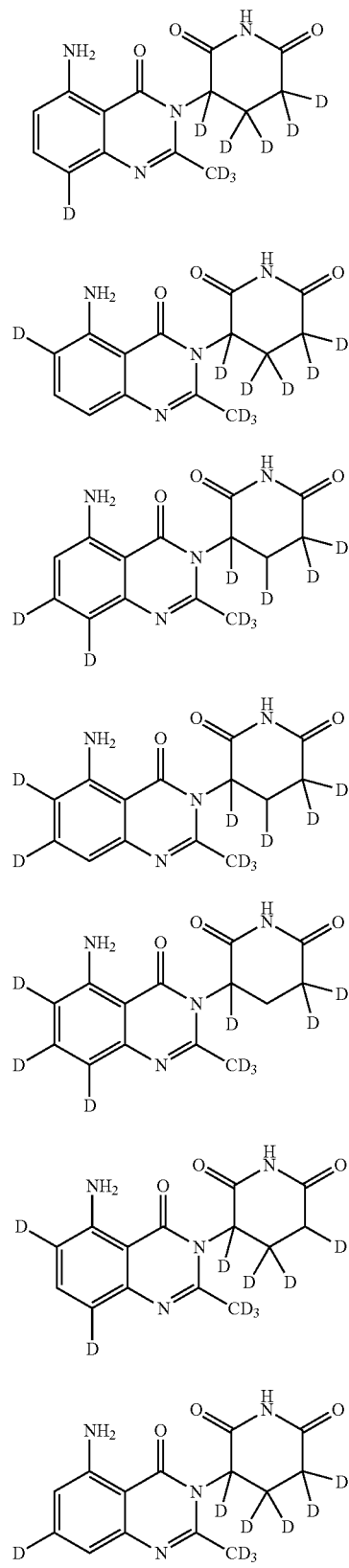
TABLE 1-continued
Deuterium enriched compounds of formula (I):
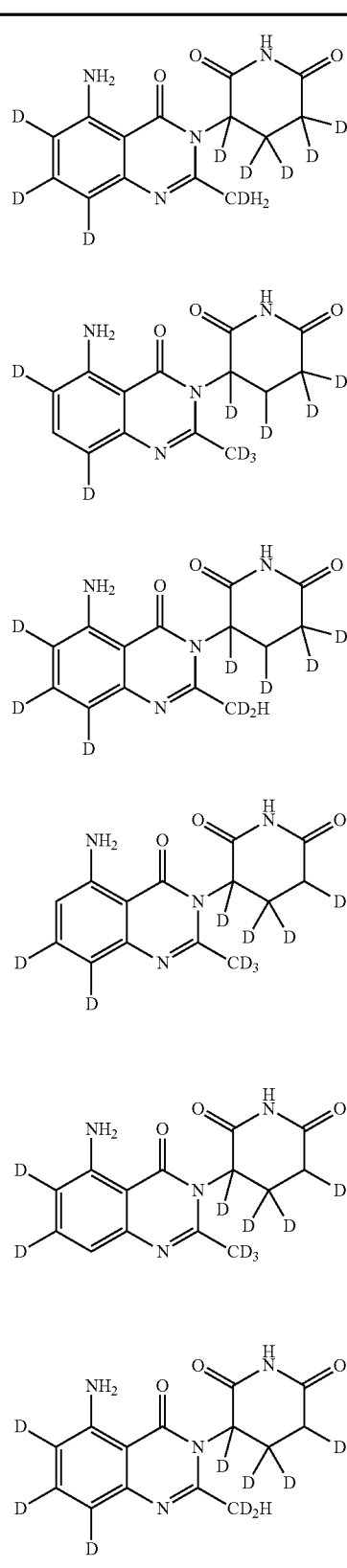

TABLE 1-continued

Deuterium enriched compounds of formula (I):

Particular embodiments of the invention include variations of the compounds listed in Table 1, wherein one, two or three of the protons bound to nitrogen (i.e., $Y^{12}$, $Y^{13}$, $Y^{14}$) is/are hydrogen(s) isotopically enriched with deuterium.

It is understood that one or more deuteriums may exchange with hydrogen under physiological conditions.

C. Methods of Preparation

Provided herein are methods for the preparation of isotopologues of 3-(5-amino-2-methyl-4-oxoquinazolin-3(4H)-yl)piperidine-2,6-dione, or enantiomers or mixtures of enantiomers thereof; or pharmaceutically acceptable salts, solvates, hydrates, cocrystals or polymorphs thereof. In certain embodiments, the methods provided herein are safe, efficient, cost effective, and/or readily scalable. In certain embodiments, the methods provided herein are suitable for the large scale or commercial production of isotopologues of 3-(5-amino-2-methyl-4-oxoquinazolin-3(4H)-yl)piperidine-2,6-dione, or enantiomers or mixtures of enantiomers thereof; or a pharmaceutically acceptable salts, solvates, hydrates, cocrystals or polymorphs thereof.

In some embodiments, provided herein is a method for preparing a compound of formula (I-A):

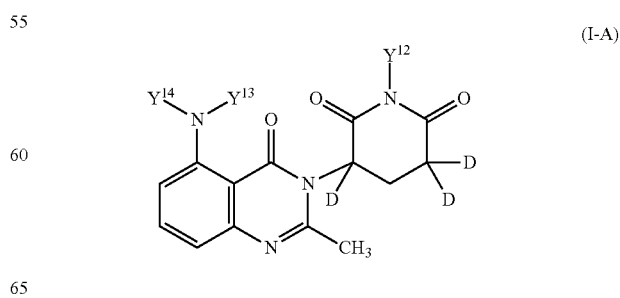

(I-A)

wherein $Y^{12}$, $Y^{13}$ and $Y^{14}$ are independently H or D, or an enantiomer or a mixture of enantiomers thereof; or a pharmaceutically acceptable salt, solvate, hydrate, cocrystal or polymorph thereof, comprising the steps of: (a) contacting 3-(5-amino-2-methyl-4-oxoquinazolin-3(4H)-yl)piperidine-2,6-dione with a base and an exchangeable deuterium source; (b) performing an aqueous workup on the reaction mixture from step (a) to form a compound of formula (I-A) or an enantiomer or a mixture of enantiomers thereof; or a pharmaceutically acceptable salt, solvate, hydrate, cocrystal or polymorph thereof; and (c) optionally obtaining enantiomers using chiral separation.

In certain embodiments, the base of step (a) (i.e., contacting 3-(5-amino-2-methyl-4-oxoquinazolin-3(4H)-yl)piperidine-2,6-dione with a base and an exchangeable deuterium source) is sodium $C_{1-14}$ alkoxide, potassium $C_{1-14}$ alkoxide, sodium hydride, potassium hydride, calcium hydride, cesium carbonate, lithium hexamethyldisilazide (LiHMDS), lithium diisopropylamide (LDA), 2-tert-butyl-1,1,3,3-tetramethyl-guanidine (Barton's Base), 1,8-diazabicyclo[5.4.0]undec-7-ene (DBU), 1,5-diazabicyclo[4.3.0]non-5-ene (DBN), 1,4-diazabicyclo(2.2.2)octane (DABCO), N,N-diisopropylethylamine (DIPEA or Hünig's base), pyridine, 2,6-di-tert-butyl-pyridine, 2,6-lutidine, lithium tetramethylpiperidide (LiTMP or harpoon base), 7-methyl-1,5,7 triazabicyclo[4.4.0]dec-5-ene (MTBD), 1,2,2,6,6-pentamethylpiperidine (PMP), 2,2,6,6-tetramethylpiperidine (TMP), tributylamine, 2,4,6-tri-tert-butylpyridine, tris(trimethylsilyl)amine, n-butyllithium, sec-butyllithium, tert-butyllithium, potassium bis(trimethylsilyl)amide, sodium tert-butoxide, tert-butylimino-tris(dimethylamino)phosphorane, or 2-tert-butylimino-2-diethylamino-1,3-dimethylperhydro-1,3,2-diazaphosphorine. In a particular embodiment, the base is potassium tert-butoxide.

In certain embodiments, the exchangeable deuterium source of step (a) (i.e., contacting 3-(5-amino-2-methyl-4-oxoquinazolin-3(4H)-yl)piperidine-2,6-dione with a base and an exchangeable deuterium source) is $D_2O$, $C_{1-14}$ alkyl-OD, $C_{1-14}$ alkyl-COOD, aryl-OD, heteroaryl-OD, aryl-$SO_3D$, deuterium chloride, deuterium bromide, deuterium iodide, sulfuric acid-$d_2$, nitric acid-$d_1$. In a particular embodiment, the deuterium source is tert-butyl-OD.

In certain embodiments, the aqueous workup of step (b) (i.e., performing an aqueous workup on the reaction mixture from step (a) to form a compound of formula (I-A)) is performed under acidic conditions. In certain embodiments, the acid selected for the aqueous workup lacks isotopically enriched acidic protons. In certain embodiments, the acid selected for the workup has one or more isotopically enriched acidic proton. In a particular embodiment, the aqueous workup comprising HCl. In another particular embodiment, the aqueous workup comprises DCl.

In certain embodiments the method of chiral separation is chiral column chromatography; in certain embodiments, the method of chiral separation is chiral resolution.

In another embodiment, provided herein is a method for preparing compounds of formula (I-B):

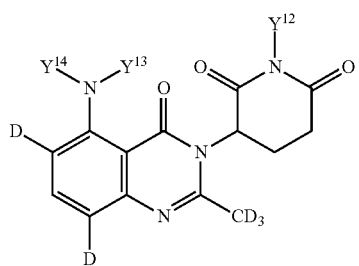

(I-B)

wherein $Y^{12}$, $Y^{13}$ and $Y^{14}$ are independently H or D, or an enantiomer or a mixture of enantiomers thereof; or a pharmaceutically acceptable salt, solvate, hydrate, cocrystal or polymorph thereof, comprising the steps of: (a) contacting 3-(5-amino-2-methyl-4-oxoquinazolin-3(4H)-yl)piperidine-2,6-dione or a salt thereof with an exchangeable deuterium source in a solvent to form a compound of formula (I-B), or an enantiomer or a mixture of enantiomers thereof or a pharmaceutically acceptable salt, solvate, hydrate, cocrystal or polymorph thereof; and (b) optionally obtaining enantiomers by chiral separation.

In certain embodiments, the exchangeable deuterium source of step (a) (i.e., contacting 3-(5-amino-2-methyl-4-oxoquinazolin-3(4H)-yl)piperidine-2,6-dione or a salt thereof with an exchangeable deuterium source in a deuterated solvent to form a compound of formula (I-B), or an enantiomer or a mixture of enantiomers thereof; or a pharmaceutically acceptable salt, solvate, hydrate, cocrystal or polymorph thereof, is one previously described herein elsewhere above. In a particular embodiment, the exchangeable deuterium source is $D_2O$.

In certain embodiments, the solvent of step (a) (i.e., contacting 3-(5-amino-2-methyl-4-oxoquinazolin-3(4H)-yl)piperidine-2,6-dione or a salt thereof with an exchangeable deuterium source in a solvent to form a compound of formula (I-B), or an enantiomer or a mixture of enantiomers thereof; or a pharmaceutically acceptable salt, solvate, hydrate, cocrystal or polymorph thereof) is a hydrocarbon, chlorinated hydrocarbon, alcohol, ether, ketone, ester, carbonate, amide, nitrile, sulfoxide, sulfone, nitro compound, arene, heteroarene, heterocycle, carboxylic acid, phosphoramide, carbon sulfide, water, or isotopically enriched analogues thereof. In a particular embodiment, the solvent in step (a) is DMSO-$d_6$.

In a particular embodiment, the salt of 3-(5-amino-2-methyl-4-oxoquinazolin-3(4H)-yl)piperidine-2,6-dione is the hydrochloride salt.

In certain embodiments the mode of chiral separation is chiral column chromatography; in certain embodiments, the mode of chiral separation is chiral resolution.

In other embodiments, provided herein is a method for preparing a compound of formula (I-C):

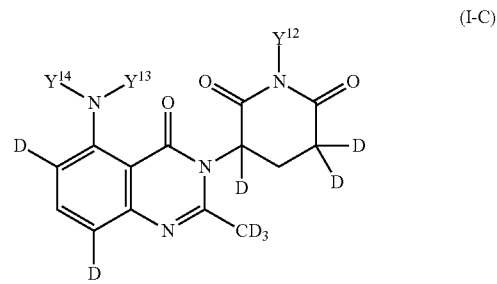

(I-C)

wherein $Y^{12}$, $Y^{13}$ and $Y^{14}$ are independently H or D, or an enantiomer or a mixture of enantiomers thereof; or a pharmaceutically acceptable salt, solvate, hydrate, cocrystal or polymorph thereof; comprising the steps of: (a) further contacting a compound of formula I-B with a base and an exchangeable deuterium source to form a compound of formula I-C or an enantiomer or a mixture of enantiomers thereof; or a pharmaceutically acceptable salt, solvate, hydrate, cocrystal or polymorph thereof; and (b) optionally obtaining enantiomers using chiral separation.

In certain embodiments, the base is one previously described herein elsewhere above.

In certain embodiments, the exchangeable deuterium source is one previously described herein elsewhere above.

In certain embodiments the method of chiral separation is chiral column chromatography; in certain embodiments, the method of chiral separation is chiral resolution.

In other embodiments, provided herein is a method for preparing a compound of formula (I-D):

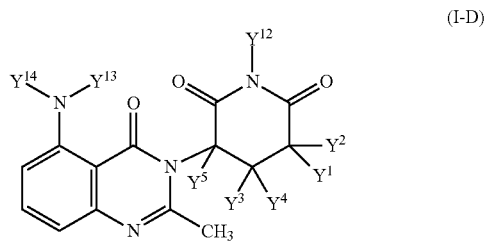

(I-D)

wherein $Y^1$, $Y^2$, $Y^3$, $Y^4$, $Y^5$, $Y^{12}$, $Y^{13}$ and $Y^{14}$ are independently H or D or an enantiomer or a mixture of enantiomers thereof; or a pharmaceutically acceptable salt, solvate, hydrate, cocrystal or polymorph thereof; comprising the steps of: (a) contacting 2-methyl-5-nitro-4H-benzo[d][1,3]oxazin-4-one with an isotopologue of glutarimide having the structure:

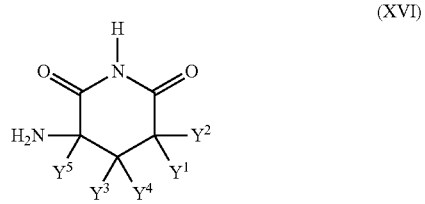

(XVI)

or a salt thereof, wherein $Y^1$, $Y^2$, $Y^3$, $Y^4$ and $Y^5$ are independently H or D, in a solvent in the presence of a coupling reagent to form compound of formula (XVII):

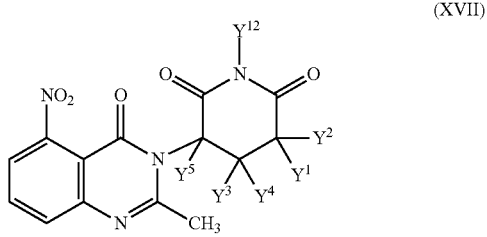

(XVII)

wherein $Y^1$, $Y^2$, $Y^3$, $Y^4$, $Y^5$ and $Y^{12}$ are independently H or D; (b) reducing XVII in a solvent to form a compound of formula (I-D) or an enantiomer or a mixture of enantiomers thereof; or a pharmaceutically acceptable salt, solvate, hydrate, cocrystal or polymorph thereof; and (c) optionally obtaining enantiomers using chiral separation.

In some embodiments, one or more hydrogens of the glutarimide ring (i.e. $Y^1$, $Y^2$, $Y^3$, $Y^4$ and $Y^5$) are enriched with deuterium through organic synthesis. In certain embodiments, a deuterium-enriched glutamic acid is converted to a N-Cbz protected deuterium-enriched glutamine using methods known in the art. See e.g., Miller et al., *Arch. Biochem. Biophys.*, 35, 176 (1952); Hegedus, B., *Helv. Chim. Acta* 31, 737 (1948). The N-Cbz protected deuterium-enriched glutamine may then subsequently be converted to an isotopologue of 3-(5-amino-2-methyl-4-oxoquinazolin-3(4H)-yl)piperidine-2,6-dione having a deuterium-enriched glutarimide ring. For example, in particular embodiments, commercially available $CO_2HCD_2CD_2CD(NH_2)CO_2H$ (formula 1) is converted to N-Cbz protected derivative 2, which is subsequently converted to compound I-D as shown in the following scheme.

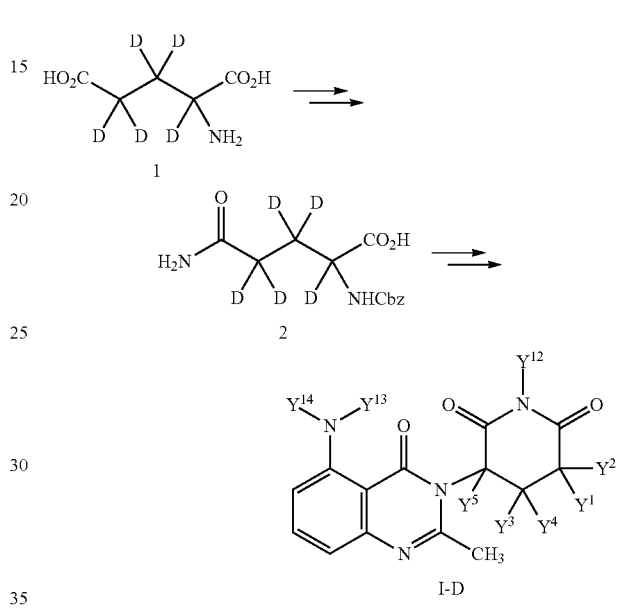

In certain embodiments, compound XVI or a salt thereof in step (a) (i.e., contacting 2-methyl-5-nitro-4H-benzo[d][1,3]oxazin-4-one and compound XVI or a salt thereof to form XVII) is the free base compound XVI. In certain embodiments, the compound XVI in step (a) is a salt of compound XVI. In certain embodiments, the compound XVI or a salt thereof in step (a) is the hydrochloride salt of compound XVI.

In certain embodiments, the coupling reagent in step (a) (i.e., contacting 2-methyl-5-nitro-4H-benzo[d][1,3]oxazin-4-one and compound XVI or a salt thereof to form compound XVII) is a carbodiimide, 1,1'-carbonyldiimidazole (CDI), bis(2-oxo-3-oxazolidinyl)phosphinic chloride (BOP-Cl), O-(7-azabenzotriazol-1-yl)-N,N,N',N'-tetramethyluronium hexafluorophosphate (HATU), (7-azabenzotriazol-1-yloxy)tripyrrolidinophosphonium hexafluorophosphate (PyAOP), (benzotriazol-1-yloxy)tripyrrolidinophosphonium hexafluorophosphate (PyBOP), (benzotriazol-1-yloxy)tris(dimethylamino)phosphonium hexafluorophosphate (BOP reagent), N,N,N',N'-tetramethyl-O-(1H-benzotriazol-1-yl)uronium hexafluorophosphate (HBTU), O-(benzotriazol-1-yl)-N,N,N',N'-tetramethyluronium tetrafluoroborate (TBTU), O-(benzotriazol-1-yl)-N,N,N',N'-bis(tetramethylene)uronium hexafluorophosphate (HBPyU), O-(benzotriazol-1-yl)-N,N,N',N'-bis(pentamethylene)uronium hexafluorophosphate, $PCl_3$, $PCl_5$, or 1-propanephosphonic acid cyclic anhydride. In certain embodiments, the coupling reagent in step (a) is N-(3-dimethylaminopropyl)-N'-ethylcarbodiimide (EDC or EDCI), N-(3-dimethylaminopropyl)-N'-ethylcarbodiimide hydrochloride (EDC hydrochloride), 1-[3-(dimethylamino)propyl]-3-ethylcarbodiimide methiodide (EDC methiodide), 1-cyclohexyl-3-(2-morpholinoethyl)carbodiimide metho-p-toluenesulfonate, or 1,3-dicyclohexylcarbodiimide (DCC). In certain embodiments, the coupling reagent in step (a) is $PCl_3$, $PCl_5$, 1-propanephosphonic acid cyclic anhydride, $POCl_3$, or a mixture of $POCl_3$ and water. In certain embodiments, the coupling reagent in step (a) contains $PCl_3$, $PCl_5$, 1-propanephosphonic acid cyclic anhydride, acetic anhydride, phosphoric acid, $POCl_3$, or a mixture of $POCl_3$ and water. In certain embodiments, the coupling reagent in step (a) is 1-propanephosphonic acid cyclic anhydride. In certain embodiments, the coupling reagent in step (a) contains acetic anhydride. In certain embodiments, the coupling reagent in step (a) contains acetic anhydride and phosphoric acid. In certain embodiments, the coupling reagent in step (a) is a mixture of acetic anhydride and phosphoric acid. In certain embodiments, the coupling reagent in step (a) contains $POCl_3$. In certain embodiments, the coupling reagent in step (a) contains $POCl_3$ and water. In certain embodiments, the coupling reagent in step (a) is a mixture of $POCl_3$ and water. In certain embodiments, the molar ratio of $POCl_3$ versus water is ranging from about 0.5 to about 5; from about 0.7 to about 4; or from about 1 to about 3. In certain embodiments, the molar ratio of $POCl_3$ versus water is about 1, about 1.5, about 2, or about 3.

In certain embodiments, the solvent in step (a) (i.e., contacting 2-methyl-5-nitro-4H-benzo[d][1,3]oxazin-4-one and compound XVI or a salt thereof to form XVII) is a hydrocarbon, chlorinated hydrocarbon, alcohol, ether, ketone, ester, carbonate, amide, nitrile, sulfoxide, sulfone, nitro compound, arene, heteroarene, heterocycle, carboxylic acid, phosphoramide, carbon sulfide, water, or a mixture thereof.

In certain embodiments, the solvent in step (a) (i.e., contacting 2-methyl-5-nitro-4H-benzo[d][1,3]oxazin-4-one and compound XVI or a salt thereof to form XVII) is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl) ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent in step (a) (i.e., contacting 2-methyl-5-nitro-4H-benzo[d][1,3]oxazin-4-one and compound XVI or a salt thereof to form XVII) is a nitrile. In certain embodiments, the solvent in step (a) is a carboxylic acid ester. In certain embodiments, the solvent in step (a) is a mixture of a nitrile and carboxylic acid ester. In certain embodiments, the solvent in step (a) is an amide. In certain embodiments, the solvent in step (a) is a cyclic amide. In certain embodiments, the solvent in step (a) is 1-methyl-2-pyrrolidone (NMP), acetonitrile, THF, or 2-methyl-THF. In certain embodiments, the solvent in step (a) is NMP. In certain embodiments, the volume ratio of the nitrile versus carboxylic acid ester is ranging from about 0.1 to about 100, from about 0.2 to about 50, from about 0.5 to about 25, from about 1 to about 20, from about 1 to about 10, from about 1 to about 5, or from about 1 to about 2. In certain embodiments, the volume ratio of the nitrile versus carboxylic acid ester is ranging from about 0.1 to about 100. In certain embodiments, the volume ratio of the nitrile versus carboxylic acid ester is ranging from about 0.2 to about 50. In certain embodiments, the volume ratio of the nitrile versus carboxylic acid ester is ranging from about 0.5 to about 25. In certain embodiments, the volume ratio of the nitrile versus carboxylic acid ester is ranging from about 1 to about 20. In certain embodiments, the volume ratio of the nitrile versus carboxylic acid ester is ranging from about 1 to about 10. In certain embodiments, the volume ratio of the nitrile versus carboxylic acid ester is ranging from about 1 to about 5. In certain embodiments, the volume ratio of the nitrile versus carboxylic acid ester is ranging from about 1 to about 2. In certain embodiments, the volume ratio between acetonitrile and ethyl acetate is about 1, about 1.1, about 1.2, about 1.3, about 1.4, about 1.5, about 1.6, about 1.7, about 1.8, about 1.9, or about 2.

In certain embodiments, the solvent in step (a) (i.e., contacting 2-methyl-5-nitro-4H-benzo[d][1,3]oxazin-4-one and compound XVI or a salt thereof to form XVII) is acetonitrile. In certain embodiments, the solvent in step (a) is ethyl acetate. In certain embodiments, the solvent in step (a) is a mixture of acetonitrile and ethyl acetate. In certain embodiments, the volume ratio of acetonitrile versus ethyl acetate is ranging from about 0.1 to about 100, from about 0.2 to about 50, from about 0.5 to about 25, from about 1 to about 20, from about 1 to about 10, from about 1 to about 5, or from about 1 to about 2. In certain embodiments, the volume ratio of acetonitrile versus ethyl acetate is ranging from about 0.1 to about 100. In certain embodiments, the volume ratio of acetonitrile versus ethyl acetate is ranging from about 0.2 to about 50. In certain embodiments, the volume ratio of acetonitrile versus ethyl acetate is ranging from about 0.5 to about 25. In certain embodiments, the volume ratio of acetonitrile versus ethyl acetate is ranging from about 1 to about 20. In certain embodiments, the volume ratio of acetonitrile versus ethyl acetate is ranging from about 1 to about 10. In certain embodiments, the volume ratio of acetonitrile versus ethyl acetate is ranging from about 1 to about 5. In certain embodiments, the volume ratio of acetonitrile versus ethyl acetate is ranging from about 1 to about 2. In certain embodiments, the volume ratio of acetonitrile versus ethyl acetate is about 1, about 1.1, about 1.2, about 1.3, about 1.4, about 1.5, about 1.6, about 1.7, about 1.8, about 1.9, or about 2.

In certain embodiments, the molar ratio of the coupling reagent versus 2-methyl-5-nitro-4H-benzo[d][1,3]oxazin-4-one in step (a) (i.e., contacting 2-methyl-5-nitro-4H-benzo[d][1,3]oxazin-4-one and compound XVI or a salt thereof to form XVII) is ranging from about 1 to about 10, from about 1 to about 5, or from about 1 to about 3. In certain embodiments, the molar ratio of the coupling reagent versus 2-methyl-5-nitro-4H-benzo[d][1,3]oxazin-4-one is ranging from about 1 to about 10. In certain embodiments, the molar ratio of the coupling reagent versus 2-methyl-5-nitro-4H-benzo[d][1,3]oxazin-4-one is ranging from about 1 to about 5. In certain embodiments, the molar ratio of the coupling reagent versus 2-methyl-5-nitro-4H-benzo[d][1,3]oxazin-4-one is ranging from about 1 to about 3. In certain embodiments, the molar ratio of the coupling reagent versus 2-methyl-5-nitro-4H-benzo[d][1,3]oxazin-4-one is about 1, about 1.5, about 2, about 2.5 or about 3.

In certain embodiments, step (a) (i.e., contacting 2-methyl-5-nitro-4H-benzo[d][1,3]oxazin-4-one and compound XVI or a salt thereof to form XVII) is conducted at a temperature ranging from about 0 to about 150° C., from about 25 to about 120° C., from about 50 to about 100° C., from about 60 to about 100° C., from about 70 to about 90° C., from about 70 to about 85° C., or from about 75 to about 80° C. In certain embodiments, step (a) is conducted at a temperature from about 75 to about 80° C.

In certain embodiments, the reduction of the nitro group of compound XVII in a solvent to form a compound of formula I-D in step is via a transfer hydrogenation. In certain embodiments, the reduction in step (b) is via catalytic hydrogenation. In certain embodiments, the reduction in step (b) is via catalytic hydrogenation under a hydrogen atmosphere. In certain embodiments, the reduction in step (b) is via catalytic hydrogenation in the presence of hydrogen gas ($H_2$). In certain embodiments, the reduction in step (b) is performed via catalytic hydrogenation in the presence of hydrogen gas and a palladium catalyst. In certain embodiments, the reduction in step (b) is performed via catalytic hydrogenation according to the procedures as described in U.S. Pat. No. 7,635,700, the disclosure of which is incorporated by reference in its entirety.

In one embodiment, the transfer hydrogenation is conducted in the presence of a hydrogen donor. In another embodiment, the transfer hydrogenation is conducted in the presence of a catalyst. In yet another embodiment, the transfer hydrogenation is conducted in the presence of a hydrogen donor and a catalyst.

In certain embodiments, the hydrogen donor is (i) a $C_{1-14}$ alcohol, $C_{1-14}$ carboxylic acid, $C_{1-14}$ carboxylic acid salt, $C_{1-14}$ carboxylic acid ester, $C_{2-14}$ alkene, $C_{3-14}$ cycloalkene, $C_{6-14}$ arene, heteroarene, or heterocycle, each of which is optionally substituted with one or more substituents Q; or (ii) diazene (also known as diimine or diimide), hydrazine, hydroxylamine, or $NaH_2PO_2$.

In certain embodiments, the hydrogen donor is a $C_{1-14}$ alcohol, optionally substituted with one or more substituents Q. In certain embodiments, the hydrogen donor is a primary or secondary $C_{1-14}$ alcohol, each optionally substituted with one or more substituents Q. In certain embodiments, the hydrogen donor is a primary $C_{1-14}$ alcohol, optionally substituted with one or more substituents Q. In certain embodiments, the hydrogen donor is a secondary $C_{1-14}$ alcohol, optionally substituted with one or more substituents Q. In certain embodiments, the hydrogen donor is methanol, ethanol, propan-1-ol, propan-2-ol, butan-1-ol, butan-2-ol, cyclopentanol, cyclohexanol, benzylalcohol, a menthol, or a mixture thereof.

In certain embodiments, the hydrogen donor has one or more isotopically enriched hydrogens. In certain embodiments, the hydrogen donor is a $C_{1-14}$ carboxylic acid, optionally substituted with one or more substituents Q. In certain embodiments, the hydrogen donor is a 2-hydroxy-$C_{1-14}$ carboxylic acid, optionally substituted with one or more substituents Q. In certain embodiments, the hydrogen donor is formic acid, lactic acid, ascorbic acid, mandelic acid, or a mixture thereof. In certain embodiments, the hydrogen donor is formic acid. In certain embodiments, the hydrogen donor is formic acid-$d_2$.

In certain embodiments, the solvent in the transfer hydrogenation is formic acid. In certain embodiments, the solvent in the transfer hydrogenation is water. In certain embodiments, the formic acid is isotopically enriched. In certain embodiments, the water is isotopically enriched. In certain embodiments, both the formic acid and water are isotopically enriched. In certain embodiments, the formic acid is HCOOH. In certain embodiments, the formic acid is DCOOD (formic acid-$d_2$). In certain embodiments, the formic acid is DCOOH. In certain embodiments, the formic acid is HCOOD. In certain embodiments the formic acid is a combination of two or more of HCOOH, DCOOD, DCOOH, and HCOOD.

In certain embodiments, the hydrogen donor is a $C_{1-14}$ carboxylic acid salt, optionally substituted with one or more substituents Q. In certain embodiments, the hydrogen donor is a carboxylic acid amine salt, optionally substituted with one or more substituents Q. In certain embodiments, the hydrogen donor is a carboxylic acid amine salt, wherein the amine is an aromatic amine. In certain embodiments, the hydrogen donor is a carboxylic acid amine salt, wherein the amine is pyridine. In certain embodiments, the hydrogen donor is a carboxylic acid amine salt, wherein the amine is a non-aromatic amine. In certain embodiments, the hydrogen donor is a carboxylic acid amine salt, wherein the amine is a primary, secondary, or tertiary amine. In certain embodiments, the hydrogen donor is a carboxylic acid amine salt, wherein the amine is a primary amine. In certain embodiments, the hydrogen donor is a carboxylic acid amine salt, wherein the amine is a secondary amine. In certain embodiments, the hydrogen donor is a carboxylic acid amine salt, wherein the amine is a tertiary amine. In certain embodiments, the hydrogen donor is a carboxylic acid amine salt, wherein the amine is a tri-($C_{1-6}$ alkyl)amine. In certain embodiments, the hydrogen donor is a carboxylic acid amine salt, wherein the amine is a trimethylamine, triethylamine, di(isopropyl)ethylamine, pyridine, or a mixture thereof. In certain embodiments, the hydrogen donor is a $C_{1-14}$ carboxylic acid ammonium salt. In certain embodiments, the hydrogen donor is ammonium formate or potassium formate.

In certain embodiments, the hydrogen donor is a $C_{1-14}$ carboxylic acid ester.

In certain embodiments, the hydrogen donor is $C_{2-14}$ alkene, optionally substituted with one or more substituents Q. In certain embodiments, the hydrogen donor is a terpene.

In certain embodiments, the hydrogen donor is $C_{3-14}$ cycloalkene, optionally substituted with one or more substituents Q. In certain embodiments, the hydrogen donor is cyclohexadiene, cyclohexene, 1-methylcyclohexene, or a mixture thereof.

In certain embodiments the hydrogen donor is $C_{6-14}$ arene, optionally substituted with one or more substituents Q. In certain embodiments the hydrogen donor is tetralin.

In certain embodiments the hydrogen donor is a heteroarene, optionally substituted with one or more substituents Q.

In certain embodiments the hydrogen donor is a heterocycle, optionally substituted with one or more substituents Q. In certain embodiments the hydrogen donor is dihydrofuran.

In certain embodiments, the hydrogen donor is diazene, hydrazine, hydroxylamine, or $NaH_2PO_2$.

In certain embodiments, the hydrogen donor is methanol, ethanol, propan-1-ol, propan-2-ol, butan-1-ol, butan-2-ol, cyclopentanol, cyclohexanol, benzylalcohol, a menthol, formic acid, lactic acid, ascorbic acid, mandelic acid, ammonium formate, potassium formate, cyclohexadiene, cyclohexene, 1-methylcyclohexene, tetralin, dihydrofuran, a terpene, diazene, hydrazine, hydroxylamine, or $NaH_2PO_2$, or a mixture thereof. In certain embodiments, the hydrogen donor is formic acid, ammonium formate, potassium formate, cyclohexene, 1-methylcyclohexene, $NaH_2PO_2$, or a mixture thereof.

In certain embodiments, the catalyst is a hydrogenation catalyst. In certain embodiments, the catalyst is a heterogeneous hydrogenation catalyst. In certain embodiments, the catalyst is Raney nickel, palladium, palladium black, palladium on carbon (Pd/C), palladium oxide, Lindlar catalyst, palladium hydroxide on carbon (also known as Pearlman's catalyst), platinum, platinum black, platinum on carbon (Pt/C), or platinum dioxide (also known as Adam's catalyst). In certain embodiments, the catalyst is a homogeneous hydrogenation catalyst. In certain embodiments, the homogeneous catalyst is an iridium-based catalyst. In certain embodiments, the homogeneous catalyst is a palladium-based catalyst. In certain embodiments, the homogeneous catalyst is a platinum-based catalyst. In certain embodiments, the homogeneous catalyst is a rhodium-based catalyst. In certain embodiments, the homogeneous catalyst is chloro-tris(triphenylphosphine)rhodium(I) (also known as Wilkinson's catalyst). In certain embodiments, the homogeneous catalyst is an iridium-based catalyst. In certain embodiments, the homogeneous catalyst is Crabtree's catalyst.

In certain embodiments, the catalyst is a precious metal catalyst. In certain embodiments, the catalyst is an iridium, palladium, platinum, rhodium, or ruthenium catalyst. In certain embodiments, the catalyst is an iridium catalyst. In certain embodiments, the catalyst is a palladium catalyst. In certain embodiments, the catalyst is palladium, palladium black, palladium on carbon (Pd/C), palladium oxide, Lindlar catalyst or palladium hydroxide on carbon (also known as Pearlman's catalyst). In certain embodiments, the catalyst is a platinum catalyst. In certain embodiments, the catalyst is palladium. In certain embodiments, the catalyst is palladium black. In certain embodiments, the catalyst is palladium on carbon (Pd/C). In certain embodiments, the catalyst is palladium oxide. In certain embodiments, the catalyst is Lindlar catalyst. In certain embodiments, the catalyst is a platinum catalyst. In certain embodiments, the catalyst is platinum, platinum black, platinum on carbon (Pt/C), or platinum dioxide. In certain embodiments, the catalyst is platinum. In certain embodiments, the catalyst is platinum black. In certain embodiments, the catalyst is platinum on carbon (Pt/C). In certain embodiments, the catalyst is platinum dioxide. In certain embodiments, the catalyst is a rhodium catalyst. In certain embodiments, the catalyst is a ruthenium catalyst.

In certain embodiments, the catalyst is a non-precious metal catalyst. In certain embodiments, the catalyst is a nickel catalyst. In certain embodiments, the catalyst is Raney nickel.

In certain embodiments, the solvent in the transfer hydrogenation is a hydrocarbon, chlorinated hydrocarbon, alcohol, ether, ketone, ester, carbonate, amide, nitrile, sulfoxide, sulfone, nitro compound, heteroarene, heterocycle, carboxylic acid, phosphoramide, carbon sulfide, water, or a mixture thereof.

In certain embodiments, the solvent in the transfer hydrogenation is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent in the transfer hydrogenation is a carboxylic acid. In certain embodiments, the solvent in the transfer hydrogenation is a mixture of a carboxylic acid and water. In certain embodiments, the volume ratio of the carboxylic acid versus water is ranging from about 0.1 to about 10, from about 0.2 to about 5, from about 0.5 to about 5, from about 0.5 to about 2, or from about 0.8 to about 1.5. In certain embodiments, the volume ratio of the carboxylic acid versus water is ranging from about 0.1 to about 10. In certain embodiments, the volume ratio of the carboxylic acid versus water is ranging from about 0.2 to about 5. In certain embodiments, the volume ratio of the carboxylic acid versus water is ranging from about 0.5 to about 5. In certain embodiments, the volume ratio of the carboxylic acid versus water is ranging from about 0.5 to about 2. In certain embodiments, the volume ratio of the carboxylic acid versus water is ranging from about 0.8 to about 1.5. In certain embodiments, the volume ratio of the carboxylic acid versus water is about 0.5, about 0.6, about 0.7, about 0.8, about 0.9, about 1, about 1.1, about 1.2, about 1.3, about 1.4, or about 1.5. In certain embodiments, the volume ratio of the carboxylic acid versus water is about 0.8, about 0.9, about 1, about 1.1, or about 1.2. In certain embodiments, the volume ratio of the carboxylic acid versus water is about 0.8. In certain embodiments, the volume ratio of the carboxylic acid versus water is about 0.9. In certain embodiments, the volume ratio of the carboxylic acid versus water is about 1. In certain embodiments, the volume ratio of the carboxylic acid versus water is about 1.1. In certain embodiments, the volume ratio of the carboxylic acid versus water is about 1.2.

In certain embodiments, the solvent in the transfer hydrogenation is a mixture of formic acid and water. In certain embodiments, the volume ratio of formic acid versus water is ranging from about 0.1 to about 10, from about 0.2 to about 5, from about 0.5 to about 5, from about 0.5 to about 2, or from about 0.8 to about 1.5. In certain embodiments, the volume ratio of formic acid versus water is ranging from about 0.1 to about 10. In certain embodiments, the volume ratio of formic acid versus water is ranging from about 0.2 to about 5. In certain embodiments, the volume ratio of formic acid versus water is ranging from about 0.5 to about 5. In certain embodiments, the volume ratio of formic acid versus water is ranging from about 0.5 to about 2. In certain embodiments, the volume ratio of formic acid versus water is ranging from about 0.8 to about 1.5. In certain embodiments, the volume ratio of formic acid versus water is about 0.5, about 0.6, about 0.7, about 0.8, about 0.9, about 1, about 1.1, about 1.2, about 1.3, about 1.4, or about 1.5. In certain embodiments, the volume ratio of formic acid versus water is about 0.8, about 0.9, about 1, about 1.1, or about 1.2. In certain embodiments, the volume ratio of formic acid versus water is about 0.8. In certain embodiments, the volume ratio of formic acid versus water is about 0.9. In certain embodiments, the volume ratio of formic acid versus water is about 1. In certain embodiments, the volume ratio of formic acid versus water is about 1.1. In certain embodiments, the volume ratio of formic acid versus water is about 1.2.

In certain embodiments, the molar ratio of formic acid versus compound XVII is ranging from about 1 to about 100, from about 2 to about 50, from about 5 to about 50, from about 5 to about 25, from about 10 to about 25, or from about 15 to about 25. In certain embodiments, the molar ratio of formic acid versus compound XVII is ranging from about 1 to about 100. In certain embodiments, the molar ratio of formic acid versus XVII is ranging from about 2 to about 50. In certain embodiments, the molar ratio of formic acid versus compound XVII is ranging from about 5 to about 50. In certain embodiments, the molar ratio of formic acid versus 3-(2-methyl-5-nitro-4-oxoquinazolin-3(4H)-yl)piperidine-2,6-dione is ranging from about 5 to about 25. In certain embodiments, the molar ratio of formic acid versus 3-(2-methyl-5-nitro-4-oxoquinazolin-3(4H)-yl)piperidine-2,6-dione is ranging from about 10 to about 25. In certain embodiments, the molar ratio of formic acid versus 3-(2-methyl-5-nitro-4-oxoquinazolin-3(4H)-yl)piperidine-2,6-dione is ranging from about 15 to about 25. In certain embodiments, the molar ratio of formic acid versus 3-(2-methyl-5-nitro-4-oxoquinazolin-3(4H)-yl)piperidine-2,6-dione is about 15, about 16, about 17, about 18, about 19, about 20, about 21, about 22, about 23, about 24, or about 25.

In certain embodiments, the transfer hydrogenation is performed at a temperature ranging from about 0 to about 100° C., from about 5 to about 90° C., from about 5 to about 80° C., from about 10 to about 70° C., or from about 10 to about 60° C.

In certain embodiments, when the hydrogen donor is formic acid, the transfer hydrogenation further comprises the step of hydrolyzing the isotopologue of N-(3-(2,6-dioxopiperidin-3-yl)-2-methyl-4-oxo-3,4-dihydroquinazolin-5-yl)formamide to form the free amine. In certain embodiments, the hydrolysis step is performed in the presence of a deformylation catalyst. In certain embodiments, the deformylation catalyst is an acid. In certain embodiments, the deformylation catalyst is an organic acid. In certain embodiments, the deformylation catalyst is an inorganic acid. In certain embodiments, the deformylation catalyst is hydrochloride.

In certain embodiments, the solvent in the deformylation step is a hydrocarbon, chlorinated hydrocarbon, alcohol, ether, ketone, ester, carbonate, amide, nitrile, sulfoxide, sulfone, nitro compound, heteroarene, heterocycle, carboxylic acid, phosphoramide, carbon sulfide, water, or a mixture thereof.

In certain embodiments, the solvent in the deformylation step is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl) ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent in the deformylation step comprises a $C_{1-6}$ alcohol. Without being limited by any theory, the alcohol acts as a reagent in the deformylation step. In certain embodiments, the solvent in the deformylation step comprises ethanol. In certain embodiments, the solvent in the deformylation step comprises a $C_{1-6}$ alcohol and water. In certain embodiments, the solvent in the deformylation step comprises ethanol and water. In certain embodiments, the solvent in the deformylation step comprises formic acid, a $C_{1-6}$ alcohol, and water. In certain embodiments, the solvent in the deformylation step comprises formic acid, ethanol, and water. In certain embodiments, the solvent in the deformylation step comprises formic acid, a $C_{1-6}$ alcohol, and water. In certain embodiments, the solvent in the deformylation step is a mixture formic acid, a $C_{1-6}$ alcohol, and water. In certain embodiments, the solvent in the deformylation step is a mixture of formic acid, ethanol, and water.

In certain embodiments, the deformylation step is performed at a temperature ranging from about 50 to about 120° C., from about 60 to about 100° C., from about 60 to about 90° C., from or about 65 to about 85° C.

In certain embodiments, the reduction of compound XVII to compound I-D is performed at a temperature ranging from about 0 to about 100° C., from about 5 to about 90° C., from about 5 to about 85° C., from about 10 to about 90° C., or from about 10 to about 85° C.

In certain embodiments provided herein, is a method for preparing a compound of formula (I-E):

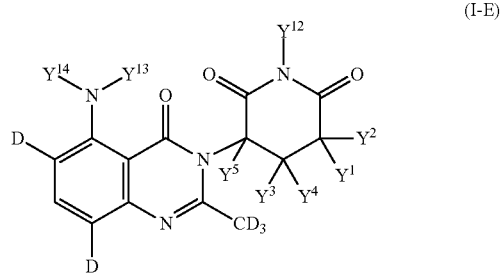

(I-E)

wherein $Y^1$, $Y^2$, $Y^3$, $Y^4$, $Y^5$, $Y^{12}$, $Y^{13}$ and $Y^{14}$ are independently H or D, or an enantiomer or a mixture of enantiomers thereof; or a pharmaceutically acceptable salt, solvate, hydrate, cocrystal or polymorph thereof; comprising the steps of: (a) further contacting compound I-D with an acid and an exchangeable deuterium source in a solvent to give a compound of formula (I-E); and (b) optionally obtaining enantiomers using chiral separation.

In certain embodiments, the acid is $C_{1-14}$ alkyl-COOD, aryl-OD, heteroaryl-OD, $C_{1-15}$ alkyl-$SO_3D$ and aryl-$SO_3D$. In certain embodiments, the acid deuterium bromide, deuterium iodide, sulfuric acid-$d_2$, nitric acid-$d_1$ or trifluoromethanesulfonic acid-$d_1$. In a particular embodiment, the acid is deuterium chloride.

In certain embodiments, the solvent is one previously described herein elsewhere above. In a particular embodiment, the solvent is DMSO-$d_6$.

In other embodiments, provided herein is a method for preparing a compound of formula (I-F):

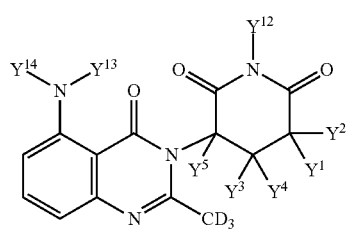

(I-F)

wherein $Y^1$, $Y^2$, $Y^3$, $Y^4$, $Y^5$, $Y^{12}$, $Y^{13}$ and $Y^{14}$ are independently H or D, or an enantiomer or a mixture of enantiomers thereof; or a pharmaceutically acceptable salt, solvate, hydrate, cocrystal or polymorph thereof; comprising the steps of: (a) contacting 2-(methyl-$d_3$)-5-nitro-4H-benzo[d][1,3]oxazin-4-one with a glutarimide of formula XVI or a salt thereof in a solvent in the presence of a coupling agent to form a compound of formula (XVIII):

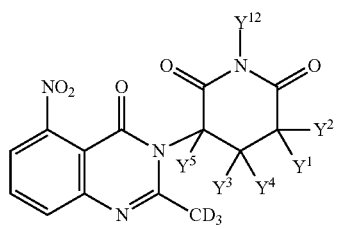

(XVIII)

wherein $Y^1$, $Y^2$, $Y^3$, $Y^4$, $Y^5$, and $Y^{12}$ are independently H or D; (b) reducing compound (XVIII) in the presence of formic acid-$d_2$ via transfer hydrogenation in a solvent to form a compound of formula (I-F), wherein $Y^1$, $Y^2$, $Y^3$, $Y^4$, $Y^5$, $Y^{12}$, $Y^{13}$ and $Y^{14}$ are independently H or D, or an enantiomer or a mixture of enantiomers thereof; or a pharmaceutically acceptable salt, solvate, hydrate, cocrystal or polymorph thereof; and (c) optionally obtaining enantiomers using chiral separation.

In certain embodiments, deuterated 2-(methyl-$d_3$)-5-nitro-4H-benzo[d][1,3]oxazin-4-one is prepared by contacting 2-amino-6-nitrobenzoic acid with acetic anhydride-$d_6$.

In other embodiments, provided herein is a method for preparing a compound of formula (I-G):

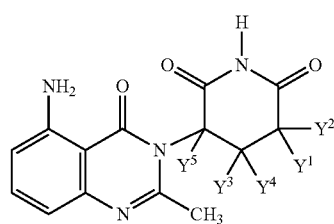

(I-G)

wherein $Y^1$, $Y^2$, $Y^3$, $Y^4$, and $Y^5$ are independently H or D, or an enantiomer or a mixture of enantiomers thereof; or a pharmaceutically acceptable salt, solvate, hydrate, cocrystal or polymorph thereof; comprising the steps of: (a) contacting 2-amino-6-nitrobenzoic acid or a salt thereof with a carbonyl equivalent in a solvent to form 5-nitro-1H-benzo[d][1,3]oxazine-2,4-dione; (b) contacting 5-nitro-1H-benzo[d][1,3]oxazine-2,4-dione with compound XIX:

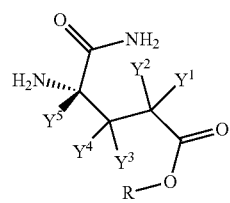

(XIX)

wherein $Y^1$, $Y^2$, $Y^3$, $Y^4$ and $Y^5$ are independently H or D, and R is an alkyl, aryl or arylalkyl group as previously described herein, in the presence of a base in a solvent to form compound (XX):

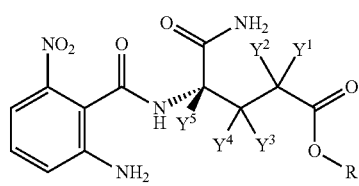

(XX)

wherein $Y^1$, $Y^2$, $Y^3$, $Y^4$, and $Y^5$ are independently H or D; (c) contacting XX with an acetylating reagent in the presence of an acid to form compound XXI:

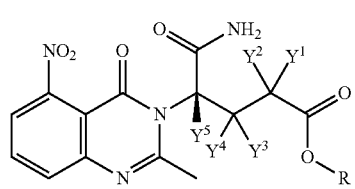

(XXI)

wherein $Y^1$, $Y^2$, $Y^3$, $Y^4$ and $Y^5$ are independently H or D; (d) contacting compound XXI with a base in a solvent followed by a workup to form compound XXII:

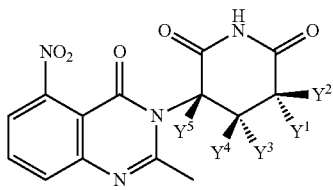
(XXII)

wherein $Y^1$, $Y^2$, $Y^3$, $Y^4$ and $Y^5$ are independently H or D; (e) reducing XXII in the presence of formic acid-$d_2$ via transfer hydrogenation in a solvent to form a compound of formula (I-G) or an enantiomer or a mixture of enantiomers thereof; or a pharmaceutically acceptable salt, solvate, hydrate, cocrystal or polymorph thereof; and (f) optionally obtaining enantiomers using chiral separation.

In a certain embodiment, the base in step (b) (i.e. contacting 5-nitro-1H-benzo[d][1,3]oxazine-2,4-dione with compound XIX, wherein $Y^1$, $Y^2$, $Y^3$, $Y^4$ and $Y^5$ are independently H or D, in the presence of a base in a solvent to form compound (XX)) is sodium bicarbonate, sodium carbonate, sodium hydroxide, cesium carbonate, potassium carbonate, potassium bicarbonate, triethylamine, diisopropylethylamine, tributylamine, lithium hydroxide, potassium hydroxide, pyridine, 4-dimethylaminopyridine, 2,6-lutidine or 2,6-di-tert-butylpyridine.

In certain embodiments, the carbonyl equivalent is phosgene, diphosgene, carbonyl diimidazole, or carbonyl diimidazoledisuccinimidyl carbonate. In a particular embodiment, the carbonyl equivalent is triphosgene.

In a certain embodiment, the acetylating agent is acetic anhydride, acetic acid, acetyl chloride, or acetyl bormide. In a certain embodiment, the acetylating agent is an orthoester. In a particular embodiment, the orthoester is triethyl orthoacetate. In a particular embodiment, the orthoester is triethylorthoacetate and the acid is p-toluenesulfonic acid monohydrate (PTSA hydrate).

In certain embodiments, the base in step (d) (i.e. contacting compound XXI with a base in a solvent followed by a workup to form compound XXII) is potassium $C_{1-14}$ alkoxide. In certain embodiments, the base is sodium $C_{1-14}$ alkoxide. In certain embodiments, the base is sodium hydride. In certain embodiments, the base is potassium hydride. In certain embodiments, the base is calcium hydride. In certain embodiments, the base is lithium hexamethyldisilazide (LiHMDS). In certain embodiments, the base is lithium diisopropylamide (LDA). In certain embodiments, the base is lithium tetramethylpiperidide (LiTMP or harpoon base). In certain embodiments, the base is n-butyllithium. In certain embodiments, the base is sec-butyllithium. In certain embodiments, the base is tert-butyllithium. In certain embodiments, the base is potassium bis(trimethylsilyl)amide, In certain embodiments, the base is sodium tert-butoxide. In certain embodiments, the base is a phosphazene base. In certain embodiments, the base is tert-butylimino-tris(dimethylamino)phosphorane. In certain embodiments, the base is 2-tert-butylimino-2-diethylamino-1,3-dimethylperhydro-1,3,2-diazaphosphorine. In a particular embodiment, the base is potassium tert-butoxide.

In a certain embodiment the transfer hydrogenation is accomplished as described elsewhere herein.

D. Methods of Treatment

In certain embodiments, provided herein is a method of treating, preventing, and/or managing an inflammatory disease, disorder, or condition, comprising administering to a subject a therapeutically effective amount of a treatment compound provided herein.

In certain embodiments, the disease is lupus, scleroderma, Sjögren syndrome, ANCA-induced vasculitis, anti-phospholipid syndrome, or myasthenia gravis. In certain embodiments, the disease is lupus or scleroderma.

In certain embodiments, provided herein is a method of treating, preventing, and/or managing scleroderma or a symptom thereof, comprising administering to a subject having scleroderma a therapeutically effective amount of a treatment compound provided herein. In certain embodiments, provided herein is a method of treating, preventing, and/or managing scleroderma or a symptom thereof, comprising administering to a subject having scleroderma or at risk of having scleroderma a therapeutically effective amount of a treatment provided herein.

In certain embodiments, the scleroderma is localized, systemic, limited, or diffuse scleroderma.

In certain embodiments, the systemic scleroderma comprises CREST syndrome (Calcinosis, Raynaud's syndrome, esophagaeal dysfunction or dysmotility, sclerodactyly, and telangiectasia). Scleroderma is also known as systemic sclerosis or progressive systemic sclerosis.

In certain embodiments, the disease is Raynaud's disease. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life.

In certain embodiments, limited scleroderma is limited to the hands, the face, neck, or combinations thereof.

In certain embodiments, diffuse scleroderma comprises skin tightening and also occurs above the wrists (or elbows). In certain embodiments, the diffuse systemic sclerosis is sine scleroderma, comprising internal organ fibrosis, but no skin tightening; or familial progressive systemic sclerosis.

In one embodiment, scleroderma is not associated with wasting, such as disease-related wasting.

In one embodiment, provided herein is a method for the reduction, inhibition, or prevention of one or more of the following symptoms of scleroderma: (i) gradual hardening, thickening, and tightening of the skin (e.g., in extremities, such as hands, face, and feet); (ii) skin discoloration; (iii) numbness of extremities; (iv) shiny skin; (v) small white lumps under the surface of the skin that erupt into a chalky white fluid; (vi) Raynaud's esophagaeal dysfunction (pain, numbness, and/or color changes in the hands caused by spasm of the blood vessels upon exposure to cold or emotional stress); (vii) telangiectasia (red spots on, e.g., the hands, palms, forearms, face, and lips); (viii) pain and/or stiffness of the joints; (ix) swelling of the hands and feet; (x) itching of the skin; (xi) stiffening and curling of the fingers; (xii) ulcers (sores) on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; or (xx) digital autoamputation, comprising administering a therapeutically effective amount of a treatment provided herein to a subject in need thereof.

Without being bound to any particular theory, it is believed that the treatment provided herein compounds provided herein enhance Th1 immune response, and suppresses Th2 immune response, which may result in antifibrotic effects in the skin.

In certain embodiments, provided herein is a method for improving or reducing the skin thickness of a subject having scleroderma, comprising administering to the subject a therapeutically effective amount of a treatment compound provided herein. In one embodiment, the skin thickness is reduced by about 20%, about 25%, about 30%, about 40%, about 50%, about 60%, about 70% about 80%, about 90% or more.

In certain embodiments, provided herein is a method for achieving one or more clinical endpoints in treating a subject with scleroderma, comprising administering to the subject a therapeutically effective amount of a treatment compound provided herein.

In certain embodiments, provided herein is a method for increasing the overall survival, objective response rate, time to progression, progression-free survival and/or time-to-treatment failure of a subject having scleroderma, comprising administering to the subject a therapeutically effective amount of a treatment compound provided herein.

In certain embodiments, provided herein is a method for decreasing mortality, respiratory mortality and/or respiratory hospitalization of a subject having scleroderma, comprising administering to the subject a therapeutically effective amount of a treatment compound provided herein.

In certain embodiments, provided herein is a method for improving the modified Rodnan skin score of a subject having scleroderma, comprising administering to the subject a therapeutically effective amount of a treatment provided herein. In one embodiment, the improvement in modified Rodnan skin score is about 5, about 10, about 15, or about 20 points or more.

In certain embodiments, provided herein is a method for improving or reducing the skin thickness of a subject having scleroderma, comprising administering to the subject a therapeutically effective amount of a treatment compound provided herein. In one embodiment, the skin thickness is reduced by about 20%, about 25%, about 30%, about 40%, about 50%, about 60%, about 70% about 80%, about 90% or more.

In certain embodiments, provided herein is a method for improving or reducing skin induration of a subject having scleroderma, comprising administering to the subject a therapeutically effective amount of a treatment compound provided herein.

In certain embodiments, provided herein is a method for improving the dermatology quality of life index of a subject having scleroderma, comprising administering to the subject a therapeutically effective amount of a treatment compound provided herein.

In certain embodiments, provided herein is a method for improving the pulmonary function of a subject having scleroderma, comprising administering to the subject a therapeutically effective amount of a treatment compound provided herein.

In certain embodiments, provided herein is a method for improving the carbon monoxide diffusing capacity of a subject having scleroderma, comprising administering to the subject a therapeutically effective amount of a treatment compound provided herein. In one embodiment, the carbon monoxide diffusing capacity of a subject is improved by an improvement in the diffusing capacity of the lung for carbon monoxide ($D_Lco$) of about 10%, about 20%, about 25%, about 30%, about 40%, about 50%, about 60%, about 70% about 80%, about 90% or more.

In certain embodiments, provided herein is a method for improving the Mahler Dyspnea index of a subject having scleroderma, comprising administering to the subject a therapeutically effective amount of a treatment compound provided herein. In one embodiment, the improvement in Mahler Dyspnea index is about 4, about 5, about 6, about 7, about 8, about 9, or about 10 points or more.

In certain embodiments, provided herein is a method for improving the Saint George's Respiratory Questionnaire score of a subject having scleroderma, comprising administering to the subject a therapeutically effective amount of a treatment compound provided herein. In one embodiment, the improvement in Saint George's Respiratory Questionnaire score is about 4, about 8, about 12, about 16, about 20, about 24, about 28, about 32, about 36, about 40, about 44, about 48, about 52 points or more.

In certain embodiments, provided herein is a method for improving the UCLA scleroderma clinical trial consortium gastrointestinal tract score of a subject having scleroderma, comprising administering to the subject a therapeutically effective amount of a treatment compound provided herein.

In certain embodiments, provided herein is a method for treating or preventing digital ulcer of a subject having scleroderma, comprising administering to the subject a therapeutically effective amount of a treatment compound provided herein.

In certain embodiments, provided herein is a method for improving flow-mediated dilatation of a subject having scleroderma, comprising administering to the subject a therapeutically effective amount of a treatment compound provided herein.

In certain embodiments, provided herein is a method for improving or increasing the six minute walk distance of a subject having scleroderma, comprising administering to the subject a therapeutically effective amount of a treatment compound provided herein. In one embodiment, the improvement in the six minute walk distance is about 200 meters, about 250 meters, about 300 meters, about 350 meters, about 400 meters or more.

In certain embodiments, provided herein is a method of treating, preventing, and/or managing lupus erythematosus or a symptom thereof, comprising administering to a subject having lupus erythematosus a therapeutically effective amount of a treatment compound provided herein.

In certain embodiments, provided herein is a method of preventing lupus erythematosus or a symptom thereof, comprising administering to a subject at risk of having lupus erythematosus a therapeutically effective amount of a treatment compound provided herein.

In certain embodiments, the disease is systemic lupus erythematosus (SLE), cutaneous lupus erythematosus (CLE), or drug-induced lupus.

The phrase "Systemic lupus erythematosus" is interchangeably used herein with SLE and lupus and refers to all manifestations of the disease as known in the art (including remissions and flares). In SLE, abnormal hyperactivity of B lymphocytes and massive abnormal production of immunoglobulin gamma (IgG) auto-antibodies play a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In: *Harrison's Principles of Internal Medicine* (16th edition); New York (US): McGraw-Hill; 2005. pp. 1960-1967).

Symptoms of SLE vary from person to person, and may come and go. In most patients, the symptoms include joint pain and swelling. Frequently affected joints are the fingers, hands, wrists, and knees. Some patients develop arthritis. Other common symptoms include: chest pain when taking a deep breath, fatigue, fever with no other cause, general discomfort, uneasiness, or ill feeling (malaise), hair loss, mouth sores, swollen lymph nodes, sensitivity to sunlight, skin rash—a "butterfly" rash over the cheeks and bridge of the nose affects about half of people with SLE, in some patients, the rash gets worse in sunlight, and the rash may also be widespread.

Other symptoms depend on what part of the body is affected, and may include the following:

Brain and nervous system: headaches, numbness, tingling, seizures, vision problems, personality changes,
Digestive tract: abdominal pain, nausea, and vomiting,
Heart: abnormal heart rhythms (arrhythmias),
Lung: coughing up blood and difficulty breathing, and
Skin: patchy skin color, fingers that change color when cold (Raynaud's phenomenon).

Some patients only have skin symptoms. This is called discoid lupus.

In one embodiment, the disease is moderate, severe, or very severe SLE. The term "severe SLE" as used herein refers to an SLE condition where the patient has one or more severe or life-threatening symptoms (such as hemolytic anemia, extensive heart or lung involvement, kidney disease, or central nervous system involvement).

In certain embodiments, provided herein is a method for achieving one or more clinical endpoints in treating a subject with SLE, comprising administering to the subject a therapeutically effective amount of a treatment compound provided herein.

In certain embodiments, provided herein is a method for the overall survival, objective response rate, time to progression, progression-free survival and/or time-to-treatment failure of a subject having SLE, comprising administering to the subject a therapeutically effective amount of a treatment compound provided herein.

In certain embodiment, certain treatment compounds provided herein act as an inhibitor of primary human memory CD19+ B-cell differentiation to the plasmablast stage. Without being bound to any particular theory, it is believed that certain treatment compounds provided herein block cells at a premature stage thereby decreasing the numbers of plasmablasts that are capable of producing high levels of immunoglobulin. A functional consequence of this effect is reduced immunoglobulin G (IgG) and immunoglobulin M (IgM) production in these differentiation cultures.

In certain embodiments, provided herein is a method for treating, managing, or preventing an immune-related disease, disorder, or condition, comprising administering to a subject a therapeutically effective amount of a treatment compound provided herein.

In certain embodiments, provided herein is a method of treating a disease, disorder, or condition caused by, or is associated with, an inappropriate or undesirable immune response, comprising administering to a subject a therapeutically effective amount of a treatment compound provided herein.

In certain embodiments, provided herein is a method of treating a disease, disorder, or condition that can be treated beneficially by immunosuppression, comprising administering to a subject a therapeutically effective amount of a treatment compound provided herein.

In certain embodiments, the immune-related disease, i.e., a disease, disorder, or condition caused by, or is associated with, an inappropriate or undesirable immune response, is Sjögren syndrome, ANCA-induced vasculitis, anti-phospholipid syndrome, myasthenia gravis, Addison's disease, alopecia areata, ankylosing spondylitis, antiphospholipid antibody syndrome, antiphospholipid syndrome (primary or secondary), asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, degos disease, dermatitis hepatiformis, essential mixed cryoglobulinemia, Goodpasture's syndrome, Graves' disease, Guillain-Barre syndrome, Hashimoto's thyroiditis (Hashimoto's disease; autoimmune thyroditis), idiopathic pulmonary fibrosis, idiopathic thrombocytopenia purpura, IgA nephropathy, juvenile arthritis, lichen planus, Ménierè disease, mixed connective tissue disease, morephea, narcolepsy, neuromyotonia, pediatric autoimmune neuropsychiatric disorders (PANDAs), *pemphigus vulgaris*, pernicious anemia, polyarteritis nodosa, polychondritis, polymyalgia rheumatica, primary agammaglobulinemia, primary biliary cirrhosis, Raynaud disease (Raynaud phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, or Wegener's granulomatosis.

In certain embodiments, provided herein is a method for treating and preventing cancer, comprising administering to a subject a therapeutically effective amount of a treatment compound provided herein.

In certain embodiments, provided herein is a method for managing cancer, comprising administering to a subject a therapeutically effective amount of a treatment compound provided herein.

In certain embodiments, provided herein is a method for treating or managing lymphoma, in one embodiment, non-Hodgkin's lymphoma, comprising administering to a subject a therapeutically effective amount of a treatment compound provided herein.

In certain embodiments, provided herein is a method for treating or managing non-Hodgkin's lymphoma (NHL), including but not limited to, diffuse large B-cell lymphoma (DLBCL), comprising administering to a subject a therapeutically effective amount of a treatment compound provided herein.

In certain embodiments, the subject is one who has been previously treated for cancer, but is non-responsive to a standard therapy. In certain embodiments, the subject is one who has not previously been treated.

As used herein, the term "cancer" includes, but is not limited to, solid tumors and blood born tumors. In certain embodiments, the term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus.

In certain embodiments, the term "cancer" refers to advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a blood borne tumor. In certain embodiments, the blood borne tumor is metastatic. In certain embodiments, the blood borne tumor is drug resistant. In certain embodiments, the cancer is myeloma or lymphoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

E. Second Active Agents

A compound provided herein, or a pharmaceutically acceptable salt, solvate, prodrug, clathrate, cocrystal, polymorph or stereoisomer thereof, can be combined with other pharmacologically active compounds ("second active agents") in methods and compositions provided herein. Certain combinations may work synergistically in the treatment of particular types diseases or disorders, and conditions and symptoms associated with such diseases or disorders. A compound provided herein, or a pharmaceutically acceptable salt, solvate, clathrate, cocrystal, polymorph, stereoisomer or prodrug thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetlyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

Specific second active compounds that can be combined with compounds provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In another embodiment, examples of specific second agents according to the indications to be treated, prevented, or managed can be found in the following references, all of which are incorporated herein in their entireties: U.S. Pat. Nos. 6,281,230 and 5,635,517; U.S. publication nos. 2004/0220144, 2004/0190609, 2004/0087546, 2005/0203142, 2004/0091455, 2005/0100529, 2005/0214328, 2005/0239842, 2006/0154880, 2006/0122228, and 2005/0143344; and U.S. provisional application No. 60/631,870.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Administration of a compound provided herein, or a pharmaceutically acceptable salt, solvate, clathrate, cocrystal, polymorph, stereoisomer or prodrug thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for compounds provided herein is oral. Routes of administration for the second active agents or ingredients are known to those of ordinary skill in the art. See, e.g., *Physicians' Desk Reference* (60$^{th}$ ed., 2006).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

F. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, cocrystal, polymorph or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed in Section 4.4, above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences*, 18th ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

1. Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as *acacia*, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

2. Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

3. Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

4. Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences*, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, cocrystals, polymorphs, or stereoisomers of the active ingredients can be used to further adjust the properties of the resulting composition.

G. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 4.3).

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. EXAMPLES

Certain embodiments are illustrated by the following non-limiting examples. The discussion below is offered to illustrate certain of the diverse methods available for use in making the disclosed compounds and is not intended to limit the scope of reactions or reaction sequences that can be used in preparing the compounds provided herein.

Example 1

The gluarimide portion of the 3-(5-amino-2-methyl-4-oxoquinazolin-3(4H)-yl)piperidine-2,6-dione is enriched with deuterium as follows. 3-(5-amino-2-methyl-4-oxoquinazolin-3(4H)-yl)piperidine-2,6-dione 3 is contacted with potassium tert-butoxide in tert-butyl alcohol and allowed to stir at room temperature for 2 hours. The reaction is subsequently treated with aqueous acid, concentrated and purified to obtain deuterated 3-(5-amino-2-methyl-4-oxoquinazolin-3(4H)-yl)piperidine-2,6-dione 4 as a mixture of enantiomers. The isotopically enriched products 5 and 6 are obtained by chiral separation.

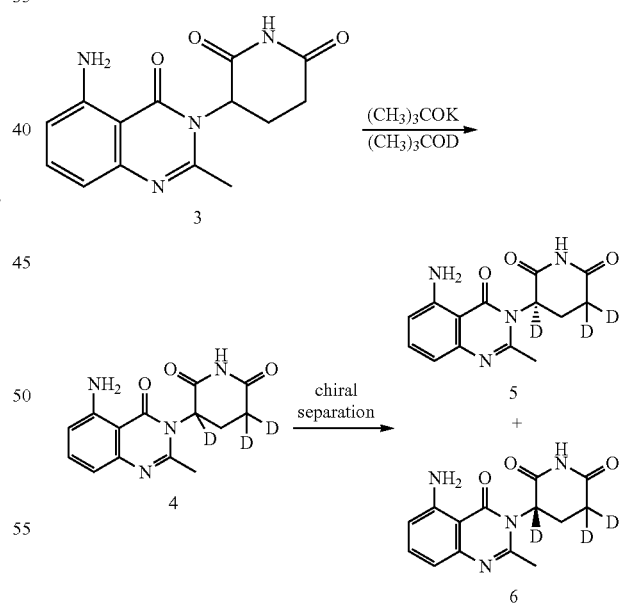

Example 2

The oxoquinazoline portion of 3-(5-amino-2-methyl-4-oxoquinazolin-3(4H)-yl)piperidine-2,6-dione is enriched with deuterium as follows: 3-(5-amino-2-methyl-4-oxoquinazolin-3(4H)-yl)piperidine-2,6-dione hydrochloride 3A is dissolved in DMSO-$d_6$ and $D_2O$ and allowed to stir at room temperature for ten hours to generate compound 7 as a salt. The reaction mixture may optionally be treated with aqueous sodium carbonate to generate the free base, concentrated and purified to obtain deuterated 3-(5-amino-2-methyl-4-oxo-quinazolin-3(4H)-yl)piperidine-2,6-dione 8. The isotopically enriched products 9 and 10 are obtained by chiral separation.

2-methyl-4-oxoquinazolin-3 (4H)-yl)piperidine-2,6-dione hydrochloride 3A is dissolved in DMSO-d₆ and D₂O and allowed to stir at room temperature. After two hours, the reaction quenched, concentrated and purified to obtain 7. Compound 7 is subsequently treated with potassium tert-butoxide in tert-butyl alcohol and allowed to stir for an additional 2 hours. The reaction mixture is then quenched, concentrated and purified to obtain deuterated 3-(5-amino-2-methyl-4-oxoquinazolin-3 (4H)-yl)piperidine-2,6-dione 11 as a mixture of enantiomers. The isotopically enriched products 12 and 13 are obtained by chiral separation.

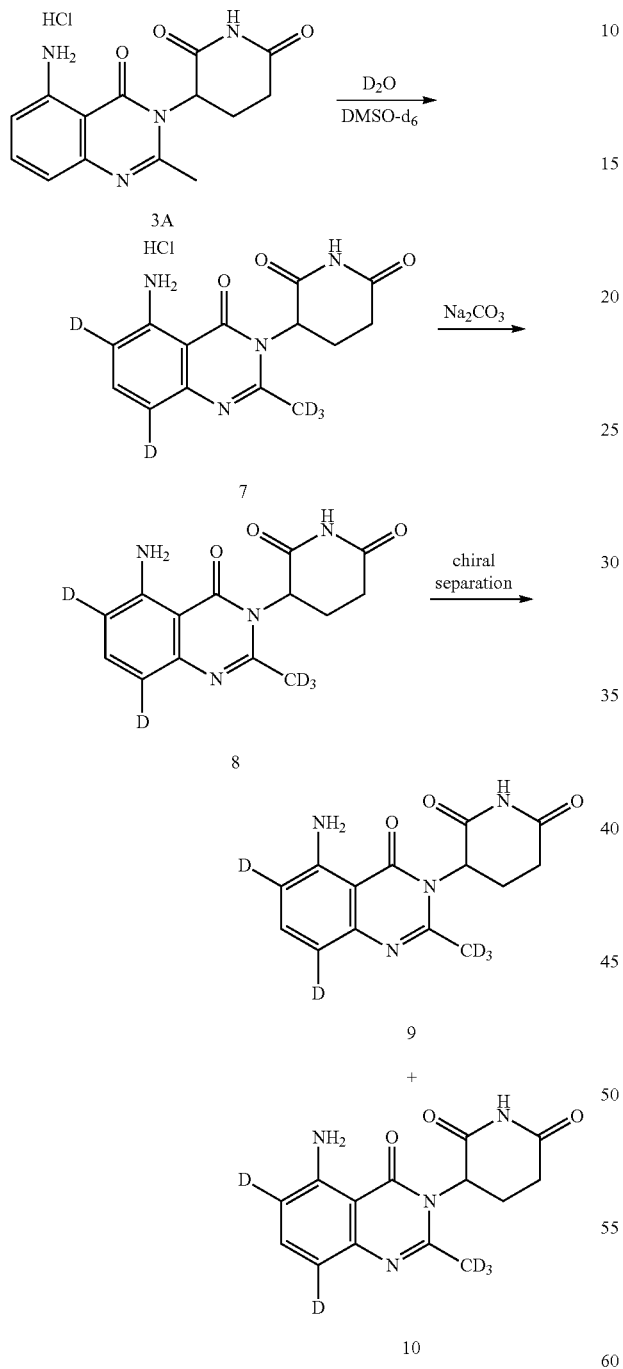

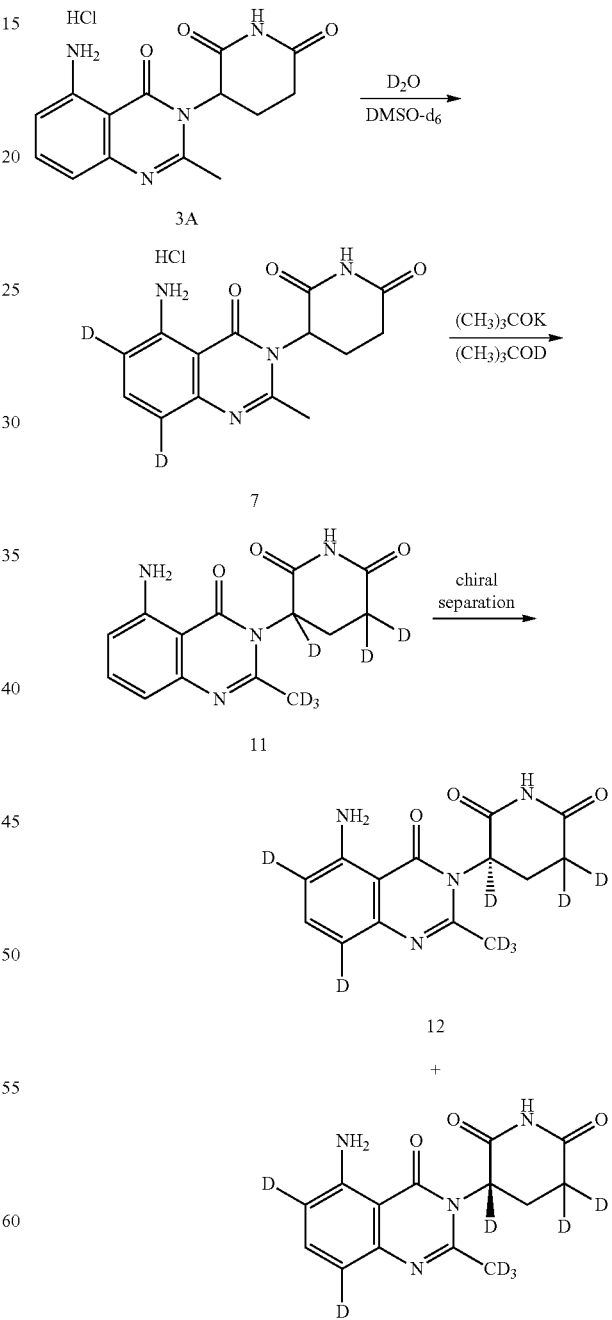

Example 3

The oxoquinazoline and gluarimide portions of 3-(5-amino-2-methyl-4-oxoquinazolin-3(4H)-yl)piperidine-2,6-dione are enriched with deuterium as follows: 3-(5-amino-

Example 4

Deuterated isotopologues 18 and 19 of 3-(5-amino-2-methyl-4-oxoquinazolin-3(4H)-yl)piperidine-2,6-dione is prepared as follows. 2-amino-6-nitrobenzoic acid 14 is stirred overnight in acetic anhydride under reflux to obtain 2-methyl-5-nitro-4H-benzo[d][1,3]oxazin-4-one 15. The resulting oxazinone is further contacted with 3,4,4,5,5-pentadeuteroglutarimide in the presence of POCl₃/H₂O and diisopropylethylamine and refluxed in N-methyl-2-pyrrolidinone (NMP) for 12 hours and subsequently purified to give isotopologue 16 of 3-(2-methyl-5-nitro-4-oxoquinazolin-3(4H)-yl)piperidine-2,6-dione. Compound 16 is subsequently subjected to transfer hydrogenation with DCOOD/D₂O and 10% Pd/C; the catalyst is filtered off through a celite pad and the filtrate is concentrated and purified to obtain isotopologue 17 as a mixture of enantiomers. The isotopically enriched products 18 and 19 are obtained by chiral separation.

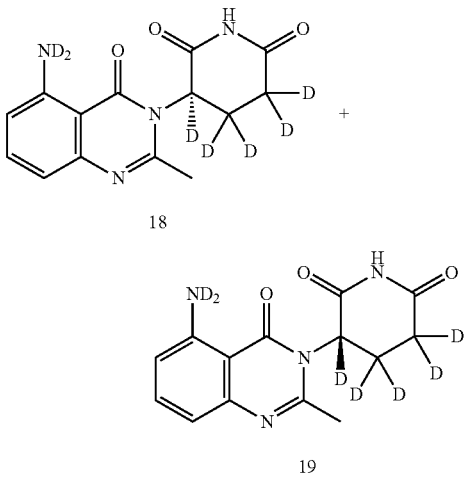

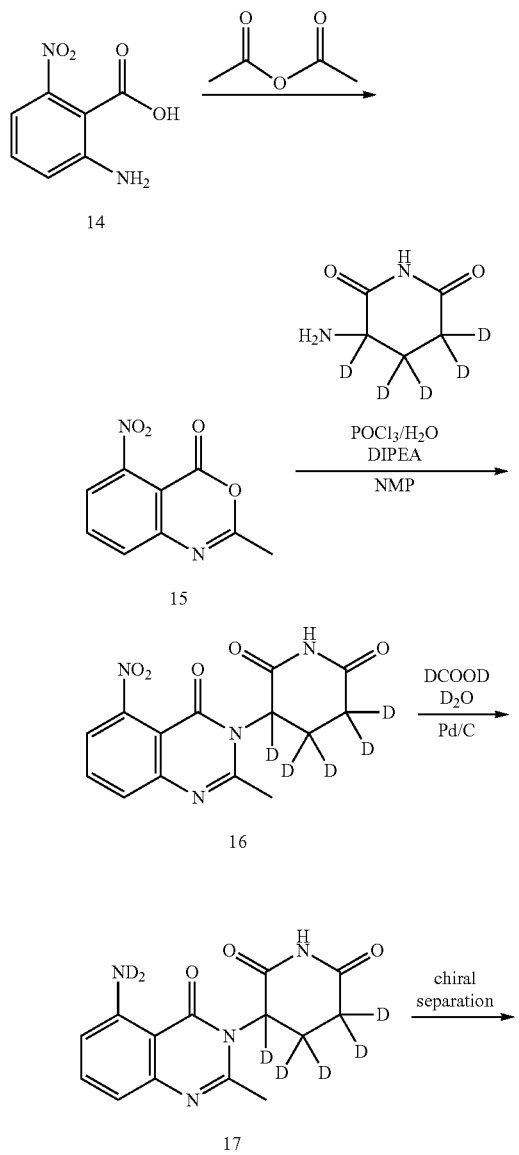

Example 5

Deuterated isotopologues 22 and 23 of 3-(5-amino-2-methyl-4-oxoquinazolin-3(4H)-yl)piperidine-2,6-dione is prepared as follows. 2-amino-6-nitrobenzoic acid 14 is stirred overnight in acetic anhydride under reflux to obtain 2-methyl-5-nitro-4H-benzo[d][1,3]oxazin-4-one 15. The resulting oxazinone is further contacted with 3,4,5-trideuteroglutarimide in the presence of POCl₃/H₂O and diisopropylethylamine and refluxed in N-methyl-2-pyrrolidinone (NMP) for 12 hours and subsequently purified to give isotopologue 20 of 3-(2-methyl-5-nitro-4-oxoquinazolin-3(4H)-yl)piperidine-2,6-dione. Compound 20 is subsequently subjected to transfer hydrogenation with DCOOD/D₂O and 10% Pd/C; the catalyst is filtered off through a celite pad and the filtrate concentrated and purified to obtain isotopologue 21 as a mixture of enantiomers. The isotopically enriched products 22 and 23 are obtained by chiral separation.

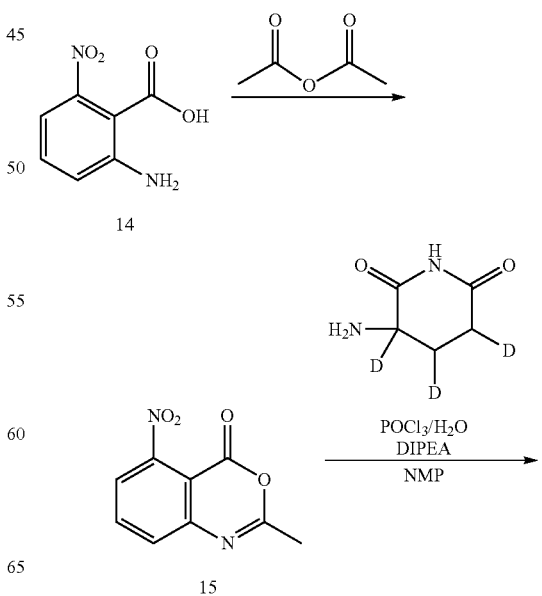

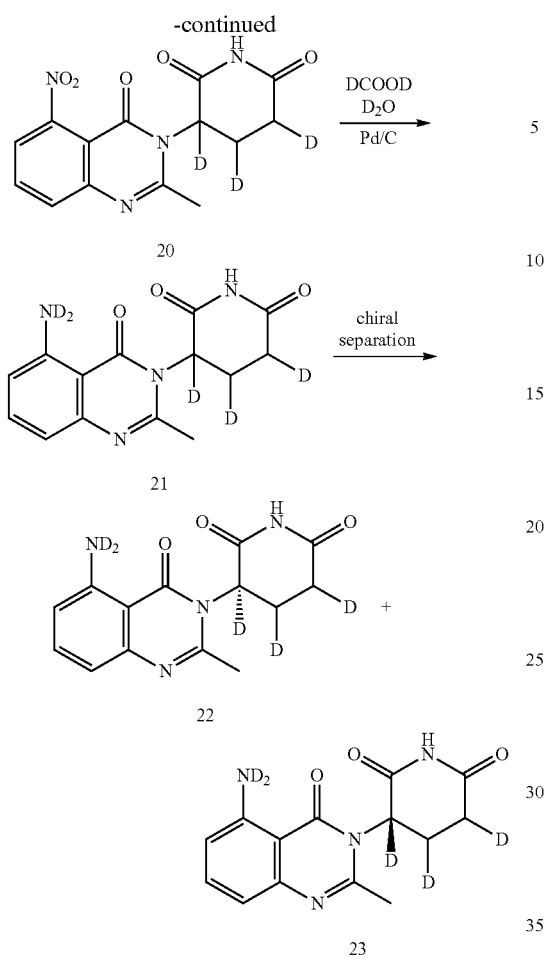

Example 6

Deuterated isotopologue 27 and 28 of 3-(5-amino-2-methyl-4-oxoquinazolin-3(4H)-yl)piperidine-2,6-dione are prepared as follows. 2-amino-6-nitrobenzoic acid 14 is stirred overnight in acetic anhydride-$d_6$ under reflux to obtain 2-methyl-5-nitro-4H-benzo[d][1,3]oxazin-4-one. The resulting oxazinone 24 is further contacted with 3,4,4,5,5-pentadeuteroglutarimide in the presence of $POCl_3/H_2O$ and diisopropylethylamine and refluxed in N-methyl-2-pyrrolidinone (NMP) for 12 hours. The subsequent reaction mixture is cooled and purified to give oxoquinazoline 23. The nitro-substituted quinazoline 25 is subjected to transfer hydrogenation in the presence of $DCOOD/D_2O$ and 10% Pd/C; the catalyst is filtered off through a celite pad and the filtrate concentrated and purified to obtain isotopologue 26 as a mixture of enantiomers. The isotopically enriched products 27 and 28 are obtained by chiral separation.

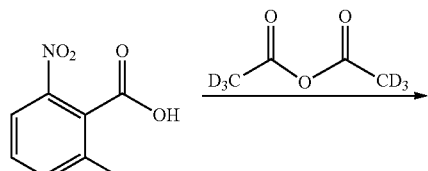

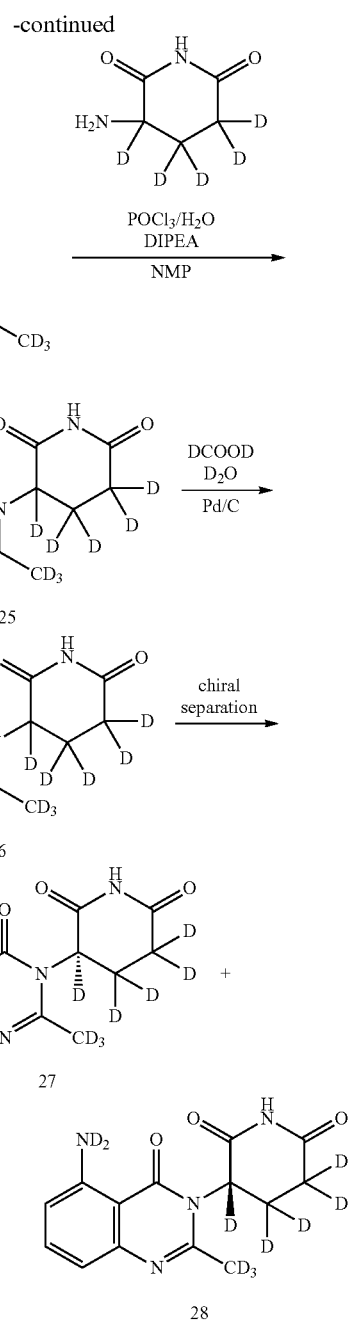

Example 7

Isotopologues 30 and 31 of 3-(5-amino-2-methyl-4-oxo-quinazolin-3(4H)-yl)piperidine-2,6-dione are prepared as follows. 2-amino-6-nitrobenzoic acid 14 is stirred overnight in acetic anhydride under reflux to obtain 2-methyl-5-nitro-4H-benzo[d][1,3]oxazin-4-one 15. The resulting oxazinone is further contacted with 3,4,4,5,5-pentadeuteroglutarimide in the presence of $POCl_3/H_2O$ and diisopropylethylamine and refluxed in N-methyl-2-pyrrolidinone (NMP) for 12 hours and subsequently purified to give the isotopologue 16 of 3-(2-methyl-5-nitro-4-oxoquinazolin-3(4H)-yl)piperidine-2,6-dione. Compound 16 is subsequently subjected to transfer hydrogenation with $DCOOD/D_2O$ and 10% Pd/C; the catalyst is filtered off through a celite pad and the filtrate concentrated and purified to obtain isotopologue 15 as a mixture of enantiomers. Oxoquinazoline 17 is subsequently dissolved in DMSO-d$_6$ and D$_2$O, treated with DCl, allowed to stir at room temperature for ten hours to generate compound 29 as a mixture of enantiomers. The isotopically enriched products 30 and 31 are obtained by chiral separation.

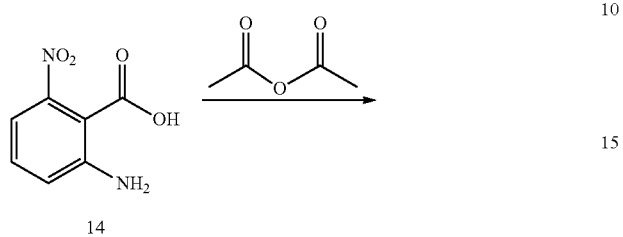

14

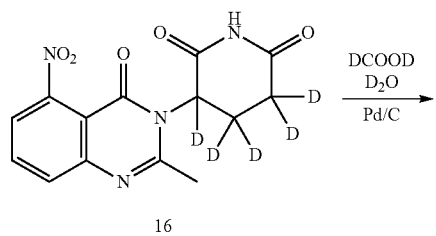

15

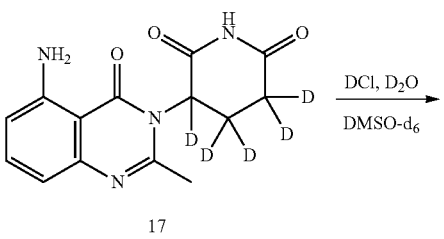

16

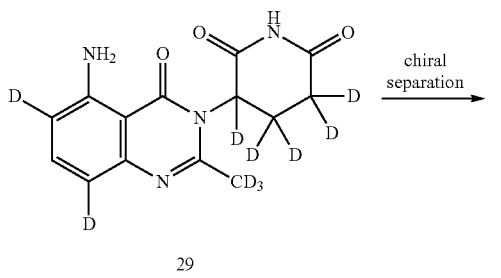

17

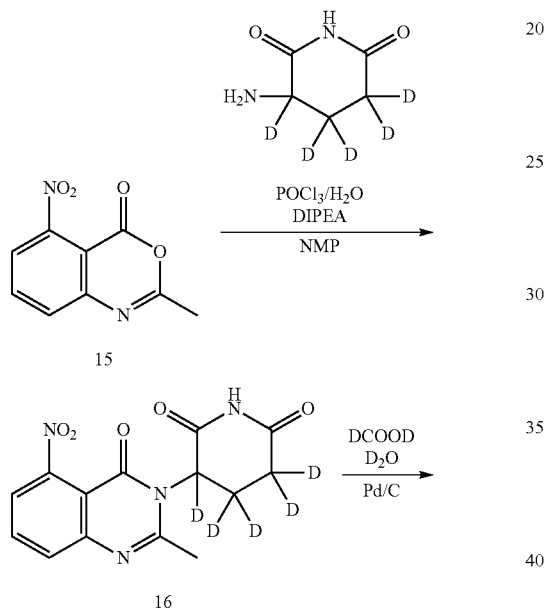

29

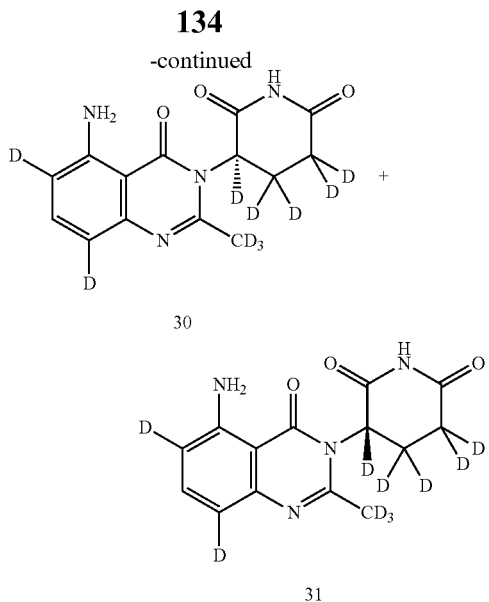

30

31

Example 8

Isotopologue 36 of 3-(5-amino-2-methyl-4-oxoquinazolin-3(4H)-yl)piperidine-2,6-dione is prepared as follows. 2-Amino-6-nitrobenzoic acid 14 is stirred overnight with triphosgene in THF, concentrated and purified to obtain 5-nitro-1H-benzo[d][1,3]oxazine-2,4-dione 32. Dione 32 is dissolved in acetonitrile, and deuterated glutamic acid methyl ester and sodium bicarbonate are added. The reaction mixture is stirred at 50° C. for 4 hours, concentrated and purified to give compound 33. Treatment of compound 33 with triethylorthoacetate and PTSA hydrate in DMSO at 120° C. provides oxoquinazoline 34. Subsequent treatment of 34 with potassium tert-butoxide in THF at −78° C. affords cyclization to glutarimide 35. Purification of the glutarimide 35 followed by transfer hydrogenation provides isotopologue 36 in enantiomerically pure form.

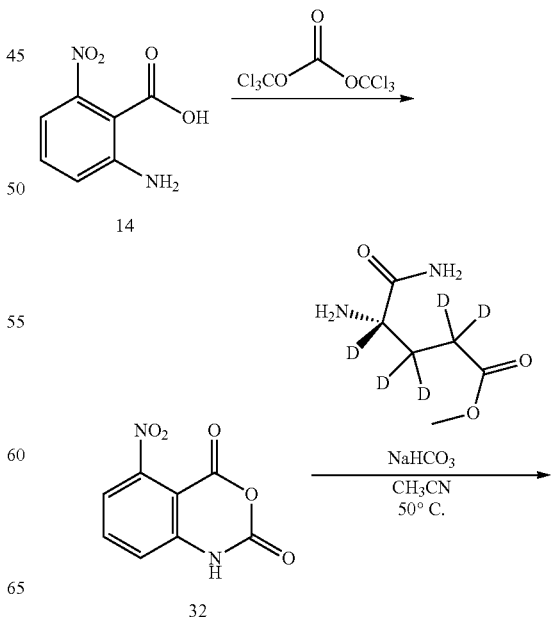

14

32

-continued

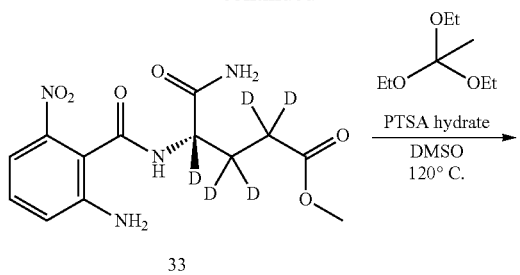

33

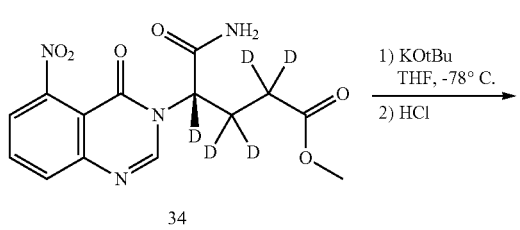

34

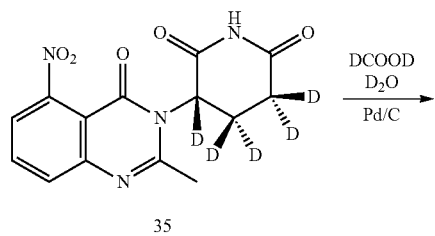

35

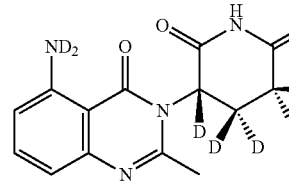

36

Example 9

Deuterated isotopologue 39 and 40 of 3-(5-amino-2-methyl-4-oxoquinazolin-3(4H)-yl)piperidine-2,6-dione are prepared as follows. 2-amino-6-nitrobenzoic acid 14 is stirred overnight in acetic anhydride-d$_6$ under reflux to obtain 2-methyl-5-nitro-4H-benzo[d][1,3]oxazin-4-one 24. The resulting oxazinone 24 is further contacted with 3-aminopiperidine-2,6-dione in the presence of POCl$_3$/H$_2$O and diisopropylethylamine and refluxed in N-methyl-2-pyrrolidinone (NMP) for 12 hours. The subsequent reaction mixture is purified to give oxoquinazoline 37. The nitro-substituted quinazoline 37 is subjected to transfer hydrogenation in the presence of DCOOD/D$_2$O and 10% Pd/C; the catalyst is filtered off through a celite pad and the filtrate concentrated and purified to obtain isotopologue 38 as a mixture of enantiomers. The isotopically enriched products 39 and 40 are obtained by chiral separation.

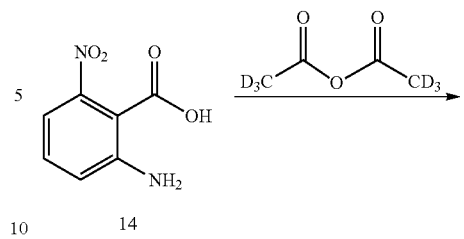

14

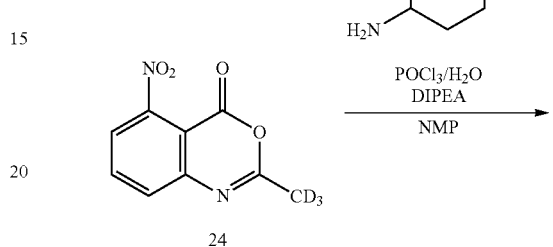

24

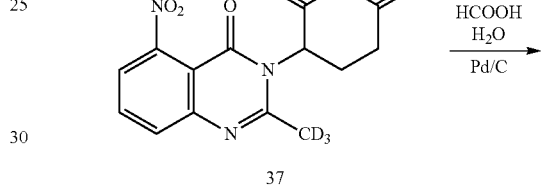

37

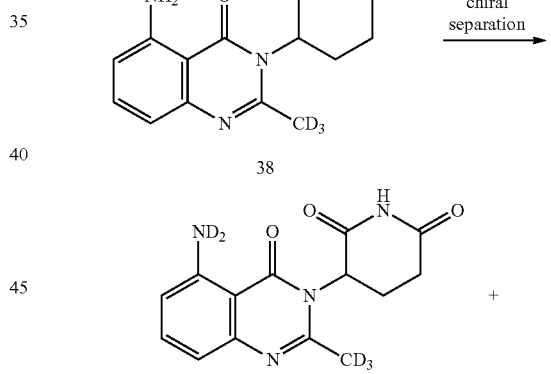

38

39

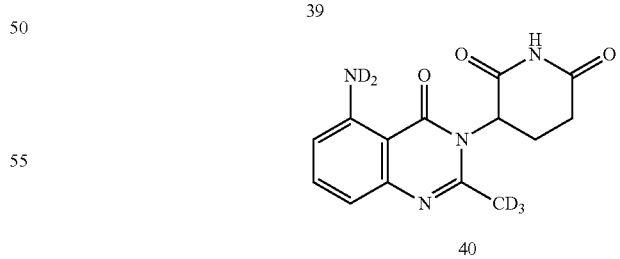

40

While examples of certain particular embodiments are provided herein, it will be apparent to those skilled in the art that various changes and modifications may be made. Such modifications are also intended to fall within the scope of the appended claims.

What is claimed:
1. A compound of the formula:

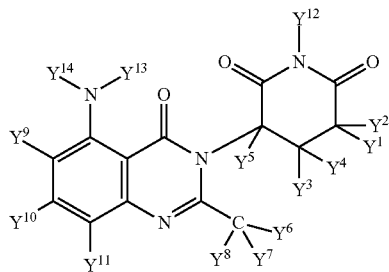

or a pharmaceutically acceptable salt thereof, wherein:
at least one of $Y^1$, $Y^2$, $Y^3$, $Y^4$, $Y^6$, $Y^7$, $Y^8$, $Y^9$, $Y^{10}$, $Y^{11}$, $Y^{12}$, $Y^{13}$ and $Y^{14}$ is a hydrogen that is isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$ and $Y^{14}$ are non-enriched hydrogen atoms.

2. The compound of claim 1, wherein one of $Y^1$, $Y^2$, $Y^3$, $Y^4$, $Y^6$, $Y^7$, $Y^8$, $Y^9$, $Y^{10}$, $Y^{11}$, $Y^{12}$, $Y^{13}$ and $Y^{14}$ is a hydrogen that is isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$ and $Y^{14}$ are non-enriched hydrogen atoms.

3. The compound of claim 1, wherein two, three, four, five, six, seven, eight, nine, ten, eleven, twelve, or all of $Y^1$, $Y^2$, $Y^3$, $Y^4$, $Y^6$, $Y^7$, $Y^8$, $Y^9$, $Y^{10}$, $Y^{11}$, $Y^{12}$, $Y^{13}$ and $Y^{14}$ are hydrogen atoms that are isotopically enriched with deuterium, and the others of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$ and $Y^{14}$ are non-enriched hydrogen atoms.

4. A pharmaceutical composition comprising a compound of claim 1 or a pharmaceutically acceptable salt thereof.

5. The compound of claim 2, wherein $Y^1$ is a hydrogen that is isotopically enriched with deuterium.

6. The compound of claim 2, wherein $Y^3$ is a hydrogen that is isotopically enriched with deuterium.

7. The compound of claim 2, wherein $Y^6$ is a hydrogen that is isotopically enriched with deuterium.

8. The compound of claim 2, wherein $Y^9$ is a hydrogen that is isotopically enriched with deuterium.

9. The compound of claim 2, wherein $Y^{10}$ is a hydrogen that is isotopically enriched with deuterium.

10. The compound of claim 2, wherein $Y^{11}$ is a hydrogen that is isotopically enriched with deuterium.

* * * * *